(12) United States Patent
Packer et al.

(10) Patent No.: US 7,816,391 B2
(45) Date of Patent: Oct. 19, 2010

(54) CHEMICAL COMPOUNDS

(75) Inventors: Martin John Packer, Cheshire (GB); James Stewart Scott, Cheshire (GB); Andrew Stocker, Cheshire (GB); Paul Robert Owen Whittamore, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/259,562

(22) Filed: Oct. 28, 2008

(65) Prior Publication Data

US 2009/0221663 A1  Sep. 3, 2009

Related U.S. Application Data

(63) Continuation of application No. PCT/GB2008/000454, filed on Feb. 11, 2008.

(60) Provisional application No. 60/889,336, filed on Feb. 12, 2007, provisional application No. 60/985,735, filed on Nov. 6, 2007.

(51) Int. Cl.
A01N 43/56 (2006.01)
C07D 231/02 (2006.01)
C07D 231/54 (2006.01)

(52) U.S. Cl. .................................. 514/406; 548/356.5

(58) Field of Classification Search .................. 514/406; 548/365.5
See application file for complete search history.

(56) References Cited

U.S. PATENT DOCUMENTS

| 4,250,178 | A | 2/1981 | Bucher et al. | |
|---|---|---|---|---|
| 2004/0142930 | A1 | 7/2004 | Yamada et al. | |
| 2006/0223852 | A1 | 10/2006 | Gillespie et al. | |
| 2006/0235028 | A1 | 10/2006 | Li et al. | |
| 2007/0225280 | A1* | 9/2007 | Anderson et al. | 514/227.5 |
| 2008/0269288 | A1 | 10/2008 | McCoull et al. | |
| 2009/0221660 | A1 | 9/2009 | Tomkinson et al. | |
| 2009/0221663 | A1 | 9/2009 | Packer et al. | |
| 2009/0264401 | A1 | 10/2009 | Gill et al. | |
| 2009/0306075 | A1 | 12/2009 | McCoull et al. | |
| 2009/0312372 | A1 | 12/2009 | McCoull et al. | |
| 2010/0022589 | A1 | 1/2010 | McCoull et al. | |

FOREIGN PATENT DOCUMENTS

| EP | 0188094 | 7/1986 |
|---|---|---|
| EP | 1219609 | 7/2002 |
| EP | 1600442 | 11/2005 |
| EP | 1889842 | 2/2008 |
| EP | 1894919 | 3/2008 |
| WO | WO 02/20463 | 3/2002 |
| WO | WO 02/34711 | 5/2002 |
| WO | WO 03/015774 | 2/2003 |
| WO | WO 2004/065351 | 8/2004 |
| WO | WO 2004/089470 | 10/2004 |
| WO | WO 2004/089896 | 10/2004 |
| WO | WO 2005/016877 | 2/2005 |
| WO | WO 2005/023761 | 3/2005 |
| WO | WO 2005/054200 | 6/2005 |
| WO | WO 2005/060963 | 7/2005 |
| WO | WO 2005/108359 | 11/2005 |
| WO | WO 2005/121110 | 12/2005 |
| WO | WO 2006/000371 | 1/2006 |
| WO | WO 2006/048750 | 5/2006 |
| WO | WO 2006/050476 | 5/2006 |
| WO | WO 2006/074244 | 7/2006 |
| WO | WO 2006/106054 | 10/2006 |
| WO | WO 2006/106423 | 10/2006 |
| WO | WO 2006/113261 | 10/2006 |
| WO | WO 2006/125958 | 11/2006 |
| WO | WO 2006/132197 | 12/2006 |
| WO | WO 2006/132436 | 12/2006 |
| WO | WO 2006/134467 | 12/2006 |
| WO | WO 2007/007041 | 1/2007 |
| WO | WO 2007/017649 | 2/2007 |
| WO | WO 2007/052843 | 5/2007 |
| WO | WO 2007/053657 | 5/2007 |
| WO | WO 2007/058346 | 5/2007 |
| WO | WO 2007/089683 | 8/2007 |
| WO | WO 2007/107470 | 9/2007 |
| WO | WO 2007/115935 | 10/2007 |
| WO | WO 2007/125049 | 11/2007 |
| WO | WO 2008/012532 | 1/2008 |
| WO | WO 2008/053194 | 5/2008 |

(Continued)

OTHER PUBLICATIONS

Katsuno K, et al., "Sergliflozin, a novel selective inhibitor of low-affinity sodium glucose cotransporter (SGLT2), validates the critical role of SGLT2 in renal glucose reabsorption and modulates plasma glucose level," Journal of Pharmacology and Experimental Therapeutics, Jan. 2007, 320(1), 323-330.*

(Continued)

Primary Examiner—San-ming Hui
Assistant Examiner—Paul Zarek
(74) Attorney, Agent, or Firm—Morgan, Lewis & Bockius LLP

(57) ABSTRACT

A compound of formula (I):

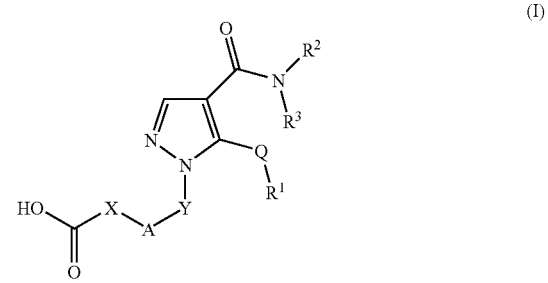

and pharmaceutically-acceptable salts thereof wherein the variable groups are defined within; their use in the inhibition of 11βHSD1, processes for making them and pharmaceutical compositions comprising them are also described.

3 Claims, No Drawings

FOREIGN PATENT DOCUMENTS

| WO | WO 2008/099145 | 8/2008 |
|---|---|---|
| WO | WO 2008/142986 | 11/2008 |
| WO | WO 2009/010416 | 1/2009 |
| WO | WO 2009/098501 | 8/2009 |

OTHER PUBLICATIONS

Boyle "Recent advances in the discovery of 11b-HSD1 inhibitors" Current Opinion in Drug Discovery and Development 11:495-511 (2008).

Jean et al. "Inhibitors of 11ă-HSD1: A Potential Treatment for the Metabolic Syndrome" Current Topics in Medicinal Chemistry 8(17): 1508-1523 (2008).

Shorvon, "Pyrrolidone derivatives" Lancet 358(9296):1885-1892 (2001).

Blake et al. "Discovery of 3,3-dimethyl-azetidin-2-ones as potent and selective inhibitors of 11β-HSD1" Gordon Research Conference on Medicinal Chemistry, Colby-Sawyer College, New London, NH, USA (Aug. 2007).

deSchoolmeester et al. "An increase in obesity is associated with increased 11βHSD1 activity but not expression in mature human subcutaneous adipocytes" Association for the Study of Obesity (ASO) and Adipose Tissue Discussion Group, Institute of Child Health, London (Nov. 9, 2006).

Mayers "11β-hydroxysteroid dehydrogenase type 1: a tale of (fat) mice to men" Abstract and Presentation, Obesity and its Treatment, Society for Medicines Research (Sep. 25, 2008).

Barf et al. Recent progress in 11-beta-hydroxysteroid dehydrogenase type 1 (11-beta-HSD1) inhibitor development Drugs of the Future 31(3):231-243 (2006).

Dostert et al. "Studies on the neuroleptic benzamides I. Synthesis and antidopaminergic properties of new pyrimidine derivatives" European Journal of Medicinal Chemistry 17(5):437-444 (1982).

Hirokawa et al. "Synthesis and structure-affinity relationships of novel N-(1-ethyl-4-methylhexahydro-1,4-diazepin-6-yl)pyridine-3-carboxamides with potent serotonin 5-HT3 and dopamine D2 receptor antagonistic activity" J Med. Chem. 46(5):702-715 (2003).

Hussein et al. "β-Oxoanilides in heterocyclic synthesis: An expeditious synthesis of new polyfunctionally substituted pyridine and pyrazole derivatives" Journal of Heterocyclic Chemistry 45(6):1819-1823 (2008).

Langlois et al. "Studies on the neuroleptic benzamides II. Synthesis and pharmacological evaluation of new 6-azabrendane derivatives" European Journal of Medicinal Chemistry 17(5):445-447 (1982).

* cited by examiner

CHEMICAL COMPOUNDS

This application is a Continuation Application of International Application No. PCT/GB2008/000454, filed Feb. 11, 2008, which claims the benefit of U.S. Provisional Application No. 60/889,336, filed Feb. 12, 2007, and U.S. Provisional Application No. 60/985,735, filed Nov. 6, 2007, all of which are hereby incorporated by reference in their entirety.

This invention relates to chemical compounds, or pharmaceutically-acceptable salts thereof. These compounds possess human 11-β-hydroxysteroid dehydrogenase type 1 enzyme (11βHSD1) inhibitory activity and accordingly have value in the treatment of disease states including metabolic syndrome and are useful in methods of treatment of a warm-blooded animal, such as man. The invention also relates to processes for the manufacture of said compounds, to pharmaceutical compositions containing them and to their use in the manufacture of medicaments to inhibit 11βHSD1 in a warm-blooded animal, such as man.

Glucocorticoids (cortisol in man, corticosterone in rodents) are counter regulatory hormones i.e. they oppose the actions of insulin (Dallman M F, Strack A M, Akana S F et al. 1993; Front Neuroendocrinol 14, 303-347). They regulate the expression of hepatic enzymes involved in gluconeogenesis and increase substrate supply by releasing glycerol from adipose tissue (increased lipolysis) and amino acids from muscle (decreased protein synthesis and increased protein degradation). Glucocorticoids are also important in the differentiation of pre-adipocytes into mature adipocytes which are able to store triglycerides (Bujalska I J et al. 1999; Endocrinology 140, 3188-3196). This may be critical in disease states where glucocorticoids induced by "stress" are associated with central obesity which itself is a strong risk factor for type 2 diabetes, hypertension and cardiovascular disease (Bjorntorp P & Rosmond R 2000; Int. J. Obesity 24, S80-S85).

It is now well established that glucocorticoid activity is controlled not simply by secretion of cortisol but also at the tissue level by intracellular interconversion of active cortisol and inactive cortisone by the 11-beta hydroxysteroid dehydrogenases, 11βHSD1 (which activates cortisone) and 11βHSD2 (which inactivates cortisol) (Sandeep T C & Walker B R 2001 Trends in Endocrinol & Metab. 12, 446-453). That this mechanism may be important in man was initially shown using carbenoxolone (an anti-ulcer drug which inhibits both 11βHSD1 and 2) treatment which (Walker B R et al. 1995; J. Clin. Endocrinol. Metab. 80, 3155-3159) leads to increased insulin sensitivity indicating that 11βHSD1 may well be regulating the effects of insulin by decreasing tissue levels of active glucocorticoids (Walker B R et al. 1995; J. Clin. Endocrinol. Metab. 80, 3155-3159).

Clinically, Cushing's syndrome is associated with cortisol excess which in turn is associated with glucose intolerance, central obesity (caused by stimulation of pre-adipocyte differentiation in this depot), dyslipidaemia and hypertension. Cushing's syndrome shows a number of clear parallels with metabolic syndrome. Even though the metabolic syndrome is not generally associated with excess circulating cortisol levels (Jessop D S et al. 2001; J. Clin. Endocrinol. Metab. 86, 4109-4114) abnormally high 11βHSD1 activity within tissues would be expected to have the same effect. In obese men it was shown that despite having similar or lower plasma cortisol levels than lean controls, 11βHSD1 activity in subcutaneous fat was greatly enhanced (Rask E et al. 2001; J. Clin. Endocrinol. Metab. 1418-1421). Furthermore, the central fat, associated with the metabolic syndrome expresses much higher levels of 11βHSD1 activity than subcutaneous fat (Bujalska I J et al. 1997; Lancet 349, 1210-1213). Thus there appears to be a link between glucocorticoids, 11βHSD1 and the metabolic syndrome.

11βHSD1 knock-out mice show attenuated glucocorticoid-induced activation of gluconeogenic enzymes in response to fasting and lower plasma glucose levels in response to stress or obesity (Kotelevtsev Y et al. 1997; Proc. Natl. Acad. Sci USA 94, 14924-14929) indicating the utility of inhibition of 11βHSD1 in lowering of plasma glucose and hepatic glucose output in type 2 diabetes. Furthermore, these mice express an anti-atherogenic lipoprotein profile, having low triglycerides, increased HDL cholesterol and increased apo-lipoprotein AI levels. (Morton N M et al. 2001; J. Biol. Chem. 276, 41293-41300). This phenotype is due to an increased hepatic expression of enzymes of fat catabolism and PPARα. Again this indicates the utility of 11βHSD1 inhibition in treatment of the dyslipidaemia of the metabolic syndrome.

The most convincing demonstration of a link between the metabolic syndrome and 11βHSD1 comes from recent studies of transgenic mice over-expressing 11βHSD1 (Masuzaki H et al. 2001; Science 294, 2166-2170). When expressed under the control of an adipose specific promoter, 11βHSD1 transgenic mice have high adipose levels of corticosterone, central obesity, insulin resistant diabetes, hyperlipidaemia and hyperphagia. Most importantly, the increased levels of 11βHSD1 activity in the fat of these mice are similar to those seen in obese subjects. Hepatic 11βHSD1 activity and plasma corticosterone levels were normal, however, hepatic portal vein levels of corticosterone were increased 3 fold and it is thought that this is the cause of the metabolic effects in liver.

Overall it is now clear that the complete metabolic syndrome can be mimicked in mice simply by overexpressing 11βHSD1 in fat alone at levels similar to those in obese man.

11βHSD1 tissue distribution is widespread and overlapping with that of the glucocorticoid receptor. Thus, 11βHSD1 inhibition could potentially oppose the effects of glucocorticoids in a number of physiological/pathological roles. 11βHSD1 is present in human skeletal muscle and glucocorticoid opposition to the anabolic effects of insulin on protein turnover and glucose metabolism are well documented (Whorwood C B et al. 2001; J. Clin. Endocrinol. Metab. 86, 2296-2308). Skeletal muscle must therefore be an important target for 11βHSD1 based therapy.

Glucocorticoids also decrease insulin secretion and this could exacerbate the effects of glucocorticoid induced insulin resistance. Pancreatic islets express 11βHSD1 and carbenoxolone can inhibit the effects of 11-dehydrocorticosterone on insulin release (Davani B et al. 2000; J. Biol. Chem. 275, 34841-34844). Thus in treatment of diabetes 11βHSD1 inhibitors may not only act at the tissue level on insulin resistance but also increase insulin secretion itself.

Skeletal development and bone function is also regulated by glucocorticoid action. 11βHSD1 is present in human bone osteoclasts and osteoblasts and treatment of healthy volunteers with carbenoxolone showed a decrease in bone resorption markers with no change in bone formation markers (Cooper M S et al 2000; Bone 27, 375-381). Inhibition of 11βHSD1 activity in bone could be used as a protective mechanism in treatment of osteoporosis.

Glucocorticoids may also be involved in diseases of the eye such as glaucoma. 11βHSD1 has been shown to affect intraocular pressure in man and inhibition of 11βHSD1 may be expected to alleviate the increased intraocular pressure associated with glaucoma (Rauz S et al. 2001; Investigative Opthalmology & Visual Science 42, 2037-2042).

There appears to be a convincing link between 11βHSD1 and the metabolic syndrome both in rodents and in humans. Evidence suggests that a drug which specifically inhibits 11βHSD1 in type 2 obese diabetic patients will lower blood glucose by reducing hepatic gluconeogenesis, reduce central obesity, improve the atherogenic lipoprotein phenotype, lower blood pressure and reduce insulin resistance. Insulin effects in muscle to will be enhanced and insulin secretion from the beta cells of the islet may also be increased.

Currently there are two main recognised definitions of metabolic syndrome.

1) The Adult Treatment Panel (ATP III 2001 JMA) definition of metabolic syndrome indicates that it is present if the patient has three or more of the following symptoms: Waist measuring at least 40 inches (102 cm) for men, 35 inches (88 cm) for women; Serum triglyceride levels of at least 150 mg/dl (1.69 mmol/l);

HDL cholesterol levels of less than 40 mg/dl (1.04 mmol/l) in men, less than 50 mg/dl (1.29 mmol/l) in women;

Blood pressure of at least 135/80 mm Hg; and/or Blood sugar (serum glucose) of at least 110 mg/dl (6.1 mmol/l).

2) The WHO consultation has recommended the following definition which does not imply causal relationships and is suggested as a working definition to be improved upon in due course:

The patient has at least one of the following conditions: glucose intolerance, impaired glucose tolerance (IGT) or diabetes mellitus and/or insulin resistance; together with two or more of the following:

Raised Arterial Pressure;

Raised plasma triglycerides

Central Obesity

Microalbuminuria

We have found that the compounds defined in the present invention, or a pharmaceutically-acceptable salt thereof, are effective 11βHSD1 inhibitors, and accordingly have value in the treatment of disease states associated with metabolic syndrome. We have also found that the compounds of the invention have improved properties, which would make them better candidates for use as pharmaceuticals. For example, in general the compounds of the invention have good oral bioavailability whilst retaining potency. Therefore this group of compounds would be expected to provide superior oral exposure at a lower dose and thereby be particularly suitable for use in the treatment or prevention of a disease or medical condition treatable by inhibiting 11βHSD1.

The compounds of the invention may also have superior potency and/or advantageous physical properties and/or favourable toxicity profiles and/or favourable metabolic profiles in comparison with other 11βHSD1 inhibitors known in the art. For example, in general the compounds of the present invention have acceptable free drug levels as measured by plasma protein binding experiments.

Accordingly there is provided a compound of formula (1):

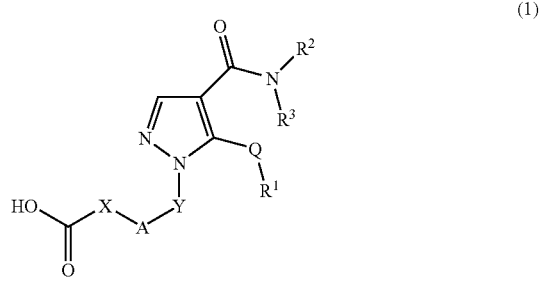

wherein:

Q is O, S or a single bond;

$R^1$ is $C_{1-6}$alkyl, $C_{2-6}$alkenyl, $C_{2-6}$alkynyl, $C_{3-7}$cycloalkyl, heterocyclyl, aryl$C_{1-3}$alkyl, heteroaryl$C_{1-3}$alkyl, $C_{3-7}$cycloalkyl$C_{1-3}$alkyl, $C_{3-7}$cycloalkyl$C_{2-3}$alkenyl or $C_{3-7}$cycloalkyl$C_{2-3}$alkynyl, [each of which is optionally substituted by 1, 2 or 3 substituents independently selected from $C_{1-3}$alkyl, hydroxy, halo, oxo, cyano, trifluoromethyl, $C_{1-3}$alkoxy, $C_{1-3}$alkylS(O)$_n$— (wherein n is 0, 1, 2 or 3), $R^5$CON($R^{5'}$)—, ($R^{5'}$)($R^{5''}$)NC(O)—, $R^{5'}$C(O)O—, $R^{5'}$OC(O)—, ($R^{5'}$)($R^{5''}$)NC(O)N($R^{5'''}$)—, $R^5$SO$_2$N($R^{5'}$)—, and ($R^{5'}$)($R^{5''}$)NSO$_2$— (wherein $R^5$ is $C_{1-3}$alkyl optionally substituted by 1, 2 or 3 substituents selected from hydroxyl, halo or cyano; and $R^{5'}$ and $R^{5''}$ are independently selected from hydrogen and $C_{1-3}$alkyl optionally substituted by 1, 2 or 3 substituents independently selected from hydroxyl, halo, $C_{1-3}$alkoxy, carboxy and cyano or $R^{5'}$ and $R^{5''}$ together with the nitrogen atom to which they are attached form a 4-7 membered saturated ring)];

$R^2$ is selected from heterocyclyl, $C_{3-7}$cycloalkyl(CH$_2$)$_m$—, and $C_{6-12}$polycycloalkyl(CH$_2$)$_m$— (wherein m is 0, 1 or 2 and the rings are optionally substituted by 1, 2 or 3 substituents independently selected from $R^6$);

$R^3$ is selected from hydrogen, $C_{1-4}$alkyl $C_{3-5}$cycloalkyl and $C_{3-5}$cycloalkylmethyl (each of which is optionally substituted by 1, 2 or 3 fluoro atoms);

$R^2$ and $R^3$ together with the nitrogen atom to which they are attached form a saturated mono, bicyclic or bridged ring system optionally containing 1 or 2 additional ring heteroatoms selected from nitrogen, oxygen and sulphur and which is optionally fused to a saturated, partially saturated or unsaturated monocyclic ring wherein the resulting ring system is optionally substituted by 1, 2, or 3 substituents independently selected from $R^7$;

$R^6$ and $R^7$ are independently selected from hydroxyl, halo, oxo, carboxy, cyano, trifluoromethyl, $R^9$, $R^9$O—, $R^9$CO—, $R^9$C(O)O—, $R^9$CON($R^{9'}$)—, ($R^{9'}$)($R^{9''}$)NC(O)—, ($R^{9'}$)($R^{9''}$)N—, $R^9$S(O)$_a$— wherein a is 0 to 2, $R^9$OC(O)—, ($R^{9'}$)($R^{9''}$)NSO$_2$—, $R^9$SO$_2$N($R^{9'}$)—, ($R^{9'}$)($R^{9''}$)NC(O)N($R^{9'''}$)—, phenyl and heteroaryl [wherein the phenyl and heteroaryl groups are optionally fused to a phenyl, heteroaryl or a saturated or partially-saturated 5- or 6-membered ring optionally containing 1, 2 or 3 heteroatoms independently selected from nitrogen, oxygen and sulphur and the resulting ring system is optionally substituted by 1, 2 or 3 substituents independently selected from $C_{1-4}$alkyl, hydroxyl, cyano, trifluoromethyl, trifluoromethoxy, halo, $C_{1-4}$alkoxy, $C_{1-4}$alkoxy$C_{1-4}$alkyl, amino, N—$C_{1-4}$alkylamino, di-N,N—($C_{1-4}$alkyl)amino, N—$C_{1-4}$alkylcarbamoyl, di-N,N—($C_{1-4}$alkyl)carbamoyl, $C_{1-4}$alkylS(O)$_r$—, $C_{1-4}$alkylS(O)$_r$$C_{1-4}$alkyl (wherein r is 0, 1 or 2)];

$R^9$ is independently selected from $C_{1-3}$alkyl optionally substituted by hydroxyl, halo, $C_{1-4}$alkoxy, carboxy or cyano;

$R^{9'}$, $R^{9''}$ and $R^{9'''}$ are independently selected from hydrogen and $C_{1-3}$alkyl optionally substituted by 1, 2, or 3 substituents independently selected from hydroxyl, halo, $C_{1-4}$alkoxy, carboxy and cyano);

A is a phenyl or heteroaryl ring (the phenyl or heteroaryl ring being optionally substituted on ring carbon atoms by 1, 2 or 3 $R^{10}$ groups and on an available ring nitrogen in a heteroaryl group by $R^{11}$);

$R^{10}$ is independently selected from $C_{1-4}$alkyl, hydroxyl, cyano, trifluoromethyl, trifluoromethoxy, halo, $C_{1-4}$alkoxy, $C_{1-4}$alkoxy$C_{1-4}$alkyl, amino, N—$C_{1-4}$alkylamino, di-N,N—($C_{1-4}$alkyl)amino, N—$C_{1-4}$alkylcarbamoyl, di-N,N—($C_{1-4}$alkyl)carbamoyl, $C_{1-4}$alkylS(O)$_s$—, $C_{1-4}$alkylS(O)$_s$$C_{1-4}$alkyl (wherein s is 0, 1 or 2)];

$R^{11}$ is independently $C_{1-3}$alkyl optionally substituted by 1, 2 or 3 fluoro atoms;

X is a direct bond, $C_{3-4}$cycloalkandiyl, $C_{3-4}$cycloalkanylidene, —C($R^{12}$)($R^{13}$)—, —C($R^{12}$)($R^{13}$)C($R^{14}$)($R^{15}$)—, —CH$_2$O— or —CH$_2$S(O)$_t$— (wherein t is 0, 1 or 2):

Y is a direct bond, $C_{3-4}$cycloalkandiyl, $C_{3-4}$cycloalkanylidene, —C($R^{16}$)($R^{17}$)— or —C($R^{18}$)($R^{19}$)C($R^{20}$)($R^{21}$)—;

wherein $R^{12}$, $R^{13}$, $R^{14}$, $R^{15}$, $R^{16}$, $R^{17}$, $R^{18}$, $R^{19}$, $R^{20}$ and $R^{21}$ are independently selected from hydrogen and methyl;

or a pharmaceutically-acceptable salt thereof.

In this specification the term "alkyl" includes both straight and branched chain alkyl groups but references to individual alkyl groups such as "propyl" are specific for the straight chain version only. For example, "$C_{1-4}$alkyl" includes propyl, isopropyl and t-butyl. However, references to individual alkyl groups such as 'propyl' are specific for the straight chain version only and references to individual branched chain alkyl groups such as 'isopropyl' are specific for the branched chain version only. A similar convention applies to other radicals therefore "$C_{1-4}$alkoxy$C_{1-4}$alkyl" would include 1-($C_{1-4}$alkoxy)propyl, 2-($C_{1-4}$alkoxy)ethyl and 3-($C_{1-4}$alkoxy)butyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A 4-7 membered saturated ring (for example formed between $R^{5'}$ and $R^{5'''}$ and the nitrogen atom to which they are attached) is a monocyclic ring containing the nitrogen atom as the only ring atom.

"Heteroaryl", unless otherwise specified, is a totally unsaturated, monocyclic ring containing 5 or 6 atoms of which at least 1, 2 or 3 ring atoms are independently chosen from nitrogen, sulphur or oxygen, which may, unless otherwise specified, be carbon-linked. A ring nitrogen atom may be optionally oxidised to form the corresponding N-oxide. Examples and suitable values of the term "heteroaryl" are thienyl, furyl, thiazolyl, pyrazolyl, isoxazolyl, imidazolyl, pyrrolyl, thiadiazolyl, isothiazolyl, triazolyl, pyrimidyl, pyrazinyl, pyridazinyl and pyridyl. Particularly "heteroaryl" refers to thienyl, furyl, thiazolyl, pyridyl, imidazolyl or pyrazolyl.

"Heterocycyl" is a 4-7 saturated, monocyclic ring having 1-3 ring heteroatoms selected from nitrogen, oxygen and sulphur. The ring sulphur may be optionally oxidised to SO$_2$.

A $C_{3-7}$cycloalkyl ring is a saturated carbon ring containing from 3 to 7 ring atoms.

A $C_{3-4}$cycloalkandiyl ring is a saturated carbon ring containing 3 or 4 ring atoms. It is a diradical with the radicals on different ring carbon atoms.

A $C_{3-4}$cycloalkanylidene ring is a saturated carbon ring containing 3 or 4 ring atoms. It is a diradical with the radicals on the same ring carbon atom.

A polycycloalkyl ring is a ring system in which either at least 2 rings are fused together or in which 2 ring have one ring atom in common (spiro).

A "saturated mono, bicyclic or bridged ring system optionally containing 1 or 2 additional ring heteroatoms selected from nitrogen, oxygen and sulphur", unless otherwise specified contains 4-14 ring atoms. Particularly a mono ring contains 4-7 ring atoms, a bicyclic ring 6-14 ring atoms and a bridged ring system 6-14 ring atoms. Examples of mono rings include piperidinyl, piperazinyl and morpholinyl. Examples of bicyclic rings include decalin and 2,3,3a,4,5,6,7,7a-octahydro-1H-indene.

Bridged ring systems are ring systems in which there are two or more bonds common to two or more constituent rings. Examples of bridged ring systems include 1,3,3-trimethyl-6-azabicyclo[3.2.1]octane, 2-aza-bicyclo[2.2.1]heptane and 7-azabicyclo(2,2,1)heptane, 1- and 2-adamantanyl.

A "saturated, partially saturated or unsaturated monocyclic ring" is, unless otherwise specified, a 4-7 membered ring. Examples include, cyclopropyl, cyclobutyl, cyclopentyl, cyclopentenyl, cyclohexyl, cyclohexenyl and phenyl.

Examples of a "saturated or partially-saturated 5- or 6-membered ring optionally containing 1, 2 or 3 heteroatoms independently selected from nitrogen, oxygen and sulphur" include piperidinyl, piperazinyl and morpholinyl.

Examples of "$C_{1-4}$alkoxy" include methoxy, ethoxy and propoxy. Examples of "$C_{1-4}$alkoxy$C_{1-4}$alkyl" include methoxymethyl, ethoxymethyl, propoxymethyl, 2-methoxyethyl, 2-ethoxyethyl and 2-propoxyethyl. Examples of "$C_{1-4}$alkylS(O)$_n$, wherein n is 0 to 2" include methylthio, ethylthio, methylsulphinyl, ethylsulphinyl, mesyl and ethylsulphonyl. Examples of "$C_{1-4}$alkylS(O)$_q$$C_{1-4}$alkyl" wherein q is 0 to 2" include methylthio, ethylthio, methylsulphinyl, ethylsulphinyl, mesyl, ethylsulphonyl, methylthiomethyl, ethylthioethyl, methylsulphinylmethyl, ethylsulphinylmethyl, mesylmethyl and ethylsulphonylmethyl. Examples of "$C_{1-4}$alkanoyl" include propionyl and acetyl. Examples of "N—($C_{1-4}$alkyl)amino" include methylamino and ethylamino. Examples of "N,N—($C_{1-4}$alkyl)$_2$-amino" include N,N-dimethylamino, N,N-diethylamino and N-ethyl-N-methylamino Examples of "$C_{2-4}$alkenyl" are vinyl, allyl and 1-propenyl. Examples of "$C_{2-4}$alkynyl" are ethynyl, 1-propynyl and 2-propynyl. Examples of "N—($C_{1-4}$alkyl)carbamoyl" are methylaminocarbonyl and ethylaminocarbonyl. Examples of "N,N—($C_{1-4}$alkyl)$_2$-carbamoyl" are dimethylaminocarbonyl and methylethylaminocarbonyl. Examples of "$C_{3-7}$cycloalkyl$C_{1-3}$alkalkyl" include cyclopropylmethyl, 2-cyclopropylethyl, cyclobutylmethyl, cyclopentylmethyl and cyclohexylmethyl. Examples of "$C_{3-7}$cycloalkyl$C_{2-3}$alkalkenyl" include 2-cyclopropylethenyl, 2-cyclopentylethenyl and 2-cyclohexylethenyl. Examples of "$C_{3-7}$cycloalkyl$C_{2-3}$alkalkynyl" include 2-cyclopropylethynyl, 2-cyclopentylethynyl and 2-cyclohexylethynyl.

Examples of "$C_{3-7}$cycloalkyl$(CH_2)_m$—" include cyclopropymethyl, 2-cyclopropylethyl, cyclobutylmethyl, cyclopentylmethyl and cyclohexylmethyl. Examples of $C_{6-12}$polycycloalkyl$(CH_2)_m$— include norbornyl bicyclo[2.2.2]octane$(CH_2)_m$—, bicyclo[3.2.1]octane$(CH_2)_m$— and 1- and 2-adamantanyl$(CH_2)_m$—.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Some compounds of the formula (1) may have chiral centres and/or geometric isomeric centres (E- and Z-isomers), and it is to be understood that the invention encompasses all such optical, diastereoisomers and geometric isomers that possess 11βHSD1 inhibitory activity.

The invention relates to any and all tautomeric forms of the compounds of the formula (1) that possess 11βHSD1 inhibitory activity.

It is also to be understood that certain compounds of the formula (1) can exist in solvated as well as unsolvated forms such as, for example, hydrated forms. It is to be understood that the invention encompasses all such solvated forms, which possess 11βHSD1 inhibitory activity.

The invention also relates to in vivo hydrolysable esters of a compound of the formula (I). In vivo hydrolysable esters are those esters that are broken down in the animal body to produce the parent carboxylic acid.

In one embodiment of the invention are provided compounds of formula (1). In an alternative embodiment are provided pharmaceutically-acceptable salts of compounds of formula (1).

In one aspect of the invention, there is provided a compound of the formula (Ia):

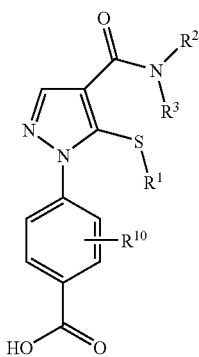

(1a)

wherein $R^1$, $R^2$ and $R^3$ are as hereinabove defined and $R^{10}$ is selected from hydrogen, $C_{1-4}$alkyl, trifluoromethyl, $C_{1-4}$alkoxy and $C_{1-4}$alkylS—. In another aspect $R^{10}$ is selected from hydrogen, methyl, trifluoromethyl, methoxy and methylthio. In another aspect $R^{10}$ is hydrogen.

In another aspect of the invention, there is provided a compound of the formula (Ib):

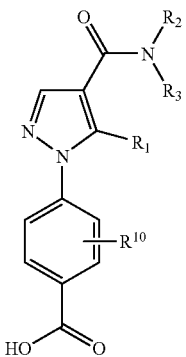

(1b)

wherein $R^1$, $R^2$ and $R^3$ are as hereinabove defined and $R^{10}$ is selected from hydrogen, $C_{1-4}$alkyl, trifluoromethyl, $C_{1-4}$alkoxy and $C_{1-4}$alkylS—. In another aspect $R^{10}$ is selected from hydrogen, methyl, trifluoromethyl, methoxy and methylthio. In another aspect $R^{10}$ is hydrogen.

Particular values of variable groups are as follows. Such values may be used where appropriate with any of the definitions, claims or embodiments defined hereinbefore or hereinafter, for compounds of formula (1). The definitions of $R^1$, $R^2$ and $R^3$ and variables within those groups may be used for the compound of formula (Ia):

Definition of Q a) In one aspect, the invention relates to a compound of the formula (I) as hereinabove defined wherein Q is O.

b) In another aspect Q is S.

c) In another aspect Q is a single bond.

Definition of $R^1$ a) In one aspect $R^1$ is $C_{3-6}$cycloalkyl optionally substituted by 1, 2 or 3 substituents independently selected from $C_{1-3}$alkyl, hydroxy, halo, oxo, cyano, fluoro, trifluoromethyl and $C_{1-3}$alkoxy.

b) In another aspect $R^1$ is $C_{3-6}$cycloalkyl.

c) In another aspect $R^1$ is $C_{3-6}$cycloalkyl$C_{1-2}$alkyl optionally substituted by 1, 2 or 3 substituents independently selected from $C_{1-3}$alkyl, hydroxy, halo, oxo, cyano, fluoro, trifluoromethyl and $C_{1-3}$alkoxy.

d) In another aspect $R^1$ is $C_{3-4}$cycloalkyl$C_{1-2}$alkyl.

e) In another aspect $R^1$ is $C_{1-4}$alkyl optionally substituted by 1, 2 or 3 substituents independently selected from $C_{1-3}$alkyl, hydroxy, halo, oxo, cyano, trifluoromethyl and $C_{1-3}$alkoxy.

f) In another aspect $R^1$ is $C_{1-4}$alkyl.

g) In another aspect $R^1$ is propyl optionally substituted by 1 or 2 substituents independently selected from $C_{1-3}$alkyl, hydroxy, halo, oxo, cyano, trifluoromethyl and $C_{1-3}$alkoxy.

h) In another aspect $R^1$ is propyl.

Definition of $R^2$ a) In one aspect, $R^2$ is selected from $C_{3-7}$cycloalkyl$(CH_2)_m$—, and $C_{6-12}$polycycloalkyl$(CH_2)_m$— (wherein m is 0, 1 or 2 and the rings are optionally substituted by 1, 2 or 3 substituents independently selected from $R^6$) wherein m is 0, 1 or 2.

b) In another aspect, $R^2$ is selected from $C_{5-7}$cycloalkyl$(CH_2)_m$— and $C_{8-12}$polycycloalkyl$(CH_2)_m$— (wherein the rings are optionally substituted by 1, 2 or 3 substituents independently selected from $R^6$) and wherein m is 0, 1 or 2.

c) In another aspect, $R^2$ is selected from $C_{5-7}$cycloalkyl$(CH_2)_m$—, $C_{7-10}$bicycloalkyl$(CH_2)_m$— and $C_{10}$tricycloalkyl$(CH_2)_m$— (wherein the cycloalkyl, bicycloalkyl and tricycloalkyl rings are optionally substituted by 1, 2 or 3 substituents to independently selected from $R^6$) and wherein m is 0, 1 or 2.

d) In yet another aspect, $R^2$ is selected from $C_{5-7}$cycloalkyl$(CH_2)_m$—, $C_{7-10}$bicycloalkyl$(CH_2)_m$— and adamantyl (wherein the cycloalkyl, bicycloalkyl and tricycloalkyl rings are optionally substituted by 1, 2 or 3 substituents independently selected from $R^6$) and wherein m is 0, 1 or 2.

Definition of m a) In one aspect, m is 0 or 1.

Definition of $R^3$ a) In one aspect, $R^3$ is $C_{1-4}$alkyl.

b) In another aspect, $R^3$ is hydrogen, methyl or ethyl.

c) In another aspect, $R^3$ is hydrogen.

d) In another aspect, $R^3$ is methyl.

e) In another aspect, $R^3$ is ethyl.

f) In another aspect, $R^3$ is cyclopropyl.

Definition of $R^2$ and $R^3$ Together a) In another aspect, $R^2$ and $R^3$ together with the nitrogen atom to which they are attached form a saturated 5 or 6-membered mono, 6-12 membered bicyclic or 6-12 membered bridged ring system optionally containing 1 or 2 additional ring heteroatoms selected from nitrogen, oxygen and sulphur and which is optionally fused to a saturated, partially-saturated or aryl monocyclic ring wherein the resulting ring system is optionally substituted by 1, 2, or 3 substituents independently selected from $R^7$.

Definition of $R^6$ a) In one aspect, $R^6$ is independently selected from hydroxyl, $R^9O$—, $R^9CO$— and $R^9C(O)O$— wherein $R^9$ is as hereinabove defined.

b) In another aspect, $R^6$ is independently selected from hydroxyl, $R^9O$—, $R^9CO$— and $R^9C(O)O$— wherein $R^9$ is $C_{1-3}$alkyl optionally substituted by $C_{1-4}$alkoxy or carboxy.

c) In another aspect, $R^6$ is independently selected from $R^9CON(R^{9'})$—, $R^9SO_2N(R^{9'})$— and $(R^{9'})(R^{9''})NC(O)N(R^{9'''})$—;

wherein $R^9$ is as hereinabove defined.

d) In another aspect, $R^6$ is independently selected from $R^9CON(R^{9'})$—, $R^9SO_2N(R^{9'})$— and $(R^{9'})(R^{9''})NC(O)N(R^{9'''})$—;

$R^9$ is $C_{1-3}$alkyl optionally substituted by $C_{1-4}$alkoxy or carboxy;

$R^{9'}$, $R^{9''}$ and $R^{9'''}$ are independently selected from hydrogen and $C_{1-3}$alkyl optionally substituted by $C_{1-4}$alkoxy or carboxy).

e) In another aspect, $R^6$ is independently selected from $(R^{9'})(R^{9'''})NC(O)$— and $(R^{9'})(R^{9''})N$—;

wherein $R^{9'}$ and $R^{9'''}$ are as hereinabove defined.

f) In another aspect, $R^6$ is independently selected from $(R^{9'})(R^{9'''})NC(O)$— and $(R^{9'})(R^{9''})N$—;

wherein $R^{9'}$ and $R^{9'''}$ are independently selected from hydrogen and $C_{1-3}$alkyl optionally substituted by $C_{1-4}$alkoxy or carboxy.

g) In one aspect $R^6$ is selected from methyl, trifluoromethyl, chloro, fluoro, bromo, methoxy, ethoxy, trifluormethoxy, methanesulfonyl, ethanesulfonyl, methylthio, ethylthio, amino, N-methylamino, N-ethylamino, N-propylamino, N,N-dimethylamino, N,N-methylethylamino or N,N-diethylamino.

h) In another aspect, $R^6$ is optionally substituted phenyl, pyridyl or pyrimidyl.

i) In another aspect, $R^6$ is optionally substituted pyrid-2-yl, pyrid-3-yl or pyrid-4-yl.

Definition of $R^7$ a) In another aspect, $R^7$ is independently selected from hydroxyl, halo, oxo, cyano, trifluoromethyl, $R^9$ and $R^9O$— (wherein $R^9$ is as hereinabove defined).

b) In another aspect, $R^7$ is independently selected from hydroxyl, halo, trifluoromethyl, $R^9$ and $R^9O$— (wherein $R^9$ is as hereinabove defined).

Definition of $R^9$ a) In one aspect, $R^9$ is independently selected from $C_{1-3}$alkyl.

Definition of $R^{9'}$, $R^{9''}$ and $R^{9'''}$ a) In one aspect, $R^{9'}$, $R^{9''}$ and $R^{9'''}$ are independently selected from hydrogen and $C_{1-3}$alkyl.

Definition of Y a) In one aspect, Y is independently selected from direct bond, —$CH_2$— and —$CH_2CH_2$—.

b) In one aspect, Y is independently selected from —$CH_2$— and —$CH_2CH_2$—.

c) In another aspect Y is a direct bond.

Definition of A a) In one aspect A is phenyl optionally substituted by $R^{10}$.

b) In another aspect A is heteroaryl optionally substituted by $R^{10}$ and $R^{11}$.

c) In another aspect A is thienyl optionally substituted by $R^{10}$ and $R^{11}$.

d) In another aspect A is pyridyl optionally substituted by $R^{10}$ and $R^{11}$.

e) In another aspect A is phen-1,4-diyl

Definition of $R^{10}$ a) In one aspect, $R^{10}$ is independently selected from $C_{1-4}$alkyl, hydroxyl, cyano, trifluoromethyl, trifluoromethoxy, difluoromethoxy, halo, $C_{1-4}$alkoxy and $C_{1-4}$alkoxy$C_{1-4}$alkyl.

b) In another aspect, $R^{10}$ is independently selected from methyl, ethyl, hydroxyl, cyano, trifluoromethyl, trifluoromethoxy, difluoromethoxy, halo, methoxy, ethoxy, methoxymethyl and ethoxymethyl.

c) In another aspect, $R^{10}$ is independently selected from methyl, ethyl, cyano, trifluoromethyl, trifluoromethoxy, difluoromethoxy, halo, methoxy, ethoxy.

Definition of $R^{11}$ a) In one aspect, $R^{11}$, is independently selected from $C_{1-3}$alkyl, trifluoromethyl and difluoromethyl.

b) In one aspect, $R^{11}$, is independently selected from methyl, ethyl, trifluoromethyl and difluoromethyl.

Definition of X a) In one aspect, X is independently selected from direct bond, —$CH_2$—, —CHMe-, —$CMe_2$-, —$CH_2CH_2$—, —$CH_2O$— and —$CH2S$—.

b) In one aspect, X is independently selected from —$CH_2$—, —CHMe-, —$CMe_2$-, —$CH_2CH_2$—, —$CH_2O$— and —$CH_2S$—.

c) In another aspect X is independently selected from cyclopropanylidene, cyclobutanylidene, cyclopropane-1,2-diyl and cyclobutan-1,2-diyl.

d) In another aspect X is a direct bond.

In one aspect, $R^{12}$, $R^{13}$, $R^{14}$, $R^{15}$, $R^{16}$, $R^{17}$, $R^{18}$, $R^{19}$, $R^{20}$ and $R^{21}$ are hydrogen.

In one aspect $R^1$ is optionally substituted by 0 substituents.

In one aspect $R^1$ is optionally substituted by 1 substituent.

In one aspect $R^1$ is optionally substituted by 2 substituents.

In one aspect $R^1$ is optionally substituted by 3 substituents.

In one aspect $R^2$ is optionally substituted by 0 substituents.

In one aspect $R^2$ is optionally substituted by 1 substituent.

In one aspect $R^2$ is optionally substituted by 2 substituents.

In one aspect $R^2$ is optionally substituted by 3 substituents.

In one aspect $R^3$ is optionally substituted by 0 substituents.

In one aspect $R^3$ is optionally substituted by 1 substituent.

In one aspect $R^3$ is optionally substituted by 2 substituents.

In one aspect $R^3$ is optionally substituted by 3 substituents.

In one aspect the group formed by $R^2$ and $R^3$ together is optionally substituted by 0 substituents.

In one aspect the group formed by $R^2$ and $R^3$ together is optionally substituted by 1 substituent.

In one aspect the group formed by $R^2$ and $R^3$ together is optionally substituted by 2 substituents.

In one aspect the group formed by $R^2$ and $R^3$ together is optionally substituted by 3 substituents.

In one aspect A is optionally substituted by 0 substituents.

In one aspect A is optionally substituted by 1 substituent.

In one aspect A is optionally substituted by 2 substituents.

In one aspect A is optionally substituted by 3 substituents.

In one aspect the phenyl and heteroaryl groups in $R^6$ and $R^7$ are independently optionally substituted by 0 substituents.

In one aspect the phenyl and heteroaryl groups in $R^6$ and $R^7$ are independently optionally substituted by 1 substituent.

In one aspect the phenyl and heteroaryl groups in $R^6$ and $R^7$ are independently are optionally substituted by 2 substituents.

In one aspect the phenyl and heteroaryl groups in $R^6$ and $R^7$ are independently are optionally substituted by 3 substituents.

In one aspect of the invention Q is a direct bond and X is a direct bond.

Particular classes of compounds of the present invention are disclosed in Table A using combinations of the definitions described hereinabove. For example, 'a' in the column headed $R^2$ in the table refers to definition (a) given for $R^2$ hereinabove and 'I' refers to the first definition given for the variables in the compound of formula (I) at the beginning of the description. $R^6$ and $R^7$ are optional substituents on $R^2$ and the group formed by $R^2$ and $R^3$ together. $R^2$ and $R^3$ may of course be unsubstituted or substituted by the values listed for $R^6$ and $R^7$. A "-" in the column for R6 and R7 means that the relevant $R^2$ group or the group formed by $R^2$ and $R^3$ together is unsubstituted. Table A refers to compounds of the formula (1).

TABLE A

| Class | Q | $R^1$ | $R^2$ | $R^6$ | $R^3$ | $R^2$ and $R^3$ together | $R^7$ | X | Y | A |
|---|---|---|---|---|---|---|---|---|---|---|
| 1 | I | I | a | I | I | — | — | I | I | I |
| 2 | I | a | — | — | — | I | I | I | I | I |
| 3 | I | b | a | I | I | — | — | a | a | a |
| 4 | a | I | — | — | — | I | I | a | a | a |
| 5 | c | I | a | I | I | — | — | a | a | a |
| 6 | b | c | — | — | — | a | g | d | c | a |
| 7 | b | d | b | g | b | — | — | d | c | b |
| 8 | b | e | c | g | b | — | — | d | c | a |
| 9 | b | f | d | — | c | — | — | d | c | e |
| 10 | b | h | d | — | c | — | — | d | c | e |

Particular classes of compounds of the formula (1a) are disclosed in Table B using combinations of the definitions described hereinabove in a similar manner as for Table A.

TABLE B

| Class | $R^1$ | $R^2$ | $R^6$ | $R^3$ | $R^2$ and $R^3$ together | $R^7$ |
|---|---|---|---|---|---|---|
| 1a | I | I | I | I | — | — |
| 2a | a | — | — | — | I | I |
| 3a | b | a | I | I | — | — |
| 4a | I | — | — | — | I | I |
| 5a | I | a | I | I | — | — |
| 6a | c | — | — | — | a | g |
| 7a | d | b | g | b | — | — |
| 8a | e | c | g | c | — | — |
| 9a | f | d | — | — | — | — |
| 10a | h | d | — | — | — | — |

Particular classes of compounds of the formula (1b) are disclosed in Table B using combinations of the definitions described hereinabove in a similar manner as for Table A.

TABLE C

| Class | $R^1$ | $R^2$ | $R^6$ | $R^3$ | $R^2$ and $R^3$ together | $R^7$ |
|---|---|---|---|---|---|---|
| 1b | I | I | I | I | — | — |
| 2b | a | — | — | — | I | I |

TABLE C-continued

| Class | $R^1$ | $R^2$ | $R^6$ | $R^3$ | $R^2$ and $R^3$ together | $R^7$ |
|---|---|---|---|---|---|---|
| 3b | b | a | I | I | — | — |
| 4b | I | — | — | — | I | I |
| 5b | I | a | I | I | — | — |
| 6b | c | — | — | — | a | g |
| 7b | d | b | g | b | — | — |
| 8b | e | c | g | c | — | — |
| 9b | f | d | — | — | — | — |
| 10b | h | d | — | — | — | — |

A further class of compounds is of formula (1) wherein:

Q is a single bond;

$R^1$ is $C_{1-6}$alkyl, $C_{2-6}$alkenyl, $C_{2-6}$alkynyl, $C_{3-7}$cycloalkyl, heterocyclyl, aryl$C_{1-3}$alkyl, heteroaryl$C_{1-3}$alkyl, $C_{3-7}$cycloalkyl$C_{1-3}$alkyl, $C_{3-7}$cycloalkyl$C_{2-3}$alkenyl or $C_{3-7}$cycloalkyl$C_{2-3}$alkynyl, [each of which is optionally substituted by 1, 2 or 3 substituents independently selected from $C_{1-3}$alkyl, hydroxy, halo, oxo, cyano, trifluoromethyl, $C_{1-3}$alkoxy, $C_{1-3}$alkylS(O)$_n$— (wherein n is 0, 1, 2 or 3), $R^5$CON($R^{5'}$)—, ($R^{5'}$)($R^{5''}$)NC(O)—, $R^{5'}$C(O)O—, $R^{5'}$OC(O)—, ($R^{5'}$)($R^{5''}$)NC(O)N($R^{5'''}$)—, $R^5$SO$_2$N($R^{5'}$)—, and ($R^{5'}$)($R^{5''}$)NSO$_2$— (wherein $R^5$ is $C_{1-3}$alkyl optionally substituted by 1, 2 or 3 substituents selected from hydroxyl, halo or cyano; and $R^{5'}$ and $R^{5'''}$ are independently selected from hydrogen and $C_{1-3}$alkyl optionally substituted by 1, 2 or 3 substituents independently selected from hydroxyl, halo, $C_{1-3}$alkoxy, carboxy and cyano or $R^{5'}$ and $R^{5'''}$ together with the nitrogen atom to which they are attached form a 4-7 membered saturated ring)];

$R^2$ is selected from heterocyclyl, $C_{3-7}$cycloalkyl(CH$_2$)$_m$—, and $C_{6-12}$polycycloalkyl(CH$_2$)$_m$— (wherein m is 0, 1 or 2 and the rings are optionally substituted by 1, 2 or 3 substituents independently selected from $R^6$);

$R^3$ is selected from hydrogen, $C_{1-4}$alkyl $C_{3-5}$cycloalkyl and $C_{3-5}$cycloalkylmethyl (each of which is optionally substituted by 1, 2 or 3 fluoro atoms);

$R^2$ and $R^3$ together with the nitrogen atom to which they are attached form a saturated mono, bicyclic or bridged ring system optionally containing 1 or 2 additional ring heteroatoms selected from nitrogen, oxygen and sulphur and which is optionally fused to a saturated, partially saturated or unsaturated monocyclic ring wherein the resulting ring system is optionally substituted by 1, 2, or 3 substituents independently selected from $R^7$;

$R^6$ and $R^7$ are independently selected from hydroxyl, halo, oxo, carboxy, cyano, trifluoromethyl, $R^9$, $R^{9O}$—, $R^9$CO—, $R^9$C(O)O—, $R^9$CON($R^{9'}$)—, ($R^{9'}$)($R^{9''}$)NC(O)—, ($R^{9'}$)($R^{9''}$)N—, $R^9$S(O)$_a$ wherein a is 0 to 2, $R^9$OC(O)—, ($R^{9'}$)($R^{9''}$)NSO$_2$—, $R^9$SO$_2$N($R^{9''}$)—, ($R^{9'}$)($R^{9''}$)NC(O)N($R^{9'''}$)—, phenyl and heteroaryl [wherein the phenyl and heteroaryl groups are optionally fused to a phenyl, heteroaryl or a saturated or partially-saturated 5- or 6-membered ring optionally containing 1, 2 or 3 heteroatoms independently selected from nitrogen, oxygen and sulphur and the resulting ring system is optionally substituted by 1, 2 or 3 substituents independently selected from $C_{1-4}$alkyl, hydroxyl, cyano, trifluoromethyl, trifluoromethoxy, halo, $C_{1-4}$alkoxy, $C_{1-4}$alkoxy$C_{1-4}$alkyl, amino, N—$C_{1-4}$alkylamino, di-N,N—($C_{1-4}$alkyl)amino, N—$C_{1-4}$alkylcarbamoyl, di-N,N—($C_{1-4}$alkyl)carbamoyl, $C_{1-4}$alkylS(O)$_r$—, $C_{1-4}$alkylS(O)$_r$$C_{1-4}$alkyl (wherein r is 0, 1 or 2)];

$R^9$ is independently selected from $C_{1-3}$alkyl optionally substituted by hydroxyl, halo, $C_{1-4}$alkoxy, carboxy or cyano;

$R^{9'}$, $R^{9''}$ and $R^{9'''}$ are independently selected from hydrogen and $C_{1-3}$alkyl optionally substituted by 1, 2, or 3 substituents independently selected from hydroxyl, halo, $C_{1-4}$alkoxy, carboxy and cyano);

A is a phenyl or heteroaryl ring (the phenyl or heteroaryl ring being optionally substituted on ring carbon atoms by 1, 2 or 3 $R^{10}$ groups and on an available ring nitrogen in a heteroaryl group by $R^{11}$);

$R^{10}$ is independently selected from $C_{1-4}$alkyl, hydroxyl, cyano, trifluoromethyl, trifluoromethoxy, halo, $C_{1-4}$alkoxy, $C_{1-4}$alkoxy$C_{1-4}$alkyl, amino, N—$C_{1-4}$alkylamino, di-N,N—($C_{1-4}$alkyl)amino, N—$C_{1-4}$alkylcarbamoyl, di-N,N—($C_{1-4}$alkyl)carbamoyl, $C_{1-4}$alkylS(O)$_s$—, $C_{1-4}$alkylS(O)$_s$$C_{1-4}$alkyl (wherein s is 0, 1 or 2)];

$R^{11}$ is independently $C_{1-3}$alkyl optionally substituted by 1, 2 or 3 fluoro atoms;

X is a direct bond, $C_{3-4}$cycloalkandiyl, $C_{3-4}$cycloalkanylidene, —C($R^{12}$)($R^{13}$)—, —C($R^{12}$)($R^{13}$)C($R^{14}$)($R^{15}$)—, —CH$_2$O— or —CH$_2$S(O)$_t$— (wherein t is 0, 1 or 2):

Y is a direct bond, $C_{3-4}$cycloalkandiyl, $C_{3-4}$cycloalkanylidene, —C($R^{16}$)($R^{17}$)— or —C($R^{18}$)($R^{19}$)C($R^{20}$)($R^{21}$)—;

wherein $R^{12}$, $R^{13}$, $R^{14}$, $R^{15}$, $R^{16}$, $R^{17}$, $R^{18}$, $R^{19}$, $R^{20}$ and $R^{21}$ are independently selected from hydrogen and methyl;

or a pharmaceutically-acceptable salt thereof.

Yet a further class of compound is of formula (1) wherein:

Q is a single bond;

$R^1$ is $C_{1-6}$alkyl, $C_{2-6}$alkenyl, $C_{2-6}$alkynyl, $C_{3-7}$cycloalkyl, heterocyclyl, aryl$C_{1-3}$alkyl, heteroaryl$C_{1-3}$alkyl, $C_{3-7}$cycloalkyl$C_{1-3}$alkyl, $C_{3-7}$cycloalkyl$C_{2-3}$alkenyl or $C_{3-7}$cycloalkyl$C_{2-3}$alkynyl, [each of which is optionally substituted by 1, 2 or 3 substituents independently selected from $C_{1-3}$alkyl, hydroxy, halo, oxo, cyano, trifluoromethyl, $C_{1-3}$alkoxy, $C_{1-3}$alkylS(O)$_n$— (wherein n is 0, 1, 2 or 3), $R^5$CON($R^{5'}$)—, ($R^{5'}$)($R^{5''}$)NC(O)—, $R^{5'}$C(O)O—, $R^{5'}$OC(O)—, ($R^{5'}$)($R^{5''}$)NC(O)N($R^{5'''}$)—, $R^5$SO$_2$N($R^{5'}$)—, and ($R^{5'}$)($R^{5''}$)NSO$_2$— (wherein $R^5$ is $C_{1-3}$alkyl optionally substituted by 1, 2 or 3 substituents selected from hydroxyl, halo or cyano; and $R^{5'}$ and $R^{5'''}$ are independently selected from hydrogen and $C_{1-3}$alkyl optionally substituted by 1, 2 or 3 substituents independently selected from hydroxyl, halo, $C_{1-3}$alkoxy, carboxy and cyano or $R^{5'}$ and $R^{5'''}$ together with the nitrogen atom to which they are attached form a 4-7 membered saturated ring)];

$R^2$ is selected from heterocyclyl, $C_{3-7}$cycloalkyl(CH$_2$)$_m$—, and $C_{6-12}$polycycloalkyl(CH$_2$)$_m$— (wherein m is 0, 1 or 2 and the rings are optionally substituted by 1, 2 or 3 substituents independently selected from $R^6$);

$R^3$ is selected from hydrogen, $C_{1-4}$alkyl $C_{3-5}$cycloalkyl and $C_{3-5}$cycloalkylmethyl (each of which is optionally substituted by 1, 2 or 3 fluoro atoms);

$R^2$ and $R^3$ together with the nitrogen atom to which they are attached form a saturated mono, bicyclic or bridged ring system optionally containing 1 or 2 additional ring heteroatoms selected from nitrogen, oxygen and sulphur and which is optionally fused to a saturated, partially saturated or unsaturated monocyclic ring wherein the resulting ring system is optionally substituted by 1, 2, or 3 substituents independently selected from $R^7$;

$R^6$ and $R^7$ are independently selected from hydroxyl, halo, oxo, carboxy, cyano, trifluoromethyl, $R^9$, $R^9O-$, $R^9CO-$, $R^9C(O)O-$, $R^9CON(R^{9'})-$, $(R^{9'})(R^{9''})NC(O)-$, $(R^{9'})(R^{9''})N-$, $R^9S(O)_a-$ wherein a is 0 to 2, $R^{9'}OC(O)-$, $(R^{9'})(R^{9''})NSO_2-$, $R^9SO_2N(R^{9''})-$, $(R^{9'})(R^{9''})NC(O)N(R^{9'''})-$, phenyl and heteroaryl [wherein the phenyl and heteroaryl groups are optionally fused to a phenyl, heteroaryl or a saturated or partially-saturated 5- or 6-membered ring optionally containing 1, 2 or 3 heteroatoms independently selected from nitrogen, oxygen and sulphur and the resulting ring system is optionally substituted by 1, 2 or 3 substituents independently selected from $C_{1-4}$alkyl, hydroxyl, cyano, trifluoromethyl, trifluoromethoxy, halo, $C_{1-4}$alkoxy, $C_{1-4}$alkoxy$C_{1-4}$alkyl, amino, N—$C_{1-4}$alkylamino, di-N,N—$(C_{1-4}$alkyl)amino, N—$C_{1-4}$alkylcarbamoyl, di-N,N—$(C_{1-4}$alkyl)carbamoyl, $C_{1-4}$alkylS(O)$_r$—, $C_{1-4}$alkylS(O)$_r$$C_{1-4}$alkyl (wherein r is 0, 1 or 2)];

$R^9$ is independently selected from $C_{1-3}$alkyl optionally substituted by hydroxyl, halo, $C_{1-4}$alkoxy, carboxy or cyano;

$R^{9'}$, $R^{9''}$ and $R^{9'''}$ are independently selected from hydrogen and $C_{1-3}$alkyl optionally substituted by 1, 2, or 3 substituents independently selected from hydroxyl, halo, $C_{1-4}$alkoxy, carboxy and cyano);

A is a phenyl or heteroaryl ring (the phenyl or heteroaryl ring being optionally substituted on ring carbon atoms by 1, 2 or 3 $R^{10}$ groups and on an available ring nitrogen in a heteroaryl group by $R^{11}$);

$R^{10}$ is independently selected from $C_{1-4}$alkyl, hydroxyl, cyano, trifluoromethyl, trifluoromethoxy, halo, $C_{1-4}$alkoxy, $C_{1-4}$alkoxy$C_{1-4}$alkyl, amino, N—$C_{1-4}$alkylamino, di-N,N—$(C_{1-4}$alkyl)amino, N—$C_{1-4}$alkylcarbamoyl, di-N,N—$(C_{1-4}$alkyl)carbamoyl, $C_{1-4}$alkylS(O)$_s$—, $C_{1-4}$alkylS(O)$_s$$C_{1-4}$alkyl (wherein s is 0, 1 or 2)];

$R^{11}$ is independently $C_{1-3}$alkyl optionally substituted by 1, 2 or 3 fluoro atoms;

either X is a direct bond and

Y is a direct bond, $C_{3-4}$cycloalkandiyl, $C_{3-4}$cycloalkanylidene, —C($R^{16}$)($R^{17}$)— or —C($R^{18}$)($R^{19}$)C($R^{20}$)($R^{21}$)—; or X is a direct bond, $C_{3-4}$cycloalkandiyl, $C_{3-4}$cycloalkanylidene, —C($R^{12}$)($R^{13}$)—, —C($R^{12}$)($R^{13}$)C($R^{14}$)($R^{15}$)—, —CH$_2$O— or —CH$_2$S(O)$_t$— (wherein t is 0, 1 or 2) and Y is a direct bond;

wherein $R^{12}$, $R^{13}$, $R^{14}$, $R^{15}$, $R^{16}$, $R^{17}$, $R^{18}$, $R^{19}$, $R^{20}$, and $R^{21}$ are independently selected from hydrogen and methyl;

or a pharmaceutically-acceptable salt thereof.

Yet a further class of compound is of formula (1) wherein:

Q is a single bond;

$R^1$ is $C_{1-6}$alkyl, $C_{2-6}$alkenyl, $C_{2-6}$alkynyl, $C_{3-7}$cycloalkyl, heterocyclyl, aryl$C_{1-3}$alkyl, heteroaryl$C_{1-3}$alkyl, $C_{3-7}$cycloalkyl$C_{1-3}$alkyl, $C_{3-7}$cycloalkyl$C_{2-3}$alkenyl or $C_{3-7}$cycloalkyl$C_{2-3}$alkynyl, [each of which is optionally substituted by 1, 2 or 3 substituents independently selected from $C_{1-3}$alkyl, hydroxy, halo, oxo, cyano, trifluoromethyl, $C_{1-3}$alkoxy, $C_{1-3}$alkylS(O)$_n$— (wherein n is 0, 1, 2 or 3), $R^5$CON($R^{5'}$)—, $(R^{5'})(R^{5'''})$NC(O)—, $R^5$C(O)O—, $R^5$OC(O)—, $(R^{5'})(R^{5''})$NC(O)N($R^{5'''}$)—, $R^5$SO$_2$N($R^{5''}$)—, and $(R^{5'})(R^{5''})$NSO$_2$— (wherein $R^5$ is $C_{1-3}$alkyl optionally substituted by 1, 2 or 3 substituents selected from hydroxyl, halo or cyano; and $R^{5'}$ and $R^{5''}$ are independently selected from hydrogen and $C_{1-3}$alkyl optionally substituted by 1, 2 or 3 substituents independently selected from hydroxyl, halo, $C_{1-3}$alkoxy, carboxy and cyano or $R^{5'}$ and $R^{5''}$ together with the nitrogen atom to which they are attached form a 4-7 membered saturated ring)];

$R^2$ is selected from heterocyclyl, $C_{3-7}$cycloalkyl(CH$_2$)$_m$—, and $C_{6-12}$polycycloalkyl(CH$_2$)$_m$— (wherein m is 0, 1 or 2 and the rings are optionally substituted by 1, 2 or 3 substituents independently selected from $R^6$);

$R^3$ is selected from hydrogen, $C_{1-4}$alkyl $C_{3-5}$cycloalkyl and $C_{3-5}$cycloalkylmethyl (each of which is optionally substituted by 1, 2 or 3 fluoro atoms);

$R^2$ and $R^3$ together with the nitrogen atom to which they are attached form a saturated mono, bicyclic or bridged ring system optionally containing 1 or 2 additional ring heteroatoms selected from nitrogen, oxygen and sulphur and which is optionally fused to a saturated, partially saturated or unsaturated monocyclic ring wherein the resulting ring system is optionally substituted by 1, 2 or 3 substituents independently selected from $R^7$;

$R^6$ and $R^7$ are independently selected from hydroxyl, halo, oxo, carboxy, cyano, trifluoromethyl, $R^9$, $R^9O-$, $R^9CO-$, $R^9C(O)O-$, $R^9CON(R^{9'})-$, $(R^{9'})(R^{9''})NC(O)-$, $(R^{9'})(R^{9''})N-$, $R^9S(O)_a-$ wherein a is 0 to 2, $R^{9'}OC(O)-$, $(R^{9'})(R^{9''})NSO_2-$, $R^9SO_2N(R^{9''})-$, $(R^{9'})(R^{9''})NC(O)N(R^{9'''})-$, phenyl and heteroaryl [wherein the phenyl and heteroaryl groups are optionally fused to a phenyl, heteroaryl or a saturated or partially-saturated 5- or 6-membered ring optionally containing 1, 2 or 3 heteroatoms independently selected from nitrogen, oxygen and sulphur and the resulting ring system is optionally substituted by 1, 2 or 3 substituents independently selected from $C_{1-4}$alkyl, hydroxyl, cyano, trifluoromethyl, trifluoromethoxy, halo, $C_{1-4}$alkoxy, $C_{1-4}$alkoxy$C_{1-4}$alkyl, amino, N—$C_{1-4}$alkylamino, di-N,N—$(C_{1-4}$alkyl)amino, N—$C_{1-4}$alkylcarbamoyl, di-N,N—$(C_{1-4}$alkyl)carbamoyl, $C_{1-4}$alkylS(O)$_r$—, $C_{1-4}$alkylS(O)$_r$$C_{1-4}$alkyl (wherein r is 0, 1 or 2)];

$R^9$ is independently selected from $C_{1-3}$alkyl optionally substituted by hydroxyl, halo, $C_{1-4}$alkoxy, carboxy or cyano;

$R^{9'}$, $R^{9''}$ and $R^{9'''}$ are independently selected from hydrogen and $C_{1-3}$alkyl optionally substituted by 1, 2, or 3 substituents independently selected from hydroxyl, halo, $C_{1-4}$alkoxy, carboxy and cyano);

A is a phenyl or heteroaryl ring (the phenyl or heteroaryl ring being optionally substituted on ring carbon atoms by 1, 2 or 3 $R^{10}$ groups and on an available ring nitrogen in a heteroaryl group by $R^{11}$);

$R^{10}$ is independently selected from $C_{1-4}$alkyl, hydroxyl, cyano, trifluoromethyl, trifluoromethoxy, halo, $C_{1-4}$alkoxy, $C_{1-4}$alkoxy$C_{1-4}$alkyl, amino, N—$C_{1-4}$alkylamino, di-N,N—$(C_{1-4}$alkyl)amino, N—$C_{1-4}$alkylcarbamoyl, di-N,N—$(C_{1-4}$alkyl)carbamoyl, $C_{1-4}$alkylS(O)$_s$—, $C_{1-4}$alkylS(O)$_s$ $C_{1-4}$alkyl (wherein s is 0, 1 or 2)];

$R^{11}$ is independently $C_{1-3}$alkyl optionally substituted by 1, 2 or 3 fluoro atoms;

X is a direct bond;

Y is a direct bond, $C_{3-4}$cycloalkandiyl, $C_{3-4}$cycloalkanylidene, —$C(R^{16})(R^{17})$— or —$C(R^{18})(R^{19})C(R^{20})(R^{21})$—; or X is a direct bond, $C_{3-4}$cycloalkandiyl, $C_{3-4}$cycloalkanylidene, —$C(R^{12})(R^{13})$—, —$C(R^{12})(R^{13})C(R^{14})(R^{15})$—, —$CH_2O$— or —$CH_2S(O)_t$— (wherein t is 0, 1 or 2) and Y is a direct bond;

wherein $R^{12}$, $R^{13}$, $R^{14}$, $R^{15}$, $R^{16}$, $R^{17}$, $R^{18}$, $R^{19}$, $R^{20}$ and $R^{21}$ are independently selected from hydrogen and methyl;

or a pharmaceutically-acceptable salt thereof.

In another aspect of the invention, suitable compounds of the invention are any one or more of the Examples or a pharmaceutically-acceptable salt thereof.

In another aspect of the invention, suitable compounds of the invention are any one or more of the following or a pharmaceutically-acceptable salt thereof:

4-[4-[[(1S,3R)-5-hydroxy-2-adamantyl]carbamoyl]-5-propylsulfanyl-pyrazol-1-yl]benzoic acid;
4-[4-(2-adamantylcarbamoyl)-5-propylsulfanyl-pyrazol-1-yl]benzoic acid;
4-[4-(1-adamantylcarbamoyl)-5-propylsulfanyl-pyrazol-1-yl]benzoic acid;
4-[4-(N-cyclohexyl-N-methyl-carbamoyl)-5-propylsulfanyl-pyrazol-1-yl]benzoic acid;
4-[4-(oxan-4-ylcarbamoyl)-5-propylsulfanyl-pyrazol-1-yl]benzoic acid;
4-[5-propylsulfanyl-4-[3-[2-(trifluoromethyl)phenyl]pyrrolidine-1-carbonyl]pyrazol-1-yl]benzoic acid;
4-[4-(cyclohexylcarbamoyl)-5-cyclopropyl-pyrazol-1-yl]benzoic acid;
4-[4-(2-adamantylcarbamoyl)-5-cyclopropyl-pyrazol-1-yl]benzoic acid;
4-[4-(1-adamantylcarbamoyl)-5-cyclopropyl-pyrazol-1-yl]benzoic acid;
4-[4-(cyclohexyl-methyl-carbamoyl)-5-cyclopropyl-pyrazol-1-yl]benzoic acid;
4-[5-cyclopropyl-4-[(4-hydroxy-1-adamantyl)carbamoyl]pyrazol-1-yl]benzoic acid;
2-[4-[4-(cyclohexylcarbamoyl)-5-propylsulfanyl-pyrazol-1-yl]phenyl]acetic acid;
2-[4-[4-(2-adamantylcarbamoyl)-5-propylsulfanyl-pyrazol-1-yl]phenyl]acetic acid;
4-(4-cyclohexylcarbamoyl-5-propylsulfanyl-pyrazol-1-ylmethyl)-benzoic acid;
3-(4-cyclohexylcarbamoyl-5-propylsulfanyl-pyrazol-1-ylmethyl)-benzoic acid;
3-[4-(adamantan-2-ylcarbamoyl)-5-propylsulfanyl-pyrazol-1-ylmethyl]-benzoic acid;
4-[4-(adamantan-2-ylcarbamoyl)-5-propylsulfanyl-pyrazol-1-ylmethyl]-benzoic acid;
4-[4-(2-adamantylcarbamoyl)-5-tert-butyl-pyrazol-1-yl]benzoic acid;
4-[4-(2-adamantylcarbamoyl)-5-(1-methylcyclopropyl)pyrazol-1-yl]benzoic acid;
4-[4-(2-adamantylcarbamoyl)-5-cyclopentyl-pyrazol-1-yl]benzoic acid;
4-[4-(2-adamantylcarbamoyl)-5-ethylpyrazol-1-yl]benzoic acid;
4-[4-(2-adamantylcarbamoyl)-5-propan-2-ylpyrazol-1-yl]benzoic acid;
4-[4-(2-adamantylcarbamoyl)-5-cyclobutylpyrazol-1-yl]benzoic acid;
4-[4-(2-adamantylcarbamoyl)-5-methyl-pyrazol-1-yl]benzoic acid;
4-(5-tert-butyl-4-(cyclohexylcarbamoyl)-1H-pyrazol-1-yl)benzoic acid;
4-[4-(2-adamantylcarbamoyl)-5-cyclohexylsulfanyl-pyrazol-1-yl]benzoic acid;
4-[4-(1-adamantylcarbamoyl)-5-cyclohexylsulfanyl-pyrazol-1-yl]benzoic acid;
4-[5-cyclohexylsulfanyl-4-[(5-hydroxy-2-adamantyl)carbamoyl]pyrazol-1-yl]benzoic acid;
4-[5-cyclohexylsulfanyl-4-[[5-(difluoromethoxy)-2-adamantyl]carbamoyl]pyrazol-1-yl]benzoic acid;
4-[4-(2-adamantylcarbamoyl)-5-cyclopentylsulfanyl-pyrazol-1-yl]benzoic acid;
methyl 4-[4-(1-adamantylcarbamoyl)-5-cyclopentylsulfanyl-pyrazol-1-yl]benzoate;
methyl 4-[5-cyclopentylsulfanyl-4-[[(1R,3S)-5-hydroxy-2-adamantyl]carbamoyl]pyrazol-1-yl]benzoate;
4-[4-[[5-(difluoromethoxy)-2-adamantyl]carbamoyl]-5-propylsulfanylpyrazol-1-yl]benzoic acid;
4-[4-(cyclohexylcarbamoyl)-5-cyclopentylsulfanyl-pyrazol-1-yl]benzoic acid;
4-[4-(cyclohexylcarbamoyl)-5-cyclohexylsulfanyl-pyrazol-1-yl]benzoic acid;
4-[5-cycloheptylsulfanyl-4-(cyclohexylcarbamoyl)pyrazol-1-yl]benzoic acid;
4-[4-(2-adamantylcarbamoyl)-5-ethylsulfanyl-pyrazol-1-yl]benzoic acid;
4-[4-(2-adamantylcarbamoyl)-5-methylsulfanyl-pyrazol-1-yl]benzoic acid;
4-[4-(5-methanesulfonyl-adamantan-2-ylcarbamoyl)-5-propylsulfanyl-pyrazol-1-yl]-benzoic acid;
4-[4-(2-adamantylcarbamoyl)-5-propylsulfanyl-pyrazol-1-yl]-2-methoxy-benzoic acid;
4-[4-(2-adamantylcarbamoyl)-5-tert-butyl-pyrazol-1-yl]-3-methyl-benzoic acid;
4-[4-(2-adamantylcarbamoyl)-5-tert-butyl-pyrazol-1-yl]-2-(trifluoromethyl)benzoic acid; or
4-[4-(adamantan-2-ylcarbamoyl)-5-(trifluoromethyl)-1H-pyrazol-1-yl]benzoic acid.

Another aspect of the present invention provides a process for preparing a compound of formula (1) or a pharmaceutically acceptable salt thereof which process (wherein variable groups are, unless otherwise specified, as defined in formula (1)) comprises any one of processes a) or b):

a) hydrolysis of an ester of formula (2):

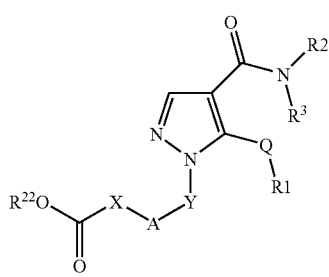

(2)

wherein $R^{22}$ is an alkyl or aryl group; or b) converting Z in a compound of the formula (3):

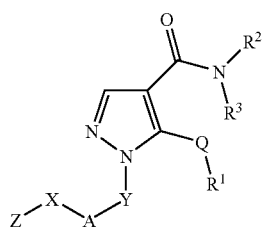

(3)

into a carboxy group, wherein Z is an functional group capable of conversion into a carboxylic acid;

and thereafter if necessary or desirable:

i) converting a compound of the formula (1) into another compound of the formula (1);

ii) removing any protecting groups;

iii) resolving enantiomers;

iv) forming a pharmaceutically-acceptable salt thereof.

Examples of conversions of a compound of Formula (1) into another compound of Formula (1), well known to those skilled in the art, include functional group interconversions such as hydrolysis, hydrogenation, hydrogenolysis, oxidation or reduction, and/or further functionalisation by standard reactions such as amide or metal-catalysed coupling, or nucleophilic displacement reactions.

Suitable conditions for the above processes a) to b) are as follows.

Process a) may be carried out under either acidic or basic conditions dependant on the nature of the ester group ($R^{22}$) but typically may be carried out under basic conditions, for example with aqueous sodium hydroxide, using a suitable solvent such as methanol for example. Typically the reaction is carried out at ambient temperature, however some esters may require cleavage using Microwave or conventional heating, for example at temperatures between 30-100° C. Examples of suitable values for $R^{22}$ include methyl, ethyl, tert-butyl, phenyl, benzyl and paramethoxybenzyl, particularly methyl or ethyl.

Compounds of formula (2) may be made by processes known in the art and typically by reaction of a compound of Formula (4) with a compound of Formula (5):

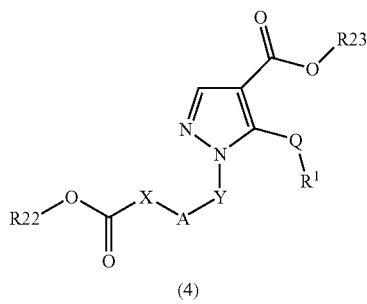 + 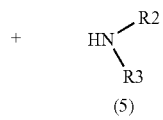

(4) (5)

Such reactions may be carried out by direct treatment of esters with amines or alternatively by hydrolysis of the $R^{23}$ ester group to an intermediate carboxylic acid followed by conventional amide coupling reactions. Methods and standard conditions for orthogonal removal of ester groups are known persons skilled in the art, for example if $R^{22}$ is ethyl and $R^{23}$ is tert-butyl, $R^{23}$ may be selectively cleaved under acidic conditions.

Amide formation can be carried out in a suitable solvent such as dichloromethane for example with the addition of a suitable coupling agent (or combination of agents) such as HOBT and EDCI for example, optionally in the presence of a suitable base such as triethylamine or N,N-di-iso-propylamine for example. Typically the reaction is carried out at ambient or elevated temperature between 0-60° C.

Compounds of formula (4) in which Q is a sulphur, oxygen or nitrogen atom may be made by processes known in the art and typically by reaction of a compound of Formula (6) with displacement of an appropriate leaving group (L):

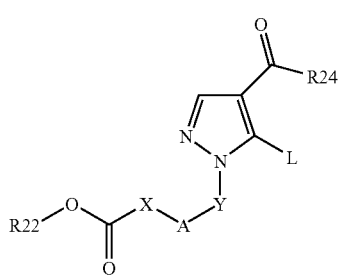

(6)

wherein L is a suitable leaving group, for example halo or triflate (in particular fluoro or chloro), $R^{22}$ is an alkyl or aryl group and $R^{24}$ is either $-OR^{23}$ or $NR^2R^3$.

Displacements may be carried out for example using a suitable nucleophilic reagent, for example propane thiol, in a suitable solvent such as DMF for example in the presence of an appropriate base, for example sodium hexamethyldisilazide (NaHMDS). Typically the reaction is carried out at ambient temperature when L is chloro, however some reactions may require using Microwave or conventional heating, for example at temperatures between 30-100° C.

Compounds of formula (6) may be made by processes known in the art and typically by functional group interconversion of a compound of Formula (7).

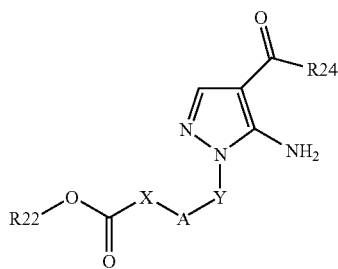

(7)

wherein $R^{22}$ is an alkyl or aryl group and $R^{24}$ is either $-OR^{23}$ or $NR^2R^3$.

Examples of such processes are known to the art and may be carried out using a combination of reagents such as tert-butylnitrite with a cupric halide in a suitable solvent such as acetonitrile for example. Typically the reaction is carried out at elevated temperature when for example, L is chloro, using Microwave or conventional heating, for example at temperatures between 60-100° C.

Compounds of formula (7) may be made by processes known in the art and typically by reaction of a hydrazine of formula (8) with an enol ether of Formula (9).

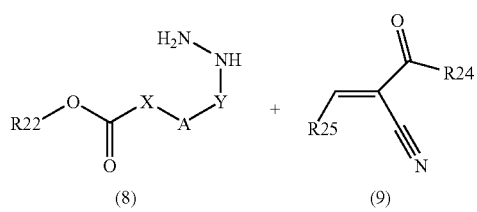

(8)   (9)

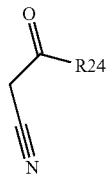

(10)

wherein $R^{24}$ is either —OR23 or $NR^2R^3$.

Examples of such processes are known to the art and are typically carried out using a combination of reagents, for example neat acetic anhydride and triethyl orthoformate. Typically the reaction is carried out at elevated temperature using Microwave or conventional heating, for example at temperatures between 60-100° C. Ketonitriles of formula (10) are known in the chemical literature or may be prepared using standard conditions known to those skilled in the art.

Compounds of formula (4) in which Q is a single bond may also be prepared by processes known in the art and typically involve the formation of a functionalised keto ester of Formula (11B) wherein X represents either dialkylamino (such as dimethylamino) or lower alkoxy (such as methoxy or ethoxy) and subsequent reaction with hydrazines of Formula (8)

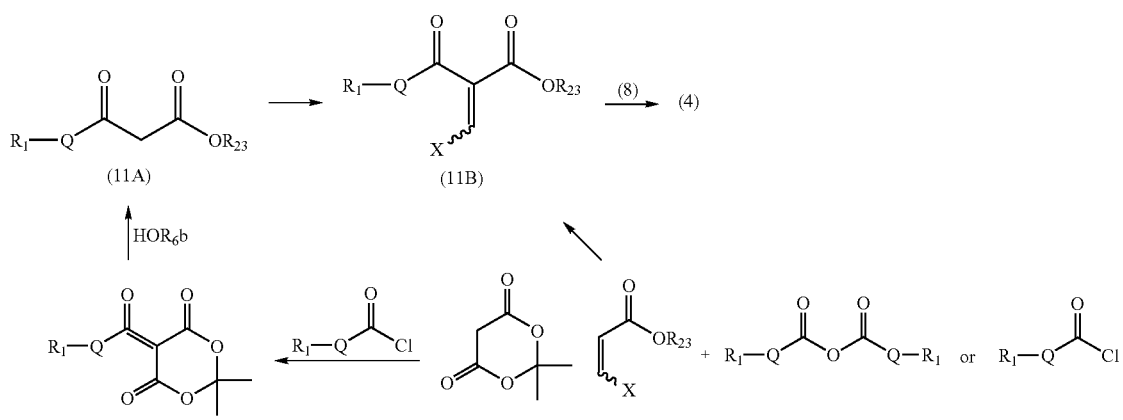

wherein $R^{22}$ is an alkyl or aryl group, $R^{24}$ is either —OR23 or $NR^2R^3$ and $R^{25}$ is an alkyl group. In particular, $R^{25}$ is methyl or ethyl.

Examples of such processes are known to the art and are typically carried out using a in a suitable solvent such as ethanol for example in the presence of a suitable base such as DIPEA for example. Typically the reaction is carried out at elevated temperature using Microwave or conventional heating, for example at temperatures between 60-100° C. Hydrazines of formula (8) are known in the chemical literature or may be prepared using standard conditions known to those skilled in the art.

Compounds of formula (9) may be made by processes known in the art and typically by functionalisation of a ketonitrile of Formula (10).

The ketoesters of formula (11B) are known in the chemical literature or may be prepared using standard conditions known to those skilled in the art, including by reaction of an acid chloride with Meldrum's acid (see for example *J. Org. Chem.* 2001, 26, 6756) in an inert solvent such as dichloromethane in the presence of a base such as pyridine, followed by reaction of the resultant intermediate with an alcohol $HOR^{23}$ (see for example *J. Org. Chem.* 1978, 43, 2087)

Compounds of formula (2) in which Q is a single bond may also be prepared by processes known in the art and typically involve the formation of a functionalised keto amide of Formula (12) wherein X' represents either dialkylamino (such as dimethylamino) or lower alkoxy (such as methoxy or ethoxy) and subsequent reaction with hydrazines of Formula (8)

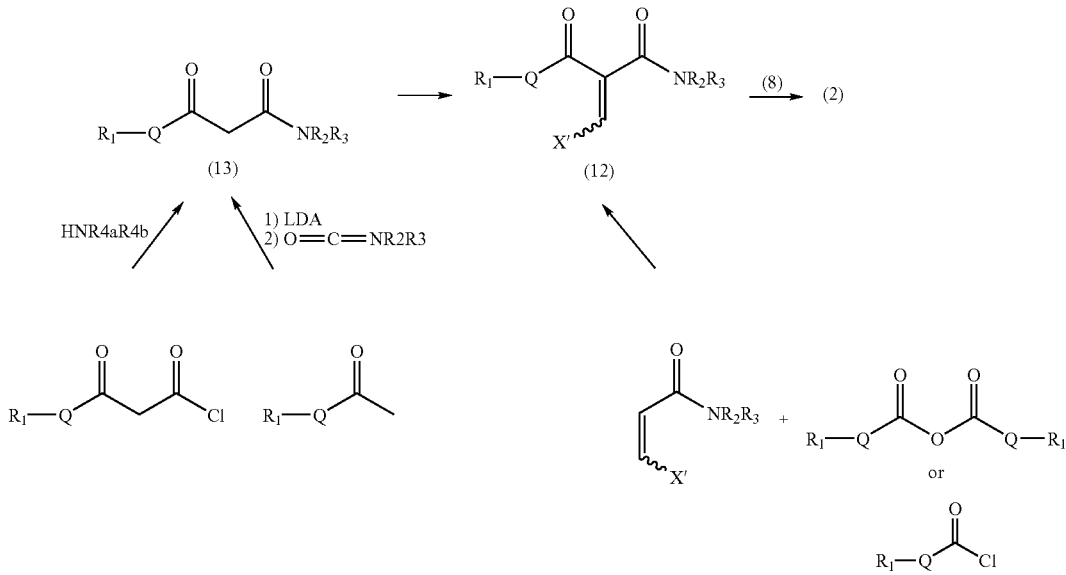

Ketoamides of formula (13) are known in the chemical literature or may be prepared using standard conditions known to those skilled in the art, including by reaction of an amine with a suitable acid chloride, optionally prepared in situ from the corresponding acid, or by reaction of an enolate anion, generated by treating a ketone with a strong base (such as LDA), with an appropriate isocyanate.

An example of process b) is the conversion of an aryl halide into an aryl carboxylic acid through the use of metal-catalysed carbonylation. Examples of such processes are known to the art and are carried out in a suitable solvent such as ethanol/dioxane for example using a suitable catalyst, or combination of catalysts, for example, Herrmann's catalyst together with Fu's salt in the presence of a suitable source of carbon monoxide, for example, molybdenum hexacarbonyl or gaseous CO typically in the presence of a suitable base, or combination of bases for example DMAP/DIPEA. Typically the reaction is carried out at elevated temperature using Microwave or conventional heating, for example at temperatures between 100-180° C. It will be appreciated by those skilled in the art that the choice of solvent will depend on the nature of the product isolated, for example alcoholic solvents will tend to lead to isolation of the ester which may be subsequently cleaved on work-up of the reaction to give the appropriate acid. It will also be appreciated by those skilled in the art that compounds of formula (3) may be accessed by all of the methods used to describe the synthesis of compounds of formula (2).

In addition, a compound of formula (3) may be prepared:

by reaction of a suitably functionalised moiety of formula (3A) with an N unsubstituted pyrazole of formula (3B) to provide the precursor of formula (3)

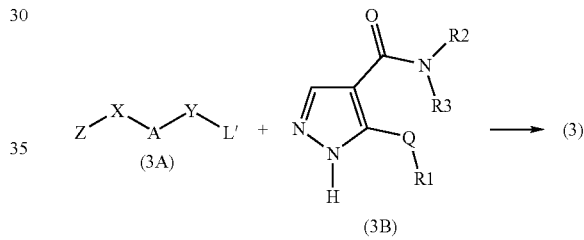

wherein L' is a leaving group capable of being displaced in an SN2 reaction (when Y becomes joined by an sp3 carbon to the ring) or in SNAr reaction (when Y becomes joined by an sp2 carbon to the ring; optionally catalysed by appropriate transition metal catalysts, for example Buchwald displacements) and in which optionally involves deprotonation of the pyrazole (3B) by a base such as potassium t-butoxide. L' is a leaving group such as chloro, bromo or iodo.

The reactions described above may be performed under standard conditions known to the person skilled in the art. The intermediates described above are commercially available, are known in the art or may be prepared by known procedures and/or by the procedures shown above.

It will be appreciated that certain of the various substituents in the compounds of the present invention may be introduced by standard aromatic substitution reactions or generated by conventional functional group modifications either prior to or immediately to following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example hydroxylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possess 11βHSD1 inhibitory activity. These properties may be assessed using the following assay.

Assays

The conversion of cortisone to the active steroid cortisol by 11βHSD1 oxo-reductase activity, can be measured using a competitive homogeneous time resolved fluorescence assay (HTRF) (CisBio International, R&D, Administration and Europe Office, In Vitro Technologies—HTRF®/Bioassays BP 84175, 30204 Bagnols/Cèze Cedex, France. Cortisol bulk HTRF kit: Cat No. 62CORPEC).

The evaluation of compounds described herein was carried out using a baculovirus expressed N terminal 6-His tagged full length human 11βHSD1 enzyme (*1). The enzyme was purified from a detergent solublised cell lysate, using a copper chelate column. Inhibitors of 11βHSD1 reduce the conversion of cortisone to cortisol, which is identified by an increase in signal, in the above assay.

*1 The Journal of Biological Chemistry, Vol. 26, No 25, pp 16653-16658

Compounds to be tested were dissolved in dimethyl sulphoxide (DMSO) to 10 mM and diluted further in assay buffer containing 1% DMSO to 10 fold the final assay concentration. Diluted compounds were then plated into black 384 well plates (Matrix, Hudson N.H., USA).

The assay was carried out in a total volume of 20 µl consisting of cortisone (Sigma, Poole, Dorset, UK, 160 nM), glucose-6-phosphate (Roche Diagnostics, 1 mM), NADPH (Sigma, Poole, Dorset, 100 µM), glucose-6-phosphate dehydrogenase (Roche Diagnostics, 12.5 µg/ml), EDTA (Sigma, Poole, Dorset, UK, 1 mM), assay buffer ($K_2HPO_4/KH_2PO_4$, 100 mM) pH 7.5, recombinant 11βHSD1 [using an appropriate dilution to give a viable assay window—an example of a suitable dilution may be 1 in 1000 dilution of stock enzyme] plus test compound. The assay plates were incubated for 25 minutes at 37° C. after which time the reaction was stopped by the addition of 10 µl of 0.5 mM glycerrhetinic acid plus conjugated cortisol (XL665 or D2). 10 µl of anti-cortisol Cryptate was then added and the plates sealed and incubated for 6 hours at room temperature. Fluorescence at 665 nm and 620 nm was measured and the 665 nm:620 nm ratio calculated using an Envision plate reader.

These data were then used to calculate $IC_{50}$ values for each compound (Origin 7.5, Microcal software, Northampton Mass., USA) and/or the % inhibition at 30 µM of compound.

Compounds of the present invention typically show an $IC_{50}$ of less than 30 µM, and preferably less than 5 µM.

For example, the following results were obtained:

| Ex. No. | IC50 (uM) |
| --- | --- |
| 3 | 0.012 |
| 6 | 3.505 |
| 4 | 0.034 |
| 8 | 0.161 |
| 17 | 0.004 |
| 20 | 0.006 |
| 22 | 0.008 |
| 23 | 0.004 |
| 24 | 0.005 |
| 27 | 0.008 |
| 33 | 0.009 |
| 36 | 0.004 |

-continued

| Ex. No. | IC50 (uM) |
|---|---|
| 38 | 0.007 |
| 41 | 0.003 |
| 43 | 0.185 |
| 44 | 0.005 |

The following table displays % inhibition of human 11-βHSD at a test concentration of 30 μM of compound

| Ex. No. | % @ 30 uM |
|---|---|
| 1 | 91 |
| 2 | 93 |
| 3 | 105 |
| 4 | 114 |
| 5 | 90 |
| 6 | 80 |
| 7 | 91 |
| 8 | 94 |
| 9 | 78 |
| 10 | 84 |
| 11 | 82 |
| 12 | 92 |
| 13 | 96 |
| 14 | 89 |
| 15 | 92 |
| 16 | 91 |
| 17 | 95 |
| 18 | 89 |
| 19 | 90 |
| 20 | 90 |
| 21 | 91 |
| 22 | 98 |
| 23 | 102 |
| 24 | 104 |
| 25 | 90 |
| 26 | 100 |
| 27 | 95 |
| 28 | 87 |
| 29 | 91 |
| 30 | 91 |
| 31 | 105 |
| 32 | 103 |
| 33 | 97 |
| 34 | 100 |
| 35 | 94 |
| 36 | 89 |
| 37 | 94 |
| 38 | 91 |
| 39 | 98 |
| 40 | 99 |
| 41 | 91 |
| 42 | 94 |
| 43 | 97 |
| 44 | 94 |
| 45 | 94 |
| 46 | 98 |
| 47 | 90 |

The oral bioavailability of the compounds of the invention may be tested as follows:

Determination of Bioavailability in PK Studies

Compounds are dosed intravenously at 2 mg/kg (2 ml/kg) and orally at 5 mg/kg (5 ml/kg) in a 25% HPBCD in sorrensons buffer pH 5.5 formulation. Blood samples (200 ul) are taken Predose, 0.25, 0.5, 1, 2, 3, 4, 5, 6, 8 and 24 h post dose for both routes and plasma prepared by centrifugation. Plasma samples are analysed as below. PK parameters (clearance, volume of distribution, bioavailability, fraction absorbed etc.) are calculated by standard PK methods using suitable PK software (WinNon-Lin).

Bioanalysis of Plasma Samples

The guidelines described are for the manual preparation of plasma samples following single compound or cassette dosing of project compounds to all PK species used within discovery DMPK. Analysis by open access (LC-MS/MS) or manual approaches (LC-MS) is described.

Contents
1. Materials
2. Generic Extraction Method
3. Example Sample List Using Generic Plate Layout
4. Open Access Batch Submission and System Checks
5. Acceptance Criteria for Batch Pass 1. Materials Solvents: Methanol, acetonitrile and DMSO Water: Purified or HPLC grade 1 ml shallow 96-well plates OR eppendorf tubes 2 ml deep well 96-well plates plus lids Blank (control) plasma 2. Generic Extraction Method Solubilise compound(s) to 1 mg/ml using DMSO taking into account salt factors if any. The DMSO stock(s) may be used to make all calibration & quality control (QC) samples:

2.i Single Compound Analysis 2.i.a Preparation of Calibration and QC Samples:
1. Prepare standard solutions as follows:

| Stock diluted ng/ml | Volume methanol ml | Volume stock ml | Standard conc. ng/ml | Post plasma dilution conc. ng/ml |
|---|---|---|---|---|
| 1 mg/ml | 0.9 | 0.1 | 100,000 | 10,000 |
| 100,000 | 0.5 | 0.5 | 50,000 | 5,000 |
| 50,000 | 0.75 | 0.5 | 20,000 | 2,000 |
| 20,000 | 0.5 | 0.5 | 10,000 | 1,000 |
| 10,000 | 0.5 | 0.5 | 5,000 | 500 |
| 5,000 | 2 | 0.5 | 1,000 | 100 |
| 1,000 | 0.5 | 0.5 | 500 | 50 |
| 500 | 0.75 | 0.5 | 200 | 20 |
| 200 | 0.5 | 0.5 | 100 | 10 |
| 100 | 0.5 | 0.5 | 50 | 5 |
| 50 | 0.5 | 0.5 | 10 | 1 |

2. Transfer 50 ul blank plasma to a well of a 1 ml 96-well plate (shallow well)
3. Transfer 5 ul of each of the standard solutions to further wells of the plate
4. Add 50 ul blank plasma to each of these wells.
5. To generate the QC samples, add three aliquots of 5 ul of the 100 ng/ml, 1000 ng/ml and 10,000 ng/ml standard solutions to the plate (3 QCs at each concentration).
6. Add 50 ul blank plasma to each of these.
7. Transfer 50 ul of each PK sample to the 1 ml 96-well plate
8. Add 5 ul methanol (– compound) to each of the PK samples
9. Ensure all dose formulations are well mixed by vortex mixing.

10. Dilute intravenous (IV) and oral dose (PO) formulations of expected concentration to 10 ug/ml in methanol. (For example, a formulation made to an expected concentration of 2 mg/ml would be diluted 1:200 to give 10 ug/ml solution).
11. Add 6×50 ul aliquots of plasma to the plate. Add 5 ul of diluted IV formulation to three of the wells, repeat with PO formulation and remaining 3 wells.
12. Precipitate proteins by adding 100 ul acetonitrile containing a project related internal standard (at 1 ug/ml) to all calibration, QC, PK and formulation samples.
13. Vortex mix the plate before centrifugation at 4,000 g for 10 minutes.
14. Transfer 100 ul of the supernatant to the wells of a 2 ml 96-well plate (see following plate map). Care should be taken not to disturb the pellet.
15. Add ~1.5 ml of 50:50 Methanol:Water into the last well.
16. For analysis on triple quad systems: add 400 ul water (HPLC grade) to each sample. Gently mix.
17. Add 100 ul of the 100,000 ng/ml stock of each of the standard solutions to the 2 ml plate and add 900 ul water. Add a sample of internal standard to a further well (see plate map). These are for compound tuning (denoted on the plate map as tune solutions)
18. For analysis on platform systems: add 100 ul water (HPLC grade) to each sample. Gently mix.
19. Manually tune all compounds using compound solutions prepared to 5,000 ng/ml (add 100 ul of the 50,000 ng/ml standard solutions to 900 ul water)

2.ii Cassette Dose Analysis
2.iia Preparation of Calibration and QC Samples:

Note: For cassette dosing, the amount of methanol required to dilute the 1 mg/ml stock will be adjusted according to the number of compounds present.

1. Add 100 ul of each 1 mg/ml stock required to a vial.
2. Add the required volume of methanol to yield a total volume of 1 ml.
3. Perform all further steps as for single compound analysis (steps 2-16 above).

2.iii In Cases where PK Samples Exceed the Upper Limit of Quantification (ULOQ).

1. Prepare a further calibration curve and QC samples as above (steps 1-6).
2. Transfer <50 ul (e.g. 25 ul) of the PK samples that exceed the ULOQ.
3. Add enough control plasma to these samples to yield a final plasma volume of 50 ul. Make a note of the dilution made.
4. Transfer 50 ul of all remaining PK samples.
5. Prepare all formulation samples and extract all samples as described above. (steps 8-16)

Note: Upper concentrations used to generate the calibration curve may be reviewed, however, care must be taken to avoid saturation of the HPLC column or MS equipment. It is for this reason that dilution of PK samples is recommended.

2.iv In Cases of Poor Sensitivity (High Lower Limit of Quantification).

Note: High LLOQ is taken as when most of the plasma concentrations lie below the lower limit of quantification or where the LLOQ is greater the 10 ng/ml. The following methods should be applied when either of these scenarios is encountered.

According to a further aspect of the invention there is provided a pharmaceutical composition, which comprises a compound of the Examples, or a pharmaceutically-acceptable salt thereof, as defined hereinbefore in association with a pharmaceutically-acceptable diluent or carrier.

The compositions of the invention may be in a form suitable for oral use (for to example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). In general, compositions in a form suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene to oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

We have found that the compounds defined in the present invention, or a pharmaceutically-acceptable salt thereof, are effective 11βHSD1 inhibitors, and to accordingly have value in the treatment of disease states associated with metabolic syndrome.

It is to be understood that where the term "metabolic syndrome" is used herein, this relates to metabolic syndrome as defined in 1) and/or 2) or any other recognised definition of this syndrome. Synonyms for "metabolic syndrome" used in the art include Reaven's Syndrome, Insulin Resistance Syndrome and Syndrome X. It is to be understood that where the term "metabolic syndrome" is used herein it also refers to Reaven's Syndrome, Insulin Resistance Syndrome and Syndrome X.

According to a further aspect of the present invention there is provided a compound of formula (1), or a pharmaceutically-acceptable salt thereof, as defined hereinbefore for use in a method of prophylactic or therapeutic treatment of a warm-blooded animal, such as man.

Thus according to this aspect of the invention there is provided a compound of formula (1), or a pharmaceutically-acceptable salt thereof, as defined hereinbefore for use as a medicament.

According to another feature of the invention there is provided the use of a compound of formula (1), or a pharmaceutically-acceptable salt thereof, as defined hereinbefore in the manufacture of a medicament for use in the production of an 11βHSD1 inhibitory effect in a warm-blooded animal, such as man.

Where production of or producing an 11βHSD1 inhibitory effect is referred to suitably this refers to the treatment of metabolic syndrome. Alternatively, where production of an 11βHSD1 inhibitory effect is referred to this refers to the treatment of diabetes, obesity, hyperlipidaemia, hyperglycaemia, hyperinsulinemia or hypertension, particularly diabetes and obesity. Alternatively, where production of an 11βHSD1 inhibitory effect is referred to this refers to the treatment of glaucoma, osteoporosis, tuberculosis, dementia, cognitive disorders or depression.

Alternatively, where production of an 11βHSD1 inhibitory effect is referred to this refers to the treatment of cognitive disorders, such as improving the cognitive ability of an individual, for example by improvement of verbal fluency, verbal memory or logical memory, or for treatment of mild cognitive disorders. See for example WO03/086410 and references contained therein, and Proceedings of National Academy of Sciences (PNAS), 2001, 98(8), 4717-4721.

Alternatively, where production of an 11βHSD1 inhibitory effect is referred to this refers to the treatment of, delaying the onset of and/or reducing the risk of atherosclerosis—see for example J. Experimental Medicine, 2005, 202(4), 517-527.

Alternatively, where production of an 11βHSD1 inhibitory effect is referred to this refers to the treatment of Alzheimers and/or neurodegenerative disorders.

According to a further feature of this aspect of the invention there is provided a method for producing an 11βHSD1 inhibitory effect in a warm-blooded animal, such as man, in need of such treatment which comprises administering to said animal an effective amount of a compound of formula (1), or a pharmaceutically-acceptable salt thereof.

In addition to their use in therapeutic medicine, the compounds of formula (1), or a pharmaceutically-salt thereof, are also useful as pharmacological tools in the development and standardisation of in vitro and in vivo test systems for the evaluation of the effects of inhibitors of 11βHSD1 in laboratory animals such as cats, dogs, rabbits, monkeys, rats and mice, as part of the search for new therapeutic agents.

The inhibition of 11βHSD1 described herein may be applied as a sole therapy or may involve, in addition to the subject of the present invention, one or more other substances and/or treatments. Such conjoint treatment may be achieved by way of the simultaneous, sequential or separate administration of the individual components of the treatment. Simultaneous treatment may be in a single tablet or in separate tablets. For example agents than might be co-administered with 11βHSD1 inhibitors, particularly those of the present invention, may include the following main categories of treatment:

1) Insulin and insulin analogues;

2) Insulin secretagogues including sulphonylureas (for example glibenclamide, glipizide), prandial glucose regulators (for example repaglinide, nateglinide), glucagon-like peptide 1 agonist (GLP1 agonist) (for example exenatide, liraglutide) and dipeptidyl peptidase IV inhibitors (DPP-IV inhibitors);

3) Insulin sensitising agents including PPARγ agonists (for example pioglitazone and rosiglitazone);

4) Agents that suppress hepatic glucose output (for example metformin);

5) Agents designed to reduce the absorption of glucose from the intestine (for example acarbose);

6) Agents designed to treat the complications of prolonged hyperglycaemia; e.g. aldose reductase inhibitors 7) Other anti-diabetic agents including phosotyrosine phosphatase inhibitors, glucose 6-phosphatase inhibitors, glucagon receptor antagonists, glucokinase activators, glycogen phosphorylase inhibitors, fructose 1,6 bisphosphastase inhibitors, glutamine:fructose-6-phosphate amidotransferase inhibitors 8) Anti-obesity agents (for example sibutramine and orlistat);

9) Anti-dyslipidaemia agents such as, HMG-CoA reductase inhibitors (statins, eg pravastatin); PPARα agonists (fibrates, eg gemfibrozil); bile acid sequestrants (cholestyramine); cholesterol absorption inhibitors (plant stanols, synthetic inhibitors); ileal bile acid absorption inhibitors (IBATi), cholesterol ester transfer protein inhibitors and nicotinic acid and analogues (niacin and slow release formulations);

10) Antihypertensive agents such as, β blockers (eg atenolol, inderal); ACE inhibitors (eg lisinopril); calcium antagonists (eg. nifedipine); angiotensin receptor antagonists (eg candesartan), a antagonists and diuretic agents (eg. furosemide, benzthiazide);

11) Haemostasis modulators such as, antithrombotics, activators of fibrinolysis and antiplatelet agents; thrombin antagonists; factor Xa inhibitors; factor VIIa inhibitors; antiplatelet agents (eg. aspirin, clopidogrel); anticoagulants (heparin and Low molecular weight analogues, hirudin) and warfarin;

12) Anti-inflammatory agents, such as non-steroidal anti-inflammatory drugs (eg. aspirin) and steroidal anti-inflammatory agents (eg. cortisone); and 13) Agents that prevent the reabsorption of glucose by the kidney (SGLT inhibitors).

In the above other pharmaceutical composition, process, method, use and medicament manufacture features, the alternative and preferred embodiments of the compounds of the invention described herein also apply.

EXAMPLES

The invention will now be illustrated by the following Examples in which, unless stated otherwise:

(i) temperatures are given in degrees Celsius (° C.); operations were carried out at room or ambient temperature, that is, at a temperature in the range of 18-25° C. and under an atmosphere of an inert gas such as argon;

(ii) evaporation of solvent was carried out using a rotary evaporator under reduced pressure (600-4000 Pa; 4.5-30 mmHg) with a bath temperature of up to 60° C.;

(iii) chromatography means flash chromatography on silica gel;

(iv) in general, the course of reactions was followed by TLC and reaction times are given for illustration only;

(v) yields are given for illustration only and are not necessarily those which can be obtained by diligent process development; preparations were repeated if more material was required;

(vi) where given, NMR data ($^1$H) is in the form of delta values for major diagnostic protons, given in parts per million (ppm) relative to tetramethylsilane (TMS), determined at 300 or 400 MHz (unless otherwise stated) using perdeuterio dimethyl sulfoxide (DMSO-$d_6$) as solvent, unless otherwise stated; peak multiplicities are shown thus: s, singlet; d, doublet; dd, doublet of doublets; dt, doublet of triplets; dm, doublet of multiplets; t, triplet, m, multiplet; br, broad;

(vii) chemical symbols have their usual meanings; SI units and symbols are used;

(viii) solvent ratios are given in volume: volume (v/v) terms;

(ix) mass spectra (MS) were run with an electron energy of 70 electron volts in the chemical ionisation (CI) mode using a direct exposure probe; where indicated ionisation was effected by electron impact (EI), fast atom bombardment (FAB) or electrospray (ESP); values for m/z are given; generally, only ions which indicate the parent mass are reported;

(x) The following abbreviations may be used below or in the process section hereinbefore:
    $Et_2O$ diethyl ether
    DMF dimethylformamide
    DCM dichloromethane
    DME 1,2-dimethoxyethane
    MeOH methanol
    EtOH ethanol
    TFA trifluoroacetic acid
    THF tetrahydrofuran
    DMSO dimethylsulfoxide
    HOBT 1-hydroxybenzotriazole
    EDCI (EDAC) 1-ethyl-3-(3-dimethylaminopropyl)carbodi-imide hydrochloride
    DIPEA diisopropylethylamine
    DMAP 4-dimethylaminopyridine
    DEAD diethyl azodicarboxylate
    EtOAc ethyl acetate
    $MgSO_4$ magnesium sulfate
    MTBE methyl tert-butyl ether
    NaHMDS sodium hexamethyldisalazide

Example 1

4-[4-((1R,2S,3S,5S)-5-Hydroxy-adamantan-2-ylcarbamoyl)-5-propylsulfanyl-pyrazol-1-yl]-benzoic acid

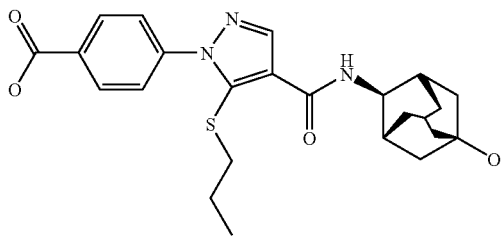

4-[4-((1R,2S,3S,5S)-5-Hydroxy-adamantan-2-ylcarbamoyl)-5-propylsulfanyl-pyrazol-1-yl]-benzoic acid methyl ester (0.34 mmol) (Intermediate #1) was dissolved in methanol (10 mL) and treated with 2M sodium hydroxide solution (0.84 mL, 1.7 mmol). The mixture was stirred at ambient temperature for 24 h and then the methanol was removed by evaporation under reduced pressure. The residue was dissolved in water (10 mL), acidified to pH4 with 2M HCl and extracted with EtOAc (2×10 mL). The combined extracts were washed with water (10 mL) and brine (10 mL) and dried (MgSO$_4$) and evaporated to leave the title compound as a white solid. (74 mg, 48%).

$^1$H NMR (300.073 MHz, DMSO-d$_6$) δ0.66 (3H, t), 1.18-1.30 (2H, m), 1.42 (2H, d), 1.58-1.80 (6H, m), 1.88 (2H, d), 2.06 (3H, s), 2.62 (2H, t), 3.95-4.06 (1H, m), 4.42 (1H, s), 7.71 (2H, d), 7.95 (1H, d), 8.09 (2H, d), 8.16 (1H, s), 13.19 (1H, s)

MS m/z 456 M+H

Example 2

4-[4-(2-Adamantylcarbamoyl)-5-propylsulfanyl-pyrazol-1-yl]benzoic acid

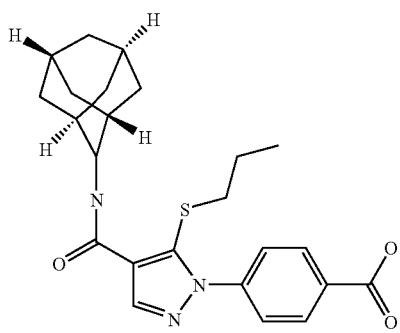

Methyl 4-[4-(2-adamantylcarbamoyl)-5-propylsulfanyl-pyrazol-1-yl]benzoate (190 mg, 0.42 mmol) (Intermediate #2) was dissolved in methanol (10 mL) and treated at ambient temperature with 2M aqueous sodium hydroxide solution (1.05 mL, 2.1 mmol). The mixture was stirred at ambient temperature for 18 h. and then heated to 65° C. for a further 2 h. Methanol was removed by evaporation under reduced pressure and the clear solution diluted with water (25 ml). 2M HCl was added to pH4 and the mixture extracted with ethyl acetate (2×25 mL). The combined extracts were washed with water (2×10 mL) and brine (10 mL), dried (MgSO$_4$) and evaporated to give the title compound as a white solid. (174 mg, 94%)

$^1$H NMR (300.073 MHz, DMSO-d$_6$) δ0.65 (3H, t), 1.17-1.29 (2H, m), 1.60 (2H, d), 1.73 (2H, s), 1.83 (6H, s), 1.91-2.05 (4H, m), 2.62 (2H, t), 4.09 (1H, d), 7.75 (2H, d), 8.03 (1H, d), 8.13 (2H, d), 8.20 (1H, s)

MS m/z 440 M+H

Example 3

4-[4-(1-Adamantylcarbamoyl)-5-propylsulfanyl-pyrazol-1-yl]benzoic acid

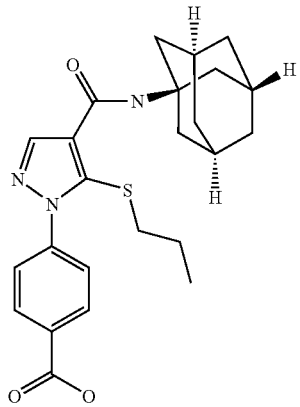

Methyl 4-[4-(1-adamantylcarbamoyl)-5-propylsulfanyl-pyrazol-1-yl]benzoate (143 mg, 0.32 mmol) (Intermediate#3) was dissolved in methanol and treated at ambient temperature with 2M aqueous sodium hydroxide solution. The mixture was stiffed at ambient for 18 h. Methanol was removed by evaporation under reduced pressure and the clear solution diluted with water (25 ml). 2M HCl was added to pH4 and the mixture extracted with ethyl acetate (2×25 mL). The combined extracts were washed with water (2×10 mL) and brine (10 mL), dried (MgSO$_4$) and evaporated to give the title compound as a white solid (132 mg, 94%).

$^1$H NMR (300.073 MHz, DMSO-d$_6$) δ0.69 (3H, t), 1.25 (2H, q), 1.66 (6H, s), 2.06 (9H, s), 2.65 (2H, t), 7.51 (1H, s), 7.66-7.69 (2H, m), 8.07-8.10 (3H, m)

MS m/z 440 M+H

Example 4

4-[4-(N-Cyclohexyl-N-methyl-carbamoyl)-5-propyl-sulfanyl-pyrazol-1-yl]benzoic acid

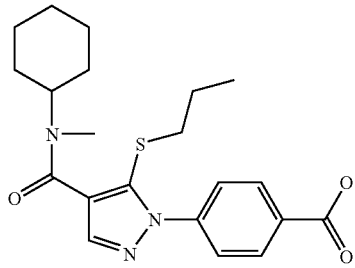

Methyl 4-[4-(cyclohexyl-methyl-carbamoyl)-5-propylsulfanyl-pyrazol-1-yl]benzoate (Intermediate#4) (162 mg, 0.39 mmol) was dissolved in methanol (10 mL) and treated at ambient temperature with 2M aqueous sodium hydroxide solution (0.96 mL, 1.95 mmol). The mixture was stirred at ambient for 18 h. Methanol was removed by evaporation under reduced pressure and the clear solution diluted with water (25 ml). 2M HCl was added to pH4 and the mixture extracted with ethyl acetate (2×25 mL). The combined extracts were washed with water (2×10 mL) and brine (10 mL), dried (MgSO$_4$) and evaporated to give the title compound as a white solid foam (150 mg, 96%).

$^1$H NMR (300.073 MHz, DMSO-d$_6$) δ0.68 (3H, t), 1.10-1.41 (4H, m), 1.42-1.85 (8H, m), 2.58 (2H, t), 2.86 (3H, s), 3.45-3.60 (0.5H. m), 4.21-4.38 (0.5H, m), 7.74 (2H, d), 7.89 (1H, s), 8.09 (2H, d)

MS m/z 402 M+H

Example 5

4-[4-(Oxan-4-ylcarbamoyl)-5-propylsulfanyl-pyrazol-1-yl]benzoic acid

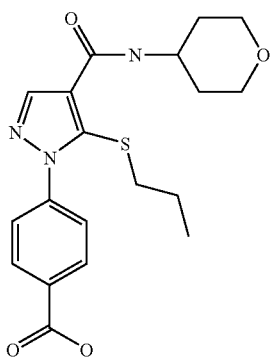

Methyl 4-[4-(oxan-4-ylcarbamoyl)-5-propylsulfanyl-pyrazol-1-yl]benzoate (Intermediate#5) (104 mg, 0.26 mmol) was dissolved in methanol (5 mL) and treated at ambient temperature with 2M aqueous sodium hydroxide solution (0.65 mL, 1.29 mmol). The mixture was stirred at ambient for 18 h. Methanol was removed by evaporation under reduced pressure and the clear solution diluted with water (25 ml). 2M HCl was added to pH4 and the mixture extracted with ethyl acetate (2×25 mL). The combined extracts were washed with water (2×10 mL) and brine (10 mL), dried (MgSO$_4$) and evaporated to give the product as a white solid (89 mg, 85%).

$^1$H NMR (300.073 MHz, DMSO-d$_6$) δ0.68 (3H, t), 1.19-1.31 (2H, m), 1.47-1.56 (2H, m), 1.77-1.81 (2H, m), 2.71 (2H, t), 3.29-3.43 (2H, m), 3.85-3.89 (2H, m), 3.94-4.04 (1H, m), 7.67 (2H, d), 8.03 (1H, d), 8.09 (2H, d), 8.16 (1H, s)

MS m/z 390 M+H

Example 6

4-[5-Propylsulfanyl-4-[3-[2-(trifluoromethyl)phenyl)pyrrolidine-1-carbonyl]pyrazol-1-yl]benzoic acid

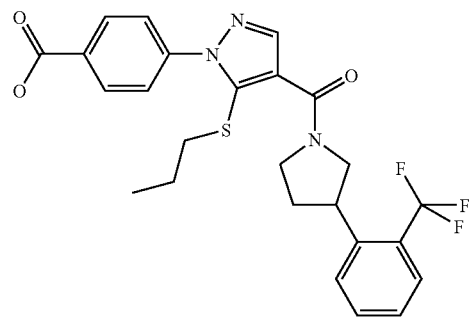

Methyl 4-[5-propylsulfanyl-4-[3-[2-(trifluoromethyl)phenyl]pyrrolidine-1-carbonyl]pyrazol-1-yl]benzoate (Intermediate#6) (177 mg, 0.34 mmol) was stirred at ambient temperature for 18 h in a mixture of methanol (5 mL) and 2M sodium hydroxide (0.855 mL, 1.71 mmol) for 18 h. The reaction mixture was evaporated to remove the methanol. The residue was dissolved in water (20 mL) and acidified to pH4 with 2M HCl. The resulting white precipitate was recovered by filtration, washed with water and dried under vacuum to give the title compound as a white solid (116 mg, 68%).

$^1$H NMR (300.073 MHz, DMSO-d$_6$) δ0.64 (3H, q), 1.14-1.26 (2H, m), 1.67-1.76 (1H, m), 1.89-1.98 (2H, m), 2.42-2.59 (3H, m), 3.62-3.82 (1H, m), 3.93-4.01 (1H, m), 5.24-5.43 (1H, m), 7.43-7.48 (2H, m), 7.58-7.75 (4H, m), 8.00-8.20 (3H, m), 13.18 (1H, s)

MS m/z 503 M+H

Example 7

4-[4-(Cyclohexylcarbamoyl)-5-propylsulfanyl-pyrazol-1-yl]benzoic acid

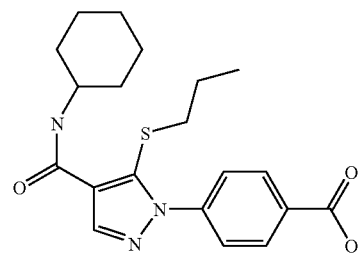

Methyl 4-[4-(cyclohexylcarbamoyl)-5-propylsulfanyl-pyrazol-1-yl]benzoate (363 mg, 0.94 mmol) (Intermediate #11) was dissolved in methanol (20 mL) and treated at ambient temperature with 2M aqueous sodium hydroxide solution (2.35 mL). The mixture was stirred at ambient temperature for 18 h and then volatiles were removed by evaporation under reduced pressure. The residue was dissolved in water (25 ml) and 2M HCl was added until the pH=4. The mixture was extracted with ethyl acetate (2×25 mL) and the combined extracts were washed with water (2×10 mL) and brine (10 mL), dried (MgSO$_4$) and evaporated to give the title product as a white solid. (300 mg 85%)

¹H NMR (300.073 MHz, DMSO-d₆) δ0.68 (3H, t), 1.14-1.39 (7H, m), 1.57-1.61 (1H, m), 1.72 (2H, d), 1.84 (2H, d), 2.70 (2H, t), 3.75-3.78 (1H, m), 7.65-7.69 (2H, m), 7.90-7.93 (1H, m), 8.07-8.13 (2H, m), 8.14 (1H, s), 13.20 (1H, s)

MS m/z 388 M+H

Example 8

3-[4-(Cyclohexylcarbamoyl)-5-propylsulfanyl-pyrazol-1-yl]benzoic acid

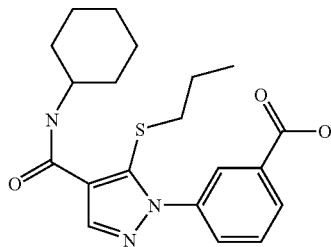

Methyl 3-[4-(cyclohexylcarbamoyl)-5-propylsulfanyl-pyrazol-1-yl]benzoate (175 mg, 0.45), (Intermediate #12) was dissolved in methanol (10 mL), treated with 2M aqueous sodium hydroxide solution (1.125 mL) and stirred at ambient temperature for 18 h. Methanol was removed by evaporation under reduced pressure and the clear solution diluted with water (25 ml). 2M HCl was added to pH4 and the mixture extracted with ethyl acetate (2×25 mL). The combined extracts were washed with water (2×10 mL) and brine (10 mL), dried (MgSO₄) and evaporated to give the title product as a white solid. (115 mg, 65%)

¹H NMR (300.073 MHz, DMSO-d₆) δ0.67 (3H, t), 1.14-1.39 (7H, m), 1.57-1.61 (1H, m), 1.70 (2H, d), 1.82-1.85 (2H, m), 2.70 (2H, t), 3.74-3.79 (1H, m), 7.66-7.71 (1H, m), 7.78-7.82 (1H, m), 7.91 (1H, d), 8.03-8.06 (2H, m), 8.13 (1H, s), 13.29 (1H, s)

MS m/z 388 M+H

Example 9

4-[4-(Cyclhexylcarbamoyl)-5-propyl-pyrazol-1-yl]benzoic acid

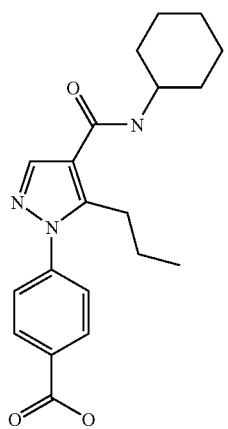

Ethyl 4-[4-(cyclohexylcarbamoyl)-5-propyl-pyrazol-1-yl]benzoate (130 mg, 0.34 mmol) (Intermediate #21) was dissolved in methanol (10 mL) and treated at ambient temperature with 2M aqueous sodium hydroxide solution (2.5 mL). The mixture was stiffed at ambient temperature for 18 h and then methanol was removed by evaporation under reduced pressure. The remaining aqueous solution was acidified with 2M aqueous hydrochloric acid to pH=2. A white solid precipitated out of solution, it was filtered, dried under vacuum and identified as the desired product (120 mg, quantitative reaction).

¹H NMR (400.13 MHz, DMSO-d₆) δ0.73 (3H, t), 1.12 (1H, m), 1.23-1.31 (1H, m), 1.28 (3H, m), 1.36-1.43 (2H, m), 1.59-1.63 (1H, m), 1.73 (2H, d), 1.80 (2H, s), 2.97 (2H, t), 3.73 (1H, m), 7.59-7.61 (2H, d), 7.95 (1H, d), 8.09-8.11 (2H, d), 8.21 (1H, s), 13.27 (1H, s)

MS m/z 356 M+H

Example 10

4-[4-(Cyclohexyl-methyl-carbamoyl)-5-propyl-pyrazol-1-yl]benzoic acid

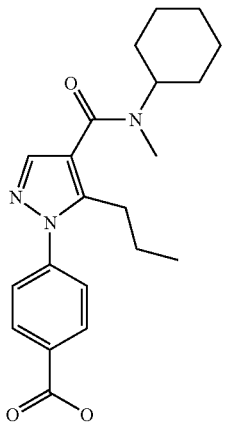

Ethyl 4-[4-(cyclohexyl-methyl-carbamoyl)-5-propyl-pyrazol-1-yl]benzoate (Intermediate #23, 105 mg, 0.26 mmol) was dissolved in methanol (10 mL) and treated at ambient temperature with 2M aqueous sodium hydroxide solution (2.5 mL). The mixture was stirred at ambient temperature for 18 h and then methanol was removed by evaporation under reduced pressure. The remaining aqueous solution was acidified with 2M aqueous hydrochloric acid to pH=2. A white solid precipitated out of solution, it was filtered, dried under vacuum and identified as the desired product (96 mg, quantitative reaction).

¹H NMR (400.13 MHz, DMSO-d₆) δ0.71 (3H, t), 1.12-1.50 (6H, m), 1.59-1.77 (6H, m), 2.79 (2H, t), 2.89 (3H, s), 7.45-7.65 (1H, m), 7.67 (2H, d), 7.84-7.86 (1H, m), 8.10 (2H, d), 13.24 (1H, s)

MS m/z 370 M+H

Example 11

4-[4-(cyclohexylcarbamoyl)-5-cyclopropyl-pyrazol-1-yl]benzoic acid

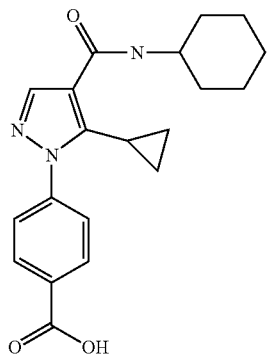

1-(4-bromophenyl)-N-cyclohexyl-5-cyclopropyl-pyrazole-4-carboxamide (Intermediate#25) (111 mg, 0.29 mmol), molybdenum hexacarbonyl (38 mg, 0.14 mmol), DMAP (70 mg, 0.57 mmol), DIPEA (74 mg, 0.57 mmol) and trans-Di(acetato)bis[o-(di-o-tolylphosphino)benzyl]dipalladium (II) (14 mg, 0.015 mmol) were added to a microwave vial and suspended in a mixture of dioxan (2 mL) and ethanol (2 mL). The vial was capped and heated to 150° C. for 1 h. The reaction mixture was evaporated to dryness and the residue dissolved in DCM (10 mL). 2 M HCl (10 ml) was added and the mixture shaken and passed through a phase separating filter. The DCM solution was dry loaded onto Ceelite and the product recovered by flash chromatography on silica gel (elution gradient 0-50% EtOAc in Hexane). Pure fractions were combined and evaporated to give the product as a white solid. The white solid was dissolved in methanol (5 mL), treated with 2M NaOH solution (1 mL) and stirred at ambient temperature for 5 h. The reaction mixture was concentrated under reduced pressure, diluted with water (20 mL), washed with ether (2×10 mL), acidified to pH4 with 2M HCl and extracted with EtOAc (3×10 mL). The combined extracts were washed with water (10 mL), dried (MgSO4) and evaporated to afford 4-[4-(cyclohexylcarbamoyl)-5-cyclopropyl-pyrazol-1-yl]benzoic acid as white solid. (40 mg, 40%)

The following Examples were prepared in a similar manner to Example #11, using an appropriate bromophenyl starting material:

| Structure | Ex | Name | $^{1}$H NMR δ | MS m/e MH$^{+}$ |
|---|---|---|---|---|
| 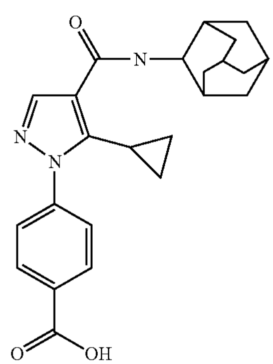 | 12 | 4-[4-(2-adamantylcarbamoyl)-5-cyclopropyl-pyrazol-1-yl]benzoic acid | 1H NMR (300.073 MHz, DMSO-d$_{6}$) δ 0.41-0.46 (2 H, m), 0.85-0.91 (2 H, m), 1.56 (2 H, d), 1.73 (2 H, s), 1.85 (6 H, d), 1.98 (2 H, d), 2.08 (2 H, d), 2.21-2.30 (1 H, m), 4.05 (1 H, d), 7.58 (1 H, d), 7.77 (2 H, d), 7.94 (1 H, s), 8.09 (2 H, d) | 406 |
| 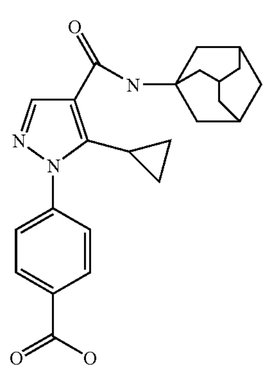 | 13 | 4-[4-(1-adamantylcarbamoyl)-5-cyclopropyl-pyrazol-1-yl]benzoic acid | 1H NMR (400.13 MHz, DMSO-d$_{6}$) δ 0.42-0.46 (2 H, m), 0.87-0.92 (2 H, m), 1.67 (6 H, s), 2.07 (9 H, s), 2.14-2.21 (1 H, m), 7.17 (1 H, s), 7.73-7.76 (2 H, m), 7.86 (1 H, s), 8.07-8.10 (2 H, m) | 406 |

-continued

| Structure | Ex | Name | ¹H NMR δ | MS m/e MH⁺ |
|---|---|---|---|---|
| 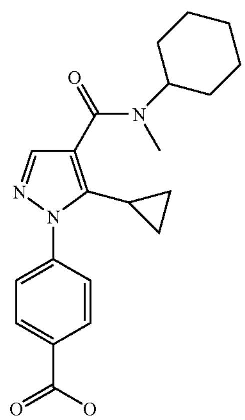 | 14 | 4-[4-(cyclohexyl-methyl-carbamoyl)-5-cyclopropyl-pyrazol-1-yl]benzoic acid | 1H NMR (300.073 MHz, DMSO-d₆) δ 0.45 (2 H, s), 0.83 (2 H, d), 1.08-1.85 (10 H, m), 2.06 (1 H, s), 2.86 (3 H, s), 3.57 (0.4 H, s), 4.15 (0.6 H, s), 7.68 (1 H, s), 7.82 (2 H, d), 8.07 (2 H, d), 13.0 (1 H, s) | 368 |
| 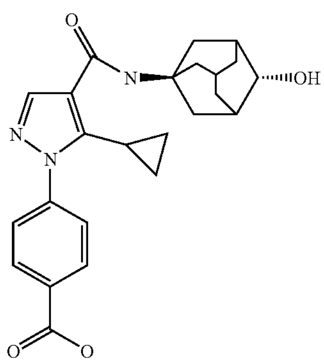 | 15 | 4-[5-cyclopropyl-4-[(4-hydroxy-1-adamantyl)carbamoyl]pyrazol-1-yl]benzoic acid | 1H NMR (400.13 MHz, DMSO-d₆) δ 0.42-0.46 (2 H, m), 0.85-0.90 (2 H, m), 1.38 (2 H, d), 1.65 (5 H, d), 1.75 (2 H, d), 1.96 (2 H, d), 2.03 (1 H, s), 2.08 (2 H, s), 2.21-2.28 (1 H, m), 3.98 (1 H, d), 4.40 (1 H, s), 7.53 (1 H, d), 7.75-7.78 (2 H, m), 7.94 (1 H, s), 8.08-8.11 (2 H, m), 13.1 (1 H | 422 |

Example 16

2-[4-[4-(Cyclohexylcarbamoyl)-5-propylsulfanyl-pyrazol-1-yl]phenyl]acetic acid

Methyl 2-[4-[4-(cyclohexylcarbamoyl)-5-propylsulfanyl-pyrazol-1-yl]phenyl]acetate (Intermediate#33) (210 mg, 0.51 mmol) was dissolved in methanol (10 mL) and treated at ambient temperature with a 2M solution of sodium hydroxide (1.27 mL, 2.53 mmol). The mixture was stiffed overnight and then methanol was removed by evaporation under reduced pressure. The clear aqueous solution was diluted with water (20 mL) and acidified to pH3 with 2M HCl. The resulting white precipitate was extracted into ethyl acetate (2×20 mL). The combined extracts were washed with brine (10 mL), dried (MgSO4) and evaporated to give the crude product. The crude product was purified by preparative HPLC using decreasingly polar mixtures of water (containing 0.1% NH3) and MeCN as eluents. Fractions containing the desired compound were evaporated to dryness to afford 2-[4-[4-(cyclohexylcarbamoyl)-5-propylsulfanyl-pyrazol-1-yl]phenyl]acetic acid. (84 mg, 41%).

1H NMR (400.13 MHz, DMSO-d₆) δ 0.72 (3H, t), 1.20-1.36 (7H, m), 1.60 (1H, d), 1.73 (2H, d), 1.85 (2H, d), 2.69 (2H, t), 3.69 (2H, s), 3.77 (1H, d), 7.42-7.47 (4H, m), 7.86 (1H, d), 8.10 (1H, s)

MS m/z (ESI+) (M+H)+402

Example 17

2-[4-[4-(2-Adamantylcarbamoyl)-5-propylsulfanyl-pyrazol-1-yl]phenyl]acetic acid

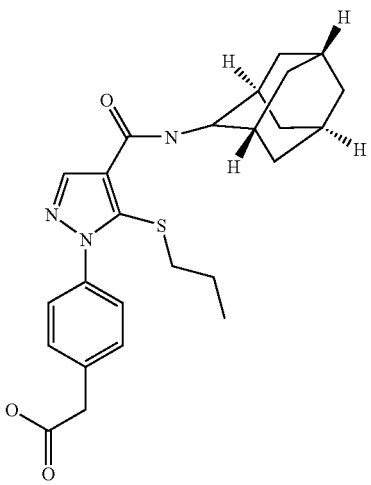

Methyl 2-[4-[4-(2-adamantylcarbamoyl)-5-propylsulfanyl-pyrazol-1-yl]phenyl]acetate (Intermediate #34) (220 mg, 0.47 mmol) was dissolved in methanol (10 mL) and treated at ambient temperature with a 2M solution of sodium hydroxide (1.17 mL, 2.35 mmol). The mixture was stiffed overnight and then methanol was removed by evaporation under reduced pressure. The clear aqueous solution was diluted with water (20 mL) and acidified to pH3 with 2M HCl. The resulting white precipitate was extracted into ethyl acetate (2×20 mL). The combined extracts were washed with brine (10 mL), dried (MgSO4) and evaporated to give the crude product. The crude product was purified by preparative HPLC using decreasingly polar mixtures of water (containing 0.1% NH3) and MeCN as eluents. Fractions containing the desired compound were evaporated to dryness to afford 2-[4-[4-(2-adamantylcarbamoyl)-5-propylsulfanyl-pyrazol-1-yl]phenyl]acetic acid (66 mg, 31%).

1H NMR (400.13 MHz, DMSO-$d_6$) δ 0.70 (3H, t), 1.23-1.32 (2H, m), 1.62 (2H, d), 1.74 (2H, s), 1.86 (6H, d), 1.99 (4H, d), 2.62 (2H, t), 3.70 (2H, s), 4.11 (1H, d), 7.45 (2H, d), 7.50-7.52 (2H, m), 8.02 (1H, d), 8.12 (1H, s)

MS m/z (ESI+) (M+H)+454

Example 18

4-(4-Cyclohexylcarbamoyl-5-propylsulfanyl-pyrazol-1-ylmethyl)-benzoic acid

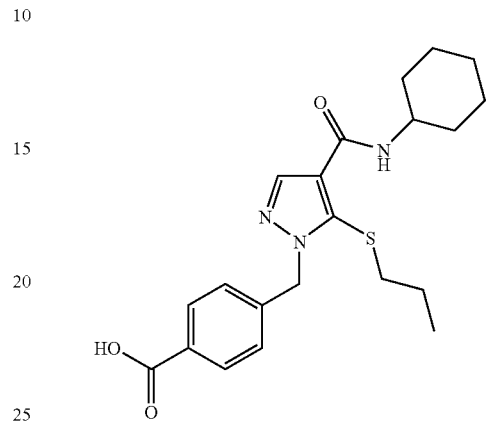

A solution of 4-(4-Cyclohexylcarbamoyl-5-propylsulfanyl-pyrazol-1-ylmethyl)-benzoic acid methyl ester (116 mg, 0.28 mmol) (Intermediate #40) and LiOH (47 mg, 1.12 mmol) in MeOH (2 ml)/Water (1 ml) was stirred overnight at ambient temperature. The bulk of the MeOH was removed in vacuo and the resulting solution was treated with citric acid (~10 ml) then extracted with EtOAc (2×~15 ml). The organic layers were combined, washed with brine (~10 ml), dried (MgSO$_4$), filtered and evaporated to yield the title compound as a white solid (102 mg, 91%).

1H NMR (700.03 MHz, CDCl$_3$) δ 0.89 (3H, t), 1.22-1.30 (4H, m), 1.41-1.46 (2H, m), 1.48-1.53 (2H, m), 1.62-1.64 (1H, m), 1.71-1.73 (1H, m), 1.98-2.00 (2H, m), 2.56 (2H, t), 3.99-4.04 (1H, m), 5.59 (2H, s), 7.27 (2H, d), 7.37 (1H, d), 8.05 (2H, d), 8.16 (1H, s)

MS m/e MH+ 402.

The following examples were made using the above procedure, replacing 4-(4-Cyclohexylcarbamoyl-5-propylsulfanyl-pyrazol-1-ylmethyl)-benzoic acid methyl ester with a corresponding starting material

| Structure | Example # | Name | NMR | [M + H]+ |
|---|---|---|---|---|
| 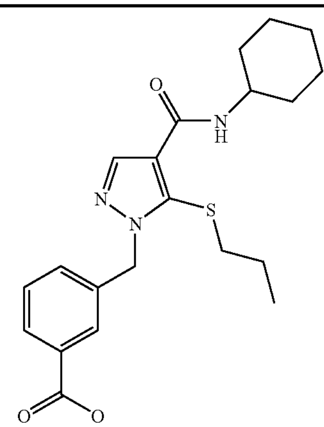 | 19 | 3-(4-Cyclohexylcarbamoyl-5-propylsulfanyl-pyrazol-1-ylmethyl)-benzoic acid | 1H NMR (300.072 MHz, CDCl$_3$) δ 0.81-1.85 (3 H, t), 1.11-1.31 (3 H, m), 1.35-1.52 (4 H, m), 1.55-1.69 (3 H, m), 1.87-1.98 (2 H, m), 2.51 (2 H, t), 3.85-4.03 (1 H, m), 5.51 (2 H, s), 7.32-7.40 (3 H, m), 7.94-7.99 (2 H, m), 8.09 (1 H, s) | 402 |

| Structure | Example # | Name | NMR | [M + H]+ |
|---|---|---|---|---|
| 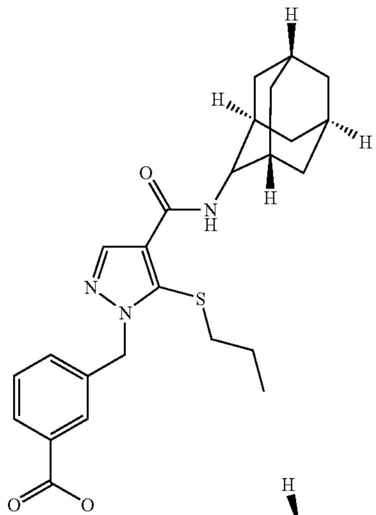 | 20 | 3-[4-(Adamantan-2-ylcarbamoyl)-5-propylsulfanyl-pyrazol-1-ylmethyl]-benzoic acid | 1H NMR (300.072 MHz, CDCl₃) δ 0.82 (3 H, t), 1.39-1.51 (2 H, m), 1.57-1.73 (4 H, m), 1.82 (8 H, s), 1.96 (2 H, s), 2.52 (2 H, t), 4.20-4.28 (1 H, m), 5.52 (2 H, s), 7.34-7.41 (2 H, m), 7.90 (1 H, d), 7.93-7.99 (2 H, m), 8.12 (1 H, s) | 454 |
| 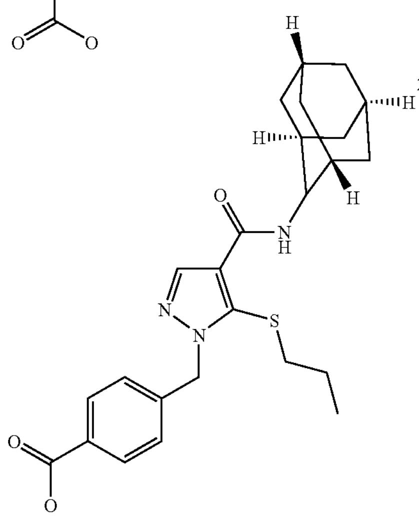 | 21 | 4-[4-(Adamantan-2-ylcarbamoyl)-5-propylsulfanyl-pyrazol-1-ylmethyl]-benzoic acid | 1H NMR (300.072 MHz, CDCl₃) δ 0.81 (3 H, t), 1.37-1.49 (2 H, m), 1.58-1.75 (4 H, m), 1.82 (8 H, s), 1.96 (2 H, s), 2.50 (2 H, t), 4.20-4.28 (1 H, m), 5.53 (2 H, s), 7.21 (2 H, d), 7.89 (1 H, d), 7.99 (2 H, d), 8.13 (1 H, s) | 454 |

Example 22

4-[4-(2-Adamantylcarbamoyl)-5-tert-butyl-pyrazol-1-yl]benzoic acid

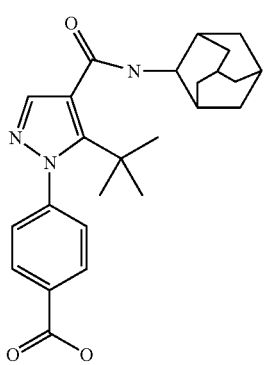

2M aqueous sodium hydroxide solution (51.7 mL, 103.32 mmol) was added to methyl 4-[4-(2-adamantylcarbamoyl)-5-tert-butyl-pyrazol-1-yl]benzoate (Intermediate#56) (4.5 g, 10.33 mmol) in methanol (100 mL). The mixture was stirred at 70° C. for 1 hour and then cooled to ambient temperature, concentrated under reduced pressure and diluted with water (100 mL). The reaction mixture was adjusted to pH 3 with 2M HCl. The reaction mixture was extracted with EtOAc (500 mL) and washed sequentially with water (2×100 mL), and saturated brine (50 mL). The organic layer was dried over MgSO4, filtered and evaporated to give a pale yellow solid. The solid was washed with EtOAc (20 mL), collected by filtration and dried under vacuum to give 4-[4-(2-adamantylcarbamoyl)-5-tert-butyl-pyrazol-1-yl]benzoic acid (3.89 g, 89%) as a cream crystalline solid.

1H NMR (400.13 MHz, DMSO-d₆) δ 1.19 (9H, s), 1.49 (2H, d), 1.70-1.96 (10H, m), 2.09 (2H, d), 3.98-4.01 (1H, m), 7.49-7.53 (2H, m), 7.61 (1H, s), 8.06-8.09 (2H, m), 8.20 (1H, d), 13.30 (1H, s)

m/z (ESI+) (M+H)+=422 m.p. 308.8° C. (onset)

Example 22 may also be prepared as follows

Aqueous sodium hydroxide (2M) (2.5 eq) was added portion-wise over 5 minutes to a stirred suspension of methyl 4-[4-(2-adamantylcarbamoyl)-5-tert-butyl-pyrazol-1-yl]benzoate (Intermediate#56) (1.0 eq) in methanol (10 vol) at 20° C. (exotherm 20-27° C.). The resulting suspension was heated to 70° C. (jacket temperature), (batch refluxes approx 60-65° C.) for 1 hour (complete by LCMS). The orange reaction mixture was cooled to 20° C. (solution remained slightly cloudy) and filtered through celite to remove a small amount of solids. The filtrate was then poured into a flange flask and water (25 vol) was added. The mixture was then adjusted to pH 3 with 2M HCl (approx 800-850 ml) (turns very thick). The aqueous was then filtered and the pale yellow solid washed with water, sucked dry overnight, and washed with acetonitrile and finally 1:1 acetonotrile/diethyl ether and dried under vacuum at 50° C. for 72 hours (weekend) to give 4-[4-(2-adamantylcarbamoyl)-5-tertbutyl-pyrazol-1-yl]benzoic acid (80%) as a solid.

Approximately 50 mg of 4-[4-(2-adamantylcarbamoyl)-5-tertbutyl-pyrazol-1-yl]benzoic acid as prepared above (Form 1) was placed in a vial with a magnetic flea, and approximately 2 ml of acetonitrile added. The vial was then sealed tightly with a cap. The slurry was then left to stir in a heated stirrer block with magnetic stirring capabilities at 50° C. After 3 days, the sample was removed from the plate, the cap taken off and the slurry left to dry under ambient conditions before it was analysed by XRPD and DSC. This form (Form 2) was determined to be crystalline by XRPD and seen to be different to the previous form. This material had a melting point of 310.3° C. (onset). It had 2 theta peaks measured using CuKa radiation at 18.0 and 17.7.

Approximately 20 mg of 4-[4-(2-adamantylcarbamoyl)-5-tertbutyl-pyrazol-1-yl]benzoic acid (form 1) was placed in a vial with a magnetic flea, and approximately 2 ml of methanol added, the vial was then sealed tightly with a cap and left to stir on a magnetic stirrer plate. After 3 days, the sample was removed from the plate, the cap taken off and the slurry left to dry under ambient conditions before it was analysed by XRPD and DSC. This form (Form 3) was determined to be crystalline by XRPD and seen to be different to previously seen forms. This material had a melting point of 309.4° C. (onset). It had 2 theta peaks measured using CuKa radiation at 18.7 and 11.7.

Approximately 20 mg of 4-[4-(2-adamantylcarbamoyl)-5-tertbutyl-pyrazol-1-yl]benzoic acid as Form 1 and 20 mg of the Form 3 material was placed in a vial with a magnetic flea, and approximately 2 ml of ethyl acetate added, the vial was then sealed tightly with a cap and left to stir on a magnetic stirrer plate. After 3 days, the sample was removed from the plate, the cap taken off and the slurry left to dry under ambient conditions before it was analysed by XRPD and DSC. This form (Form 4) was determined to be crystalline by XRPD and seen to be different to previously seen forms. This material (Form 4) had a melting point of 309.1° C. (onset).). It had 2 theta peaks measured using CuKa radiation at 16.2 and 20.6
4-[4-(2-Adamantylcarbamoyl)-5-tertbutyl-pyrazol-1-yl]benzoic acid as prepared above (Form 1) was suspended in acetonitrile (7 vol), seeded with 5 g of (form 4) and slurried at reflux for 3 days (jacket temperature 85° C.). A sample was taken and checked by DSC (shows 2 peaks). The sample was stirred at reflux for a further 3 days (weekend), cooled to 20° C., filtered, washed through with acetonitrile then diethyl ether, sucked dry and dried under vacuum at 50° C. for 48 hours to give a pale yellow solid (Form 4) (960 g, 90%).

Example 23

4-[4-(2-Adamantylcarbamoyl)-5-(1-methylcyclopropyl)pyrazol-1-yl]benzoic acid

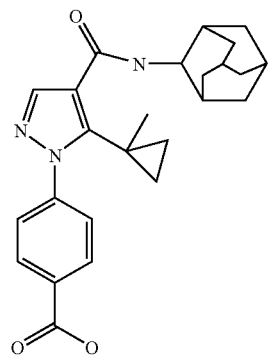

A solution of aqueous 2N sodium hydroxide (8.45 mL, 16.90 mmol) was added to a stirred solution of methyl 4-[4-(2-adamantylcarbamoyl)-5-(1-methylcyclopropyl)pyrazol-1-yl]benzoate (Intermediate#57), 1.221 g, 2.82 mmol) in methanol (25 mL) at room temperature. The resulting solution was stirred at 70° C. for 1 hour, and at room temperature overnight.

The reaction mixture was evaporated to dryness and re-dissolved in water (15 mL) and acidified with 2M HCl (10 mL). The reaction mixture was then extracted into EtOAc (75 mL), and washed sequentially with water (10 mL), and saturated brine (10 mL). The organic layer was dried over MgSO4, filtered and evaporated to afford 4-[4-(2-adamantylcarbamoyl)-5-(1-methylcyclopropyl)pyrazol-1-yl]benzoic acid (1.055 g, 89%) as a white solid.
m/z (ESI+) (M+H)+==420; HPLC $t_R$=2.56 min
1H NMR (400.13 MHz, DMSO-$d_6$) δ 0.51-0.53 (2H, m), 0.68-0.69 (2H, m), 1.54-1.58 (5H, m), 1.73 (2H, s), 1.84-1.87 (6H, m), 1.95-1.99 (2H, m), 2.06 (2H, d), 4.03-4.09 (1H, m), 7.44 (1H, d), 7.67 (2H, d), 8.06 (1H, s), 8.11 (2H, d), 13.16 (1H, s)

Example 24

4-[4-(2-Adamantylcarbamoyl)-5-cyclopentyl-pyrazol-1-yl]benzoic acid

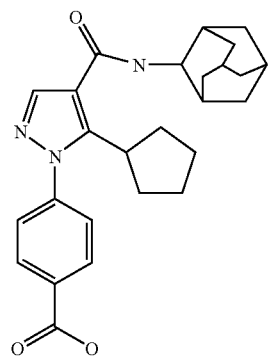

A solution of aqueous 2N sodium hydroxide (4.10 mL, 8.19 mmol) was added to a stirred solution of methyl 4-[4-

(2-adamantylcarbamoyl)-5-cyclopentyl-pyrazol-1-yl]benzoate (Intermediate#62) 611 mg, 1.37 mmol) in methanol (15 mL) at room temperature. The resulting solution was stirred at 70° C. for 1 hour.

The reaction mixture was evaporated to dryness and redissolved in water (15 mL) and acidified with 2M HCl (6 mL). The suspension obtained was then filtered. The product recovered was washed with water (10 mL) and dried under vacuum to give 4-[4-(2-adamantylcarbamoyl)-5-cyclopentyl-pyrazol-1-yl]benzoic acid (576 mg, 97%) as a white solid.

1H NMR (400.13 MHz, DMSO-$d_6$) δ 1.43-1.55 (4H, m), 1.74-1.85 (12H, m), 1.94 (2H, s), 2.03-2.12 (4H, m), 2.99-3.08 (1H, m), 3.98-4.03 (1H, m), 7.53-7.55 (2H, m), 7.74 (1H, d), 8.09 (1H, s), 8.10-8.12 (2H, m), 13.30 (1H, s)

m/z (ESI+) (M+H)+=434; HPLC $t_R$=2.80 min.

The same process as used for Example#24 prepared the following examples from the appropriate intermediate.

| Structure | Ex | Name | $^1$H NMR δ | MS m/e MH$^+$ |
|---|---|---|---|---|
| 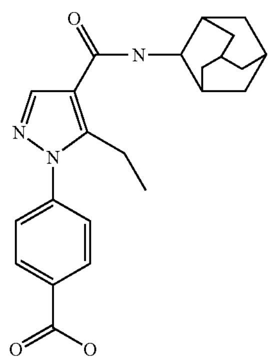 | 25 | 4-[4-(2-adamantylcarbamoyl)-5-ethylpyrazol-1-yl]benzoic acid | 1H NMR (400.13 MHz, DMSO-$d_6$) δ 1.03 (3 H, t), 1.53 (2 H, d), 1.72 (2 H, s), 1.78-1.85 (6 H, m), 1.95 (2 H, s), 2.11 (2 H, d), 2.97 (2 H, q), 4.04 (1 H, t), 7.58-7.63 (3 H, m), 8.09-8.13 (2 H, m), 8.28 (1 H, s) | 394 |
| 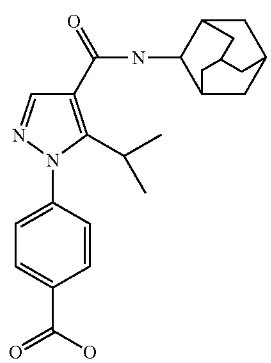 | 26 | 4-[4-(2-adamantylcarbamoyl)-5-propan-2-ylpyrazol-1-yl]benzoic acid | 1H NMR (400.13 MHz, DMSO-$d_6$) δ 1.29 (6 H, d), 1.52 (2 H, d), 1.73 (2 H, s), 1.82 (5 H, s), 1.86 (1 H, s), 1.98 (2 H, s), 2.11 (2 H, d), 3.10-3.17 (1 H, m), 4.02-4.05 (1 H, m), 7.54 (2 H, d), 7.67 (1 H, d), 8.07 (1 H, s), 8.11 (2 H, d), 13.20 (1 H, s) | 408 |
| 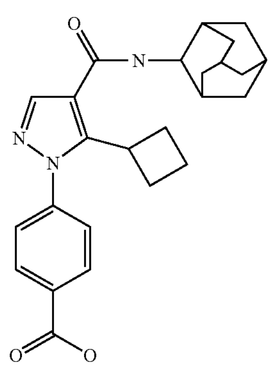 | 27 | 4-[4-(2-adamantylcarbamoyl)-5-cyclobutylpyrazol-1-yl]benzoic acid | 1H NMR (400.13 MHz, DMSO-$d_6$) δ 1.52 (2 H, d), 1.65 (1 H, q), 1.72 (2 H, s), 1.80-1.85 (7 H, m), 1.96 (2 H, s), 2.03-2.13 (4 H, m), 2.20-2.28 (2 H, m), 3.76-3.85 (1 H, m), 4.01-4.06 (1 H, m), 7.52 (2 H, d), 7.80 (1 H, d), 7.93 (1 H, s), 8.07 (2 H, d), 13.40 (1 H, s) | 420 |

Example 28

4-[4-(2-Adamantylcarbamoyl)-5-methyl-pyrazol-1-yl]benzoic acid

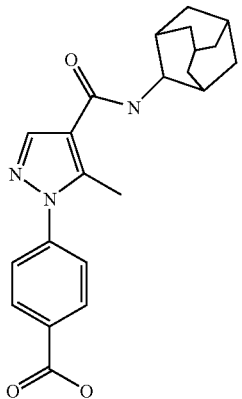

A solution of 1M sodium hydroxide (24.28 mL, 24.28 mmol) was added to a stirred suspension of N-(2-adamantyl)-1-(4-cyanophenyl)-5-methyl-pyrazole-4-carboxamide (Intermediate#66) (1.25 g, 3.47 mmol) in dioxane (25 mL). The resulting suspension was stirred at 100° C. for 7 hours. The reaction mixture was concentrated, diluted with water (40 mL) and filtered through Celite. The filtrates were acidified with 1M citric acid. The precipitate was recovered by filtration, washed with water (3×20 mL) and dried under vacuum at 50° C. The crude product was purified by preparative HPLC (Phenomenex Gemini C18 110A (axia) column, 5μ silica, 30 mm diameter, 100 mm length), using decreasingly polar mixtures of water (containing 1% formic acid) and MeCN as eluents. Fractions containing the desired compound were evaporated to dryness to afford 4-[4-(2-adamantylcarbamoyl)-5-methyl-pyrazol-1-yl]benzoic acid (550 mg, 42%) as a pale yellow powder.

1H NMR (400.13 MHz, DMSO-$d_6$) δ 1.45-1.54 (2H, m), 1.70-1.88 (8H, m), 1.90-2.00 (2H, m), 2.05-2.18 (2H, m), 2.56 (3H, s), 4.00-4.10 (1H, m), 7.57 (1H, d), 7.67 (2H, d), 8.11 (2H, d), 8.29 (1H, s), 13.25 (1H, s).

m/z (ESI+) (M+H)+=380;

Example 29

4-(5-tert-Butyl-4-(cyclohexylcarbamoyl)-1H-pyrazol-1-yl)benzoic acid

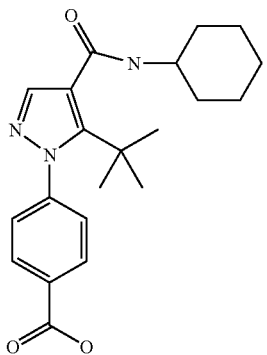

1-(4-bromophenyl)-5-tert-butyl-N-cyclohexyl-1H-pyrazole-4-carboxamide (Intermediate#82) (132 mg, 0.33 mmol), molybdenum hexacarbonyl (43.1 mg, 0.16 mmol), trans-Di(-acetato)bis[o-(di-o-tolylphosphino)benzyl]dipalladium (II) (15.34 mg, 0.02 mmol), 4-Dimethylaminopyridine (80 mg, 0.65 mmol) and N-Ethyldiisopropylamine (0.113 mL, 0.65 mmol) were suspended in Dioxane (4 mL) and Water (1 mL) and sealed into a microwave tube. The reaction was heated to 150° C. for 1 hour in the microwave reactor and cooled to RT. The reaction mixture was diluted with DCM (20 mL) and water (10 mL) and then adjusted to pH3 with 2M HCl and filtered through celite. The organic layer was separated, dried over MgSO4, filtered and evaporated to afford crude product.

The crude product was purified by preparative reverse phase HPLC using decreasingly polar mixtures of water (containing 0.1% NH3) and MeCN as eluents. Fractions containing the desired compound were evaporated to dryness to afford 4-(5-tert-butyl-4-(cyclohexylcarbamoyl)-1H-pyrazol-1-yl)benzoic acid (18 mg, 14.92%) as a white solid.

1H NMR (400.13 MHz, DMSO-d6) δ 1.15 (1H, s), 1.20 (9H, s), 1.25-1.4 (4H, m), 1.58 (1H, s), 1.71-1.74 (2H, m), 1.82 (2H, d), 3.18 (1H, s), 7.48-7.50 (2H, m), 7.60 (1H, s), 8.05-8.10 (3H, m)

m/z (ESI+) (M+H)+=370

Example 30

4-[4-(2-Adamantylcarbamoyl)-5-cyclohexylsulfanyl-pyrazol-1-yl]benzoic acid

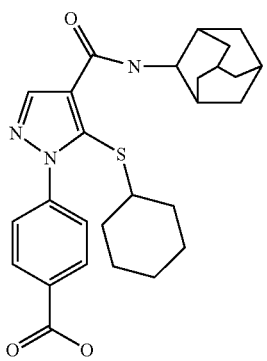

2M aqueous sodium hydroxide (1.671 mL, 3.34 mmol) was added in one portion to methyl 4-[4-(2-adamantylcarbamoyl)-5-cyclohexylsulfanyl-pyrazol-1-yl]benzoate (Intermediate#84) (330 mg, 0.67 mmol) in methanol (10 mL). The resulting mixture was stirred at 20° C. for 18 hours. The reaction mixture was concentrated and diluted with water (50 mL), and washed with ether (20 mL). The aqueous solution was adjusted to pH 3 with 2M HCl and extracted with EtOAc (2×25 mL), and the combined extracts washed sequentially with water (2×20 mL) and saturated brine (20 mL). The organic layer was dried over MgSO4, filtered and evaporated to afford 4-[4-(2-adamantylcarbamoyl)-5-cyclohexylsulfanyl-pyrazol-1-yl]benzoic acid (321 mg, 100%).

1H NMR (400.13 MHz, DMSO-d6) δ 1.01-1.11 (5H, m), 1.41 (1H, s), 1.50-1.57 (4H, m), 1.64 (2H, d), 1.75 (2H, s), 1.85 (6H, s), 1.93-2.05 (4H, m), 2.94 (1H, s), 4.12 (1H, d), 7.72-7.76 (2H, m), 8.05 (1H, d), 8.10-8.13 (2H, m), 8.18 (1H, s), 13.20 (1H, s)

m/z (ESI+) (M+H)+=480

The following Examples were prepared in a similar manner to Example #30, using an appropriate ester starting material

| Structure | Ex | Name | ¹H NMR δ | MS m/e |
|---|---|---|---|---|
| 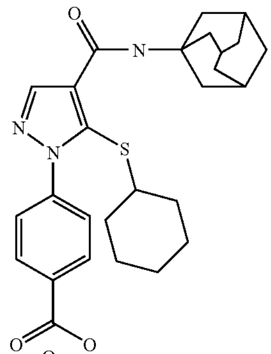 | 31 | 4-[4-(1-adamantylcarbamoyl)-5-cyclohexylsulfanyl-pyrazol-1-yl]benzoic acid | 1H NMR (400.13 MHz, DMSO-d6) δ 1.05-1.18 (5 H, m), 1.42 (1 H, s), 1.56 (4 H, d), 1.68 (6 H, s), 2.07 (9 H, s), 2.98 (1 H, s), 7.53 (1 H, s), 7.68-7.71 (2 H, m), 8.09-8.11 (3 H, m), 13.19 (1 H, s) | (M − H)− 478 |
| 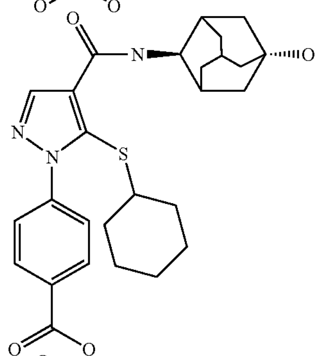 | 32 | 4-[5-cyclohexylsulfanyl-4-[(5-hydroxy-2-adamantyl)carbamoyl]pyrazol-1-yl]benzoic acid | 1H NMR (400.13 MHz, DMSO-d6) δ 1.03-1.08 (5 H, m), 1.41-1.56 (7 H, m), 1.67 (4 H, d), 1.76 (2 H, d), 1.89 (2 H, d), 2.08 (3 H, s), 2.93 (1 H, s), 4.03 (1 H, d), 4.43 (1 H, s), 7.73 (2 H, d), 7.97 (1 H, d), 8.10-8.12 (2 H, m), 8.18 (1 H, s), 13.25 (1 H, s) | (M + H)+ 496 |
| 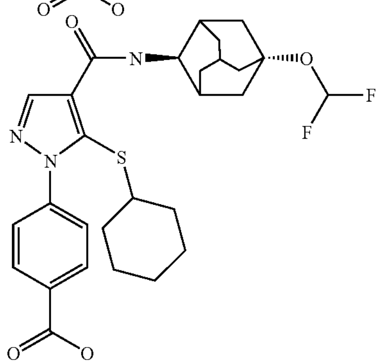 | 33 | 4-[5-cyclohexylsulfanyl-4-[[5-(difluoromethoxy)-2-adamantyl]carbamoyl]pyrazol-1-yl]benzoic acid | 1H NMR (400.13 MHz, DMSO-d6) δ 1.03-1.08 (5 H, m), 1.41-1.54 (7 H, m), 1.93 (6 H, d), 2.05 (2 H, d), 2.18 (3 H, d), 2.96 (1 H, d), 4.10 (1 H, t), 6.88 (1 H, t), 7.73 (2 H, d), 7.99 (1 H, d), 8.12 (2 H, d), 8.18 (1 H, s), 13.20 (1 H, s) | (M + H)+ 546 |

Example 34

4-[4-(2-Adamantylcarbamoyl)-5-cyclopentylsulfanyl-pyrazol-1-yl]benzoic acid

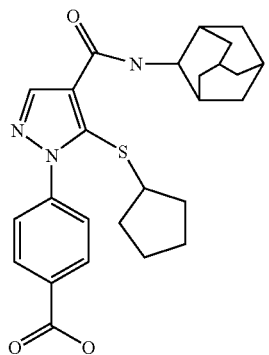

2M aqueous sodium hydroxide (1.694 mL, 3.39 mmol) was added in one portion to methyl 4-[4-(2-adamantylcarbamoyl)-5-cyclopentylsulfanyl-pyrazol-1-yl]benzoate (Intermediate #90) (325 mg, 0.68 mmol) in methanol (10 mL). The resulting mixture was stirred at 20° C. for 18 hours. The reaction mixture was concentrated and diluted with water (50 mL), and washed with ether (20 mL). The aqueous solution was adjusted to pH 3 with 2M HCl and extracted with EtOAc (2×25 mL), and the combined extracts washed sequentially with water (2×20 mL) and saturated brine (20 mL). The organic layer was dried over MgSO4, filtered and evaporated to afford 4-[4-(2-adamantylcarbamoyl)-5-cyclopentylsulfanyl-pyrazol-1-yl]benzoic acid (307 mg, 97%).

1H NMR (400.13 MHz, DMSO-d6) δ 1.17-1.25 (2H, m), 1.41 (4H, d), 1.65 (4H, d), 1.74 (2H, s), 1.85 (6H, s), 1.96-2.02 (4H, m), 3.31-3.33 (1H, m), 4.12 (1H, d), 7.75-7.77 (2H, m), 8.08 (1H, d), 8.10-8.15 (2H, m), 8.19 (1H, s), 13.20 (1H, s)

m/z (ESI+) (M+H)+=466

The following Examples were prepared in a similar manner to Example #34, using an appropriate ester starting material

| Structure | Ex # | Name | ¹H NMR δ | MS m/e (M + H)+ |
|---|---|---|---|---|
| 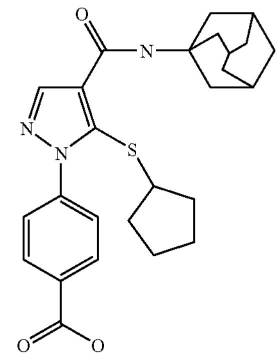 | 35 | methyl 4-[4-(1-adamantylcarbamoyl)-5-cyclopentylsulfanyl-pyrazol-1-yl]benzoate | 1H NMR (400.13 MHz, DMSO-d6) δ 1.18-1.28 (2 H, m), 1.41-1.49 (4 H, m), 1.64-1.71 (8 H, m), 2.07 (9 H, s), 3.32-3.37 (1 H, m), 7.54 (1 H, s), 7.70-7.73 (2 H, m), 8.09-8.13 (3 H, m), 13.20 (1 H, s) | 466 |
| 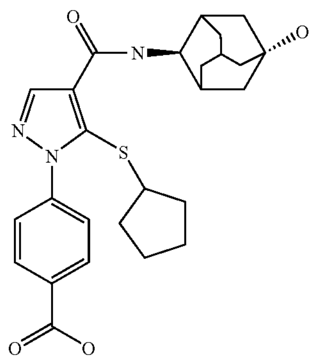 | 36 | methyl 4-[5-cyclopentylsulfanyl-4-[[(1R,3S)-5-hydroxy-2-adamantyl]carbamoyl]pyrazol-1-yl]benzoate | 1H NMR (400.13 MHz, DMSO-d6) δ 1.17-1.25 (2 H, m), 1.36-1.47 (6 H, m), 1.65 (6 H, d), 1.76 (2 H, d), 1.89 (2 H, d), 2.08 (3 H, s), 3.35 (1 H, d), 4.02-4.05 (1 H, m), 4.43 (1 H, s), 7.74-7.77 (2 H, m), 7.99 (1 H, d), 8.10-8.13 (2 H, m), 8.18 (1 H, s) | 482 |

Example 37

4-[4-[[5-(Difluoromethoxy)-2-adamantyl]carbamoyl]-5-propylsulfanylpyrazol-1-yl]benzoic acid

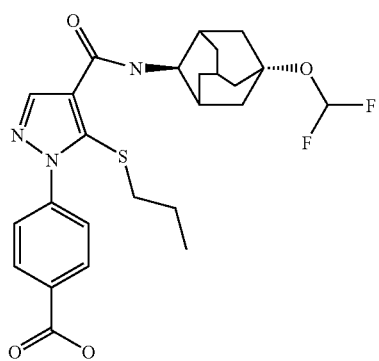

2M aqueous sodium hydroxide (2.050 mL, 4.10 mmol) was added in one portion to methyl 4-[4-[[5-(difluoromethoxy)-2-adamantyl]carbamoyl]-5-propylsulfanylpyrazol-1-yl]benzoate (Intermediate#95) (459 mg, 0.82 mmol) in methanol (10 mL). The resulting mixture was stirred at 20° C. for 18 hours and then a further 4 hours at 55° C. The reaction mixture was concentrated and diluted with water (50 mL), and washed with ether (20 mL). The aqueous solution was adjusted to pH 3 with 2M HCl and extracted with EtOAc (2×25 mL), and the combined extracts washed sequentially with water (2×20 mL) and saturated brine (20 mL). The organic layer was dried over MgSO4, filtered and evaporated to afford 4-[4-[[5-(difluoromethoxy)-2-adamantyl]carbamoyl]-5-propylsulfanylpyrazol-1-yl]benzoic acid (284 mg, 63.5%).

1H NMR (400.13 MHz, DMSO-d6) δ 1.03-1.08 (5H, m), 1.41-1.54 (7H, m), 1.93 (6H, d), 2.05 (2H, d), 2.18 (3H, d), 2.96 (1H, d), 4.10 (1H, t), 6.88 (1H, t), 7.73 (2H, d), 7.99 (1H, d), 8.12 (2H, d), 8.18 (1H, s), 13.20 (1H, s)

m/z (ESI+) (M+H)+=506

Example 38

4-[4-(Cyclohexylcarbamoyl)-5-cyclopentylsulfanyl-pyrazol-1-yl]benzoic acid

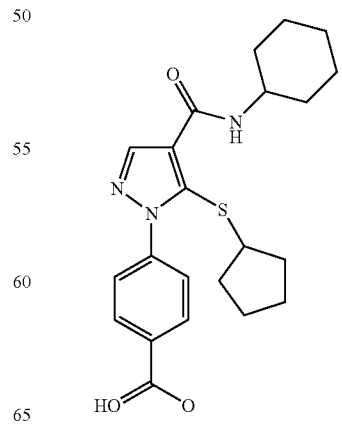

A solution of aqueous 2N sodium hydroxide (4 mL, 8 mmol) was added to a stirred solution of methyl 4-[4-(cyclohexylcarbamoyl)-5-cyclopentylsulfanyl-pyrazol-1-yl]benzoate (Intermediate#96), 233 mg, 0.55 mmol) in methanol (7 mL) at room temperature. The resulting solution was stirred at room temperature overnight.

The reaction mixture was evaporated to dryness and redissolved in water (15 mL) and acidified with 2M HCl (6 mL). The reaction mixture was then extracted in EtOAc (30 mL), and washed sequentially with water (10 mL), and saturated brine (10 mL). The organic layer was dried over MgSO4, filtered and evaporated to afford 4-[4-(cyclohexylcarbamoyl)-5-cyclopentylsulfanyl-pyrazol-1-yl]benzoic acid (217 mg, 96%) as a white solid.

m/z (ESI+) (M+H)+=414

1H NMR (400.13 MHz, DMSO-$d_6$) δ 1.21-1.45 (11H, m), 1.58-1.74 (5H, m), 1.84-1.87 (2H, m), 3.42-3.48 (1H, m), 3.76-3.82 (1H, m), 7.70 (2H, d), 7.90-7.92 (1H, d), 8.11 (2H, d), 8.16 (1H, s), 13.19 (1H, s)

Example 39

4-[4-(Cyclohexylcarbamoyl)-5-cyclohexylsulfanyl-pyrazol-1-yl]benzoic acid

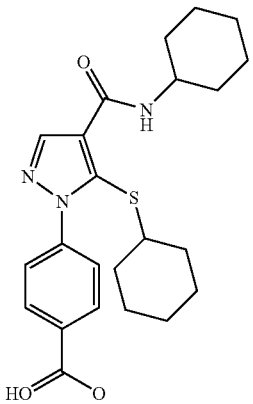

4-[4-(cyclohexylcarbamoyl)-5-cyclohexylsulfanyl-pyrazol-1-yl]benzoic acid was prepared from methyl 4-[4-(cyclohexylcarbamoyl)-5-cyclohexylsulfanylpyrazol-1-yl]benzoate (Intermediate#97) by the same process used for Example#38 m/z (ESI+) (M+H)+=428; HPLC $t_R$=2.67 min.

1H NMR (400.13 MHz, DMSO-$d_6$) δ 1.09 (4H, m), 1.19-1.30 (2H, m), 1.33-1.41 (5H, m), 1.51-1.58 (5H, m), 1.71-1.75 (2H, m), 1.84-1.87 (2H, m), 3.03-3.12 (1H, m), 3.72-3.80 (1H, m), 7.71 (2H, d), 7.89-7.90 (1H, d), 8.09-8.11 (2H, m), 8.16 (1H, s), 13.20 (1H, s)

Example 40

4-[5-Cycloheptylsulfanyl-4-(cyclohexylcarbamoyl)pyrazol-1-yl]benzoic acid

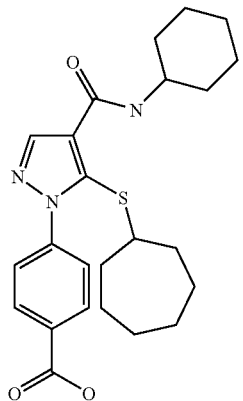

4-[5-cycloheptylsulfanyl-4-(cyclohexylcarbamoyl)pyrazol-1-yl]benzoic acid was prepared from methyl 4-[5-cycloheptylsulfanyl-4-(cyclohexylcarbamoyl)pyrazol-1-yl]benzoate (Intermediate#98) by the same process used for Example#38.

m/z (ESI+) (M+H)+=442

1H NMR (400.13 MHz, DMSO-d6) δ 1.16-1.52 (15H, m), 1.58-1.67 (3H, m), 1.71-1.75 (2H, m), 1.84-1.87 (2H, m), 3.30 (1H, m), 3.78-3.81 (1H, m), 7.67-7.70 (2H, d), 7.90 (1H, d), 8.09-8.12 (2H, d), 8.16 (1H, s), 13.18 (1H, s)

Example 41

4-[4-(2-Adamantylcarbamoyl)-5-ethylsulfanyl-pyrazol-1-yl]benzoic acid

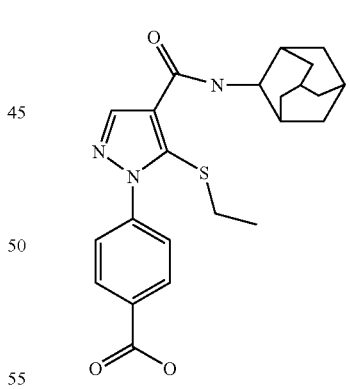

2M aqueous sodium hydroxide (2.446 mL, 4.89 mmol) was added in one portion to methyl 4-[4-(2-adamantylcarbamoyl)-5-ethylsulfanyl-pyrazol-1-yl]benzoate (Intermediate#99) (430 mg, 0.98 mmol) in methanol (20 mL). The resulting mixture was stirred at 20° C. for 18 hours. The reaction mixture was concentrated, diluted with water (50 mL) and adjusted to pH 3 with 2M HCl. The precipitate was collected by filtration, washed with water (20 mL) and dried under vacuum to afford 4-[4-(2-adamantylcarbamoyl)-5-ethylsulfanyl-pyrazol-1-yl]benzoic acid (383 mg, 92%) as a white solid.

1H NMR (400.13 MHz, DMSO-d$_6$) δ 0.94 (3H, t), 1.63 (2H, d), 1.74 (2H, s), 1.86 (6H, d), 1.99 (4H, d), 2.68 (2H, q), 4.11 (1H, t), 7.72-7.76 (2H, m), 8.04 (1H, d), 8.10-8.13 (2H, m), 8.19 (1H, s), 13.2 (1H, s)

m/z (ESI+) (M+H)+=426

Example 42

4-[4-(2-Adamantylcarbamoyl)-5-methylsulfanyl-pyrazol-1-yl]benzoic acid

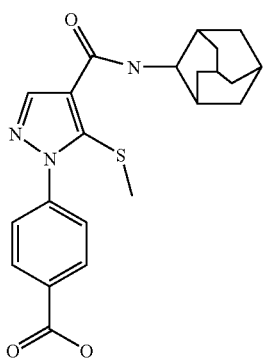

Prepared from methyl 4-[4-(2-adamantylcarbamoyl)-5-methylsulfanyl-pyrazol-1-yl]benzoate (Intermediate#100) by the same process as Example#41.

1H NMR (400.13 MHz, DMSO-d$_6$) δ 1.61 (2H, d), 1.74 (2H, s), 1.86 (6H, d), 2.00 (4H, d), 2.30 (3H, s), 4.11 (1H, t), 7.72-7.75 (2H, m), 8.01-8.04 (1H, m), 8.10-8.14 (2H, m), 8.19 (1H, s), 13.2 (1H, s)

m/z (ESI+) (M+H)+=412

Example 43

4-[4-(5-Methanesulfonyl-adamantan-2-ylcarbamoyl)-5-propylsulfanyl-pyrazol-1-yl]-benzoic acid

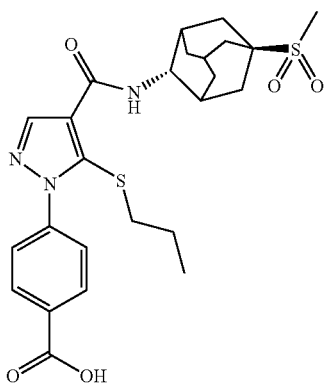

Lithium hydroxide monohydrate (27.5 mg, 0.65 mmol) was added to a suspension of 4-[4-(5-Methanesulfonyl-adamantan-2-ylcarbamoyl)-5-propylsulfanyl-pyrazol-1-yl]-benzoic acid methyl ester (Intermediate#105) (116 mg, 0.22 mmol) in methanol (4 mL)/water (2 mL) at ambient temperature. The resulting suspension was stirred at ambient temperature for 18 hours. The bulk of the organic solvent was removed in vacuo and the resulting solution was diluted with water (10 mL) and washed with ether (10 mL). The aqueous layer was acidified to ~pH4 with 2M HCl then extracted with EtOAc (3×25 ml). The EtOAc layers were combined, washed sequentially with water (5 mL) and saturated brine (10 mL). The organic layer was dried over MgSO4, filtered and evaporated to afford 4-[4-(5-Methanesulfonyl-adamantan-2-ylcarbamoyl)-5-propylsulfanyl-pyrazol-1-yl]-benzoic acid (113 mg, 100%) as a white solid.

1H NMR (400.13 MHz, DMSO-d6) δ 0.68 (3H, t), 1.22-1.31 (2H, m), 1.57 (2H, d), 1.96 (2H, s), 2.00-2.16 (7H, m), 2.20 (2H, s), 2.65 (2H, t), 2.87 (3H, s), 4.09 (1H, m), 7.74 (2H, d), 8.05 (1H, d), 8.12 (2H, m), 8.19 (1H, s), 13.20 (1H, s)

MS m/e MH+ 518.

Example 44

4-[4-(2-Adamantylcarbamoyl)-5-propylsulfanyl-pyrazol-1-yl]-2-methoxy-benzoic acid

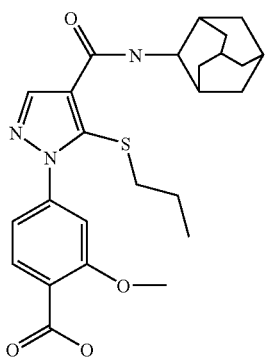

2M aqueous sodium hydroxide (1.256 mL, 2.51 mmol) was added in one portion to methyl 4-[4-(2-adamantylcarbamoyl)-5-propylsulfanyl-pyrazol-1-yl]-2-methoxy-benzoate (Intermediate#106) (243 mg, 0.50 mmol) in methanol (10 mL). The resulting mixture was stirred at 20° C. for 18 hours.

The reaction mixture was concentrated, diluted with water (50 mL) and adjusted to pH 3 with 2M HCl. The precipitate was collected by filtration, washed with water (20 mL) and dried under vacuum to afford 4-[4-(2-adamantylcarbamoyl)-5-propylsulfanyl-pyrazol-1-yl]-2-methoxy-benzoic acid (202 mg, 86%) as a white solid.

1H NMR (400.13 MHz, DMSO-d$_6$) δ 0.70 (3H, t), 1.23-1.32 (2H, m), 1.62 (2H, d), 1.74 (2H, s), 1.86 (6H, d), 1.92-2.05 (4H, m), 2.65 (2H, t), 3.87 (3H, s), 4.11 (1H, d), 7.23-7.25 (1H, m), 7.39 (1H, d), 7.81 (1H, d), 8.09 (1H, d), 8.17 (1H, s), 12.92 (1H, s)

m/z (ESI+) (M+H)+=470

Example 45

4-[4-(2-Adamantylcarbamoyl)-5-tert-butyl-pyrazol-1-yl]-3-methyl-benzoic acid

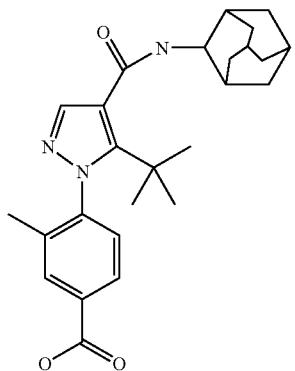

A solution of Sodium hydroxide (1.904 mL, 3.81 mmol) was added in one portion to a stirred solution of ethyl 4-[4-(2-adamantylcarbamoyl)-5-tert-butyl-pyrazol-1-yl]-3-methyl-benzoate (Intermediate#113) (353 mg, 0.76 mmol) in methanol (6 mL). The resulting suspension was stiffed at 20° C. for 16 hours. The resulting mixture was evaporated to remove the methanol and washed with ether (20 mL). The reaction mixture was acidified with 2M HCl. The precipitate was collected by filtration, washed with water (10 mL) and dried under vacuum to afford 4-[4-(2-adamantylcarbamoyl)-5-tert-butyl-pyrazol-1-yl]-3-methyl-benzoic acid (266 mg, 80%) as a white solid.

$^1$H NMR (300.073 MHz, dmso) δ 1.16 (s, 9H), 1.50 (d, J=12.6 Hz, 2H), 1.70 (s, 2H), 1.74-1.88 (m, 6H), 1.89-1.99 (m, 2H), 2.01-2.14 (m, 5H), 3.99 (d, 1H), 7.37 (d, 1H), 7.66 (s, 1H), 7.86 (d, 1H), 7.94 (s, 1H), 8.05 (d, 1H)

m/z (ESI+) (M+H)+=436

Example 46

4-[4-(2-Adamantylcarbamoyl)-5-tert-butyl-pyrazol-1-yl]-2-(trifluoromethyl)benzoic acid

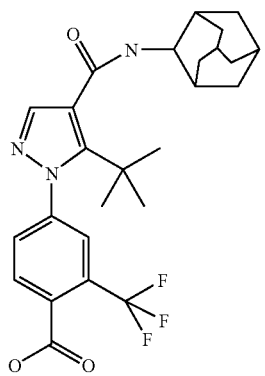

4-[4-(2-adamantylcarbamoyl)-5-tert-butyl-pyrazol-1-yl]-2-(trifluoromethyl)benzoic acid was prepared from ethyl 4-[4-(2-adamantylcarbamoyl)-5-tert-butyl-pyrazol-1-yl]-3-methyl-benzoate (Intermediate#117) by the same process used for Example#45.

1H NMR (400.13 MHz, CDCl$_3$) δ 1.29 (9H, s), 1.71-1.79 (6H, m), 1.91 (6H, s), 2.07 (2H, s), 4.24 (1H, d), 6.20 (1H, d), 7.63-7.66 (1H, m), 7.70 (1H, s), 7.79-7.80 (1H, m), 8.00 (1H, d)

MS m/z (ESI+) (M+H)+=490.

Example 47

4-[4-(Adamantan-2-ylcarbamoyl)-5-(trifluoromethyl)-1H-pyrazol-1-yl]benzoic acid

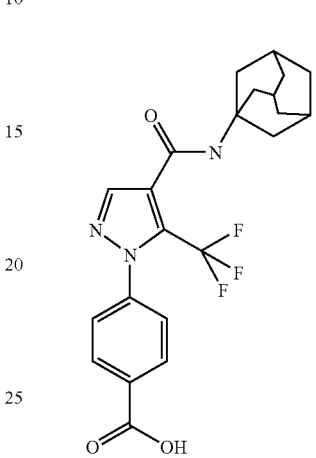

A solution of Sodium hydroxide (1.056 mL, 2.11 mmol) was added in one portion to a stirred solution of N-adamantan-2-yl-1-(4-cyanophenyl)-5-(trifluoromethyl)-1H-pyrazole-4-carboxamide (Intermediate#124) (250 mg, 0.60 mmol), in methanol (10 mL) under air. The resulting solution was stirred at 65° C. for 45 hours. The resulting mixture was evaporated to dryness and the residue dissolved in ice/water (25 mL) and the mixture was acidified with 2M HCl. The precipitate was collected by filtration, washed with water (25 mL) and dried under vacuum to afford 4-[4-(adamantan-2-ylcarbamoyl)-5-(trifluoromethyl)-1H-pyrazol-1-yl]benzoic acid (243 mg, 93%) as a white solid, which was used without further purification.

m/z (ESI+) (M+H)+=434; HPLC t$_R$=2.57 min.

1H NMR (400.13 MHz, DMSO-d$_6$) δ 1.49-1.53 (2H, m), 1.71 (2H, s), 1.80 (5H, s), 1.84 (1H, s), 1.93 (2H, s), 2.05 (2H, d), 3.98-4.05 (1H, m), 7.63 (2H, d), 8.11-8.14 (3H, m), 8.34 (1H, d), 13.30 (1H, s)

Intermediate#1: 4-[4-((1R,2S,3S,5S)-5-Hydroxy-adamantan-2-ylcarbamoyl)-5-propylsulfanyl-pyrazol-1-yl]-benzoic acid methyl ester

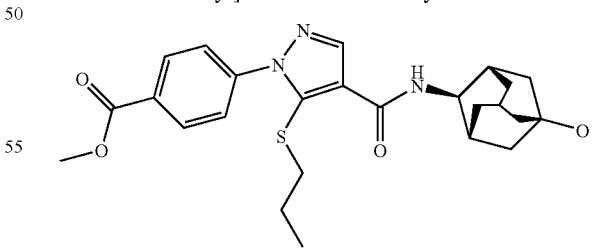

1-(4-methoxycarbonylphenyl)-5-propylsulfanyl-pyrazole-4-carboxylic acid (Intermediate#7) (160 mg, 0.5 mmol), (1S,3S,4S,5R)-4-Amino-adamantan-1-ol (84 mg, 0.5 mmol), HOBT (81 mg, 0.6 mmol), and DIPEA (174 μL, 1 mmol) were dissolved in DMF (5 mL) and treated at ambient temperature with EDCI (115 mg, 0.6 mmol). The mixture was stirred at ambient for 18 h and then diluted with ethyl acetate (50 mL), washed with water (3×20 mL) and brine, dried (MgSO₄) and evaporated to leave a brown gum, which was purified by chromatography on silica gel (12 silica 0-100% EtOAc/isohexane) to give the title compound (159 mg, 69%)

¹H NMR (300.073 MHz, DMSO-d₆) δ0.65 (3H, t), 1.17-1.29 (2H, m), 1.42 (2H, d), 1.60-1.80 (6H, m), 1.89 (2H, d), 2.06 (3H, s), 2.62 (2H, t), 3.90 (3H, s), 4.00 (1H, d), 4.43 (1H, s), 7.76 (2H, d), 7.95 (1H, d), 8.13 (2H, d), 8.17 (1H, s)

MS m/z 470 M+H

Intermediate#2: Methyl 4-[4-(2-adamantylcarbamoyl)-5-propylsulfanyl-pyrazol-1-yl]benzoate

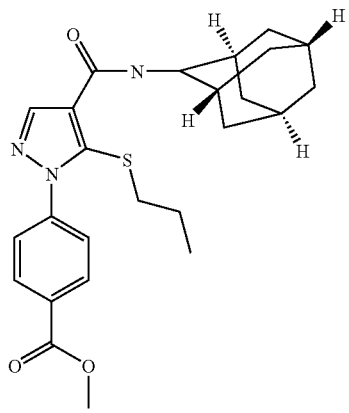

1-(4-methoxycarbonylphenyl)-5-propylsulfanyl-pyrazole-4-carboxylic acid (Intermediate #7) (160 mg, 0.5 mmol), 2-adamantylamine hydrochloride (94 mg, 0.5 mmol), HOBT (81 mg, 0.6 mmol) and DIPEA (261 µL, 1.5 mmol) were dissolved in DMF (5 mL) and treated at ambient temperature with EDCI (115 mg, 0.6 mmol). The mixture was stirred at ambient for 18 h and then diluted with ethyl acetate (50 mL), washed with water (3×20 mL) and brine, dried (MgSO₄) and evaporated to leave a white solid, which was purified by chromatography on silica gel, (12 g silica 0-50% EtOAc/isohexane) to give the title compound as a white solid. (203 mg, 92%)

¹H NMR (300.073 MHz, DMSO-d₆) δ0.65 (3H, t), 1.17-1.29 (2H, m), 1.60 (2H, d), 1.73 (2H, s), 1.83 (6H, s), 1.91-2.05 (4H, m), 2.62 (2H, t), 3.90 (3H, s), 4.09 (1H, d), 7.79 (2H, d), 8.03 (1H, d), 8.13 (2H, d), 8.16 (1H, s)

MS m/z 454 M+H

Intermediate#3: Methyl 4-[4-(1-adamantylcarbamoyl)-5-propylsulfanyl-pyrazol-1-yl]benzoate

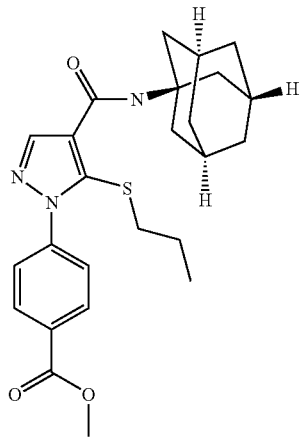

1-(4-methoxycarbonylphenyl)-5-propylsulfanyl-pyrazole-4-carboxylic acid (Intermediate #7) (160 mg, 0.5 mmol), 1-adamantylamine (76 mg, 0.5 mmol), HOBT (81 mg, 0.6 mmol) and DIPEA (174 µL, 1.0 mmol) were dissolved in DMF (5 mL) and treated at ambient temperature with EDCI (115 mg, 0.6 mmol). The mixture was stirred at ambient for 18 h and then diluted with ethyl acetate (50 mL), washed with water (3×20 mL) and brine, dried (MgSO₄) and volatiles removed by evaporation. The residue was purified by chromatography on silica gel (12 g silica 0-50% EtOAc/isohexane) to give the title compound as a colourless gum (143 mg, 63%).

MS m/z 454 M+H

Intermediate#4: Methyl 4-[4-(N-cyclohexyl-N-methyl-carbamoyl)-5-propylsulfanyl-pyrazol-1-yl]benzoate

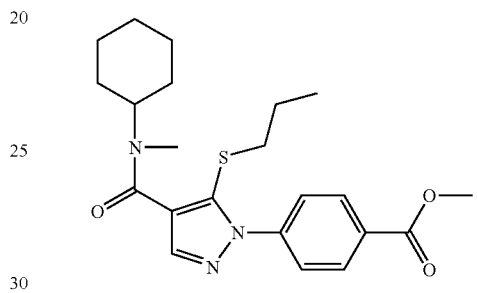

1-(4-methoxycarbonylphenyl)-5-propylsulfanyl-pyrazole-4-carboxylic acid (Intermediate #7), (160 mg, 0.5 mmol), N-methylcyclohexylamine (57 mg, 0.5 mmol), HOBT (81 mg, 0.6 mmol) and DIPEA (174 µL, 1.0 mmol) were dissolved in DMF (5 mL) and treated at ambient temperature with EDCI (115 mg, 0.6 mmol). The mixture was stirred at ambient for 18 h and then diluted with ethyl acetate (50 mL), washed with water (3×20 mL) and brine, dried (MgSO₄) and volatiles removed by evaporation. The residue was purified by chromatography on silica gel (12 g silica 0-70% EtOAc/isohexane) to give the title compound as a colourless gum (162 mg, 78%).

¹H NMR (300.073 MHz, DMSO-d₆) δ0.67 (3H, t), 1.01-1.41 (4H, m), 1.42-1.85 (8H, m), 2.58 (2H, t), 2.86 (3H, s), 3.40-3.60 (0.5H, m), 3.89 (3H, s), 4.20-4.40 (0.5H, m) 7.78 (2H, d), 7.91 (1H, s), 8.12 (2H, d)

MS m/z 416 M+H

Intermediate#5: Methyl 4-[4-(oxan-4-ylcarbamoyl)-5-propylsulfanyl-pyrazol-1-yl]benzoate

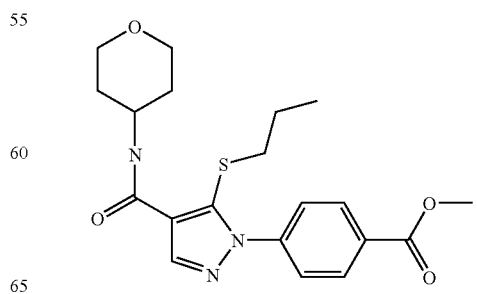

1-(4-methoxycarbonylphenyl)-5-propylsulfanyl-pyrazole-4-carboxylic acid (Intermediate #7), (160 mg, 0.5 mmol), 4-aminotetrahydropyran (61 mg, 0.5 mmol), HOBT (81 mg, 0.6 mmol) and DIPEA (174 μL, 1.0 mmol) were dissolved in DMF (5 mL) and treated at ambient temperature with EDCI (115 mg, 0.6 mmol). The mixture was stirred at ambient for 18 h and then diluted with ethyl acetate (50 mL), washed with water (3×20 mL) and brine, dried (MgSO₄) and volatiles removed by evaporation. The residue was purified by chromatography on silica gel (12 g silica, 0-100% EtOAc/isohexane) to give the title compound as a white solid (114 mg, 56%).

¹H NMR (300.073 MHz, DMSO-d₆) δ0.68 (3H, t), 1.18-1.30 (2H, m), 1.47-1.60 (2H, m), 1.77-1.81 (2H, m), 2.72 (2H, t), 3.36-3.43 (2H, m), 3.81-3.89 (5H, m), 3.95-4.05 (1H, m), 7.71 (2H, d), 8.04 (1H, d), 8.12 (2H, d), 8.17 (1H, s)

MS m/z 403 M+H

Intermediate#6: Methyl 4-[5-propylsulfanyl-4-[3-[2-(trifluoromethyl)phenyl]pyrrolidine-1-carbonyl]pyrazol-1-yl]benzoate

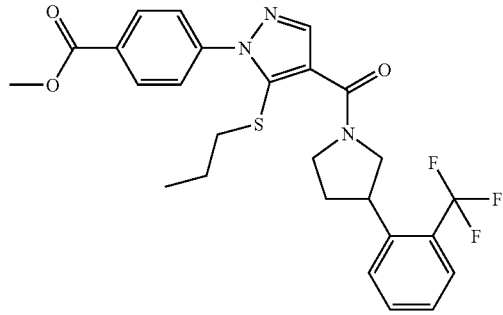

1-(4-methoxycarbonylphenyl)-5-propylsulfanyl-pyrazole-4-carboxylic acid (Intermediate #7) was dissolved in DCM (3 mL). 1 drop of DMF and oxalyl chloride (71 μL, 0.83 mmol) was added. The mixture was stirred at ambient temperature for 2 h and then volatiles were removed by evaporation under reduced pressure. The residue was dissolved in DCM (5 mL) and added to a solution of 3-[2-(trifluoromethyl)phenyl]pyrrolidine HCl (105 mg, 0.42 mmol) and DIPEA (217 μL, 1.25 mmol) in DCM (5 mL). Water (10 mL) was added and the mixture stirred vigorously and passed through a phase separating column. The filtrate was purified by chromatography on silica gel, eluting with 0-20% EtOAc/DCM to give the title compound as a clear colourless oil (177 mg, 81%).

MS m/z 518 M+H

Intermediate#7: 1-(4-methoxycarbonylphenyl)-5-propylsulfanyl-pyrazole-4-carboxylic acid

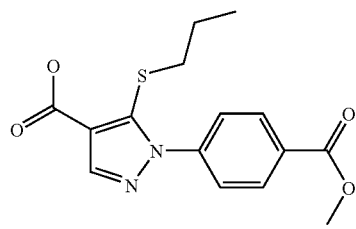

tert-butyl 1-(4-methoxycarbonylphenyl)-5-propylsulfanyl-pyrazole-4-carboxylate (Intermediate#8) (2.86 g, 7.97 mmol) was dissolved in DCM (40 mL) and TFA (10 mL) added, the mixture was stirred at ambient temperature for 3 h and then evaporated under reduced pressure to leave a light brown oil. Trituration of the oil with isohexane gave a light brown solid that was recovered by filtration and dried under vacuum to give the title compound. (2.23 g, 89%)

¹H NMR (300.073 MHz, DMSO-d₆) δ0.67 (3H, t), 1.20-1.32 (2H, m), 2.81 (2H, t), 3.90 (3H, s), 7.71 (2H, d), 8.12 (2H, d), 8.17 (1H, s), 12.73 (1H, s)

MS m/z 321 M+H

Intermediate#8: tert-butyl 1-(4-methoxycarbonylphenyl-1)-5-propylsulfanyl-pyrazole-4-carboxylate

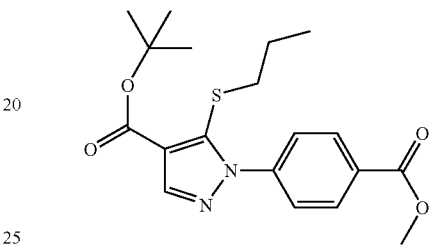

tert-butyl 5-chloro-1-(4-methoxycarbonylphenyl)pyrazole-4-carboxylate (Intermediate#9) (2.016 g, 6.0 mmol) was dissolved in butyronitrile (30 mL), potassium carbonate (2.48 g, 18 mmol) and propanethiol (678 μL, 7.5 mmol) were added and the mixture heated to reflux for 5 h. Ethyl acetate (150 mL) was added and the mixture washed with water (4×25 mL), dried (MgSO₄) and evaporated under reduced pressure. The residue was purified by chromatography on silica gel (120 g silica 0-25% EtOAc/isohexane) to give the title compound as a clear pale yellow oil that slowly crystallised on standing to a white solid. (2.01 g, 89%)

¹H NMR (300.073 MHz, DMSO-d₆) δ0.67 (3H, t), 1.25 (2H, q), 1.54 (9H, s), 2.76 (2H, t), 3.89 (3H, s), 7.70 (2H, d), 8.11 (3H, d)

MS m/z 321 M-tBut

Intermediate#9: tert-butyl 5-chloro-1-(4-methoxycarbonylphenyl)pyrazole-4-carboxylate

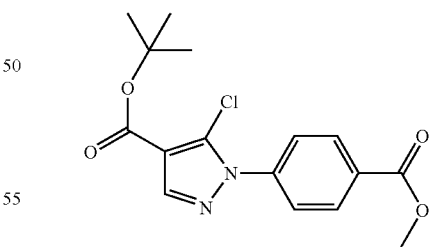

t-Butylnitrite (2.9 mL, 24.22 mmol) and cupric chloride (4.06 g, 30.27 mmol) were added to acetonitrile (150 mL) and heated to 65° C. Tert-butyl 5-amino-1-(4-methoxycarbonylphenyl)pyrazole-4-carboxylate (Intermediate#10) was added as a solid giving a vigorous gas evolution. After the addition was complete, heating was continued for a further 15 min. The reaction mixture was cooled to ambient, diluted with water (500 mL) and extracted with ethyl acetate (3×100 mL). The combined extracts were washed with water (2×100 mL) and brine (100 mL), dried (MgSO$_4$) and evaporated under reduced pressure. The residue was purified by chromatography on silica gel (120 g silica column, EtOAc/Hexane 0-50%) to give the title compound as an oil. (5.68 g, 83%)

$^1$H NMR (300.073 MHz, DMSO-d$_6$) δ1.53 (9H, s), 3.87-3.90 (3H, m), 7.78 (2H, d), 8.15 (2H, d), 8.20 (1H, s)

MS m/z 281 M-tBut

Intermediate#10 Tert-butyl 5-amino-1-(4-methoxy-carbonylphenyl)pyrazole-4-carboxylate

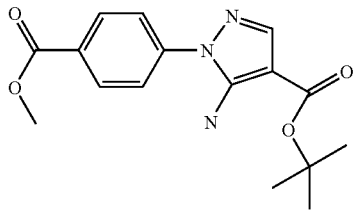

t-Butyl cyanoacetate (14.1 g, 100 mmol) was dissolved in triethyl orthoformate (24.8 mL, 150 mmol). Acetic anhydride (9.625 mL, 100 mL) was added and the mixture heated to 125° C. for 3 h and then volatiles were removed by evaporation under reduced pressure. The residue was dissolved in ethanol (100 mL) and methyl 4-hydrazinylbenzoate hydrochloride (Intermediate#123) (6.06 g, 30 mmol) and DIPEA (5.23 mL, 30 mmol) was added. The mixture was heated to reflux for 5 h and then evaporated under reduced pressure to leave a brown oil which was dissolved in ethyl acetate (300 mL) and washed with water (2×100 mL) and brine (100 mL), dried (MgSO$_4$) and evaporated. The residue was purified by chromatography on silica gel (120 g silica, EtOAc/Hexane 0-50%) to give the title compound as a yellow solid. (7.1 g)

$^1$H NMR (300.073 MHz, DMSO-d$_6$) δ1.51 (9H, s), 3.88 (3H, s), 6.43 (2H, s), 7.67 (1H, s), 7.73 (2H, s), 8.08 (2H, d)

MS m/z 262 M-tBut

Intermediate #11: Methyl 4-[4-(cyclohexylcarbamoyl)-5-propylsulfanyl-pyrazol-1-yl]benzoate

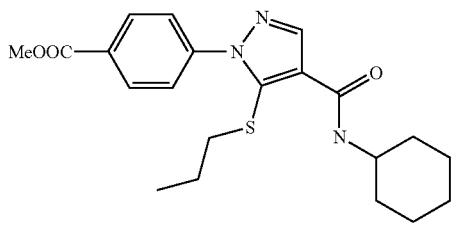

Propane thiol (88 mg, 1.16 mmol) was dissolved in DMF (5 mL) and treated at ambient temperature with a 1M solution of NaHMDS in THF (1.16 mL). After stiffing for 15 min the clear solution was added to a suspension of methyl 4-[5-chloro-4-(cyclohexylcarbamoyl)pyrazol-1-yl]benzoate (Intermediate#15) (378 mg, 1.05 mmol) in DMF (10 mL). Stiffing was continued at ambient temperature for 2 h and then the reaction mixture was diluted with ethyl acetate (100 mL), washed with water (4×25 mL) and dried (MgSO$_4$). Volatiles were removed by evaporation under reduced pressure to give a clear oil which was purified by chromatography on silica gel, eluting with an ethyl acetate/hexane gradient (0-50%) to give the title compound as a white solid. (363 mg, 86%)

$^1$H NMR (300.073 MHz, DMSO-d$_6$) δ0.67 (3H, t), 1.14-1.39 (7H, m), 1.59 (1H, d), 1.71-1.74 (2H, m), 1.84 (2H, d), 2.70 (2H, t), 3.74-3.79 (1H, m), 3.89 (3H, s), 7.72 (2H, d), 7.92 (1H, d), 8.10-8.16 (3H, m)

MS m/z 402 M+H

Intermediate #12: Methyl 3-[4-(cyclohexylcarbamoyl)-5-propylsulfanyl-pyrazol-1-yl]benzoate

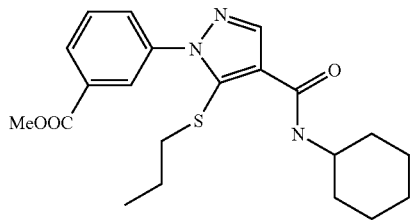

Propane thiol (48 mg, 0.57 mmol) was dissolved in DMF (3 mL) and treated at ambient temperature with a 1M solution of NaHMDS in THF (0.63 mL, 0.63 mmol). After stirring for 15 min a solution of methyl 3-[5-chloro-4-(cyclohexylcarbamoyl)pyrazol-1-yl]benzoate (Intermediate #19) (205 mg, 0.57 mmol) in DMF (5 mL) was added and stirring continued for 2 h. Ethyl acetate (50 mL) was added and the mixture washed with water (3×20 mL), dried (MgSO$_4$) and evaporated to give an oil which was purified by chromatography on silica gel eluting with an EtOAc/DCM gradient (0-25%) to provide the title compound as a clear colourless oil. (175 mg, 75%)

$^1$H NMR (300.073 MHz, DMSO-d$_6$) δ0.67 (3H, t), 1.14-1.39 (7H, m), 1.57-1.61 (1H, m), 1.71-1.74 (2H, m), 1.84 (2H, d), 2.68-2.72 (2H, m), 3.71-3.85 (1H, m), 3.89 (3H, s), 7.72 (1H, t), 7.83-7.94 (2H, m), 8.05-8.08 (2H, m), 8.14 (1H, s)

MS m/z 402 M+H

Intermediate#15: methyl 4-[5-chloro-4-(cyclohexylcarbamoyl)pyrazol-1-yl]benzoate

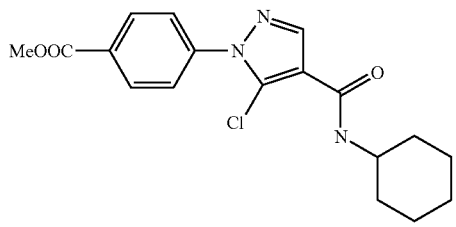

t-Butylnitrite (210 mg, 2.04 mmol) and cupric chloride (342 mg, 2.55 mmol) were added to acetonitrile (15 mL) and heated to 65° C. Methyl 4-[5-amino-4-(cyclohexylcarbamoyl)pyrazol-1-yl]benzoate (Intermediate #16) (581 mg, 1.7 mmol) was added as a solid in portions giving a vigorous gas evolution. After the addition was complete the reaction mixture was heated for a further 15 min. at 65° C., cooled to ambient, diluted with water (100 mL) and extracted with ethyl acetate (3×50 mL). The combined extracts were washed with brine (2×20 mL), dried (MgSO$_4$) and evaporated to give a solid, which was purified by chromatography on silica gel eluting with an EtOAc/Hexane gradient (0-30%) to give the title compound as a white solid (385 mg, 65%)

Intermediate #16: Methyl 4-[5-amino-4-(cyclohexyl-carbamoyl)pyrazol-1-yl]benzoate

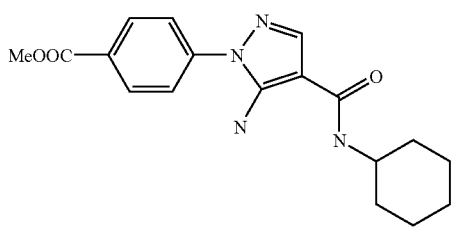

2-cyano-N-cyclohexyl-3-ethoxy-prop-2-enamide (Intermediate #17) (605 mg, 2.73 mmol) and methyl 4-hydrazinyl-benzoate hydrochloride (Intermediate#123) (552 mg, 2.73 mmol) were suspended in ethanol (20 mL). DIPEA (351 mg, 2.73 mmol) was added and the mixture heated to 70° C. for 1 h. The reaction mixture was cooled to ambient and the resulting precipitate recovered by filtration, washed with ether and dried in vacuo to give the title compound as a white solid. (618 mg 66%)

$^1$H NMR (300.073 MHz, DMSO-$d_6$) δ1.13 (1H, d), 1.22-1.35 (4H, m), 1.60 (1H, d), 1.76 (4H, d), 3.69-3.74 (1H, m), 3.87 (3H, s), 6.56 (2H, s), 7.62 (1H, d), 7.73-7.78 (2H, m), 8.04 (1H, s), 8.05-8.09 (2H, m)

MS m/z 343 M+H

Intermediate #17: 2-cyano-N-cyclohexyl-3-ethoxy-prop-2-enamide

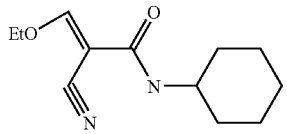

2-cyano-N-cyclohexyl-acetamide (Intermediate #18) (1.35 g, 8.09 mmol) was suspended in acetic anhydride (20 mL). Triethyl orthoformate (3.91 g, 21 mmol) was added and the mixture heated to reflux for 5 h. The reaction mixture was cooled to ambient and volatiles removed by evaporation in vacuo to leave a brown oil which was which was purified by chromatography on silica gel eluting with an EtOAc/DCM gradient (0-10%) to give the title compound as a solid (637 mg, 35%)

$^1$H NMR (300.073 MHz, DMSO-$d_6$) δ1.01-1.35 (8H, m), 1.51-1.82 (5H, m), 3.54-3.61 (1H, m), 4.32 (2H, q), 7.57 (1H, d), 8.11 (1H, t)

MS m/z 223 M+H

Intermediate #18: 2-cyano-N-cyclohexyl-acetamide

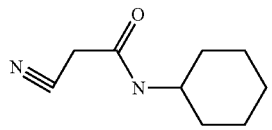

Cyanoacetic acid (4.26 g, 50 mmol) and cyclohexylamine (4.96 g, 50 mmol) were dissolved in DCM (100 mL). EDCI (10.51 g, 55 mmol) was added and the mixture stiffed at ambient temperature for 24 h. The reaction mixture was washed with water (2×100 mL), dried (MgSO4) and evaporated to leave a yellow solid residue which was purified by chromatography on silica gel eluting with an EtOAc/DCM gradient (0-100%) to provide the title compound as a white solid (5.66 g, 68%).

$^1$H NMR (300.073 MHz, DMSO-$d_6$) δ1.06-1.32 (5H, m), 1.51-1.55 (1H, m), 1.63-1.75 (4H, m), 3.46-3.57 (1H, m), 3.55 (2H, s), 8.06-8.09 (1H, m)

Intermediate #19: Methyl 3-[5-chloro-4-(cyclohexyl-carbamoyl)pyrazol-1-yl]benzoate

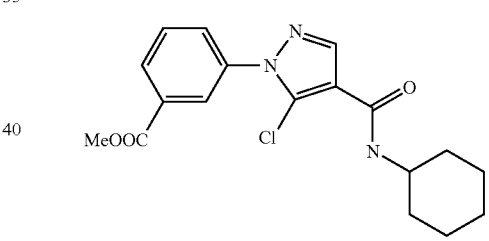

t-Butylnitrite (145 mg, 1.38 mmol) and cupric chloride (236 mg, 1.76 mmol) were added to acetonitrile (10 mL) and heated to 65° C. Methyl 3-[5-amino-4-(cyclohexylcarbamoyl)pyrazol-1-yl]benzoate (Intermediate #20) (400 mg, 1.38 mmol) was added as a solid in portions giving a vigorous gas evolution. After the addition was complete heating was continued for a further 15 min and then cooled to ambient, diluted with water (50 mL) and extracted with ethyl acetate (3×25 mL). The combined extracts were washed with water (2×20 mL), dried (MgSO$_4$) and evaporated to give a brown oil which was purified by chromatography on silica gel eluting with an EtOAc/Hexane gradient (0-50%) to provide the title compound as a clear colourless oil. (256 mg, 51%)

$^1$H NMR (400.13 MHz, CDCl$_3$) δ1.15-1.25 (3H, m), 1.32-1.43 (2H, m), 1.58 (1H, d), 1.65-1.71 (2H, m), 1.94-1.98 (2H, m), 3.89 (3H, s), 3.91-3.98 (1H, m), 6.04 (1H, d), 7.55 (1H, t), 7.66-7.68 (1H, m), 8.08-8.10 (2H, m), 8.15 (1H, t)

MS m/z 360 M−H

Intermediate #20: Methyl 3-[5-amino-4-(cyclohexylcarbamoyl)pyrazol-1-yl]benzoate

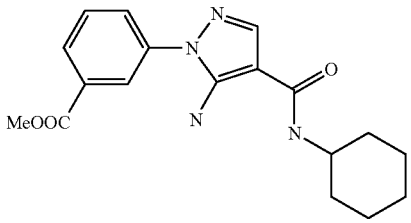

2-cyano-N-cyclohexyl-3-ethoxy-prop-2-enamide (Intermediate #17) (605 mg, 2.73 mmol) and methyl 3-hydrazinylbenzoate hydrochloride (552 mg, 2.73 mmol) were suspended in ethanol (20 mL). DIPEA (352 mg, 2.73 mmol) was added and the mixture heated to 70° C. for 1 h. The reaction mixture was cooled to ambient and concentrated to a small volume. Water (50 mL) was added and the resulting solid recovered by filtration, redissolved in ethyl acetate (50 mL), dried (MgSO$_4$) and evaporated to give a brown solid which was slurried with ether and recovered by filtration to give the title compound as light brown solid (443 mg, 47%).

$^1$H NMR (300.073 MHz, DMSO-d$_6$) δ1.20 (5H, d), 1.61 (1H, d), 1.72-1.75 (2H, m), 1.80 (2H, d), 3.70-3.74 (1H, m), 3.88 (3H, s), 6.47 (2H, s), 7.59-7.69 (2H, m), 7.84-7.88 (1H, m), 7.91-7.94 (1H, m), 8.01 (1H, s), 8.12 (1H, t)

MS m/z 343 M+H

Intermediate #21 Ethyl 4-[4-(cyclohexylcarbamoyl)-5-propyl-pyrazol-1-yl]benzoate

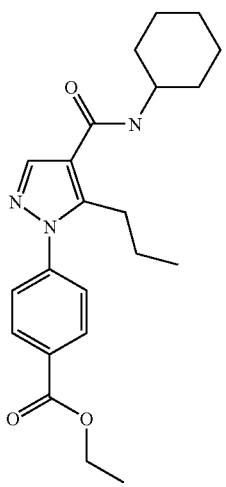

1-(4-chlorophenyl)-N-cyclohexyl-5-propyl-pyrazole-4-carboxamide (Intermediate#22) (159 mg, 0.46 mmol), Molybdenum hexacarbonyl (61 mg, 0.23 mmol), Herrmann's catalyst (Trans-Di-Mu-Acetatobis[2-(Di-O-Tolylphosphino)Benzyl]dipalladium(II), 22 mg, 0.02 mmol), DMAP (113 mg, 0.92 mmol), DIPEA (161 μL, 0.92 mmol), Fu's salt (Tri-(T-Butyl)Phosphonium Hydrogen tetrafluoroborate Salt, 27 mg, 0.09 mmol), Dioxane (2 mL), Ethanol (2 L) were mixed into a microwave tube. The reaction mixture was then heated at 150° C. for 1 hour by microwave. LC-MS showed complete conversion to the product. The solvent was evaporated under reduced pressure and the reaction mixture extracted with EtOAc (2×25 mL), washed with water (10 mL), 2N HCl (10 mL) and brine (10 mL). The organic phase was dried over MgSO$_4$ and evaporated under reduced pressure to give a black gum. The residue was purified by column chromatography (12 g silicycle column, gradient: 1:0 to 1:1 hexane/EtOAc) and appropriate fractions combined and concentrated in vacuo to yield the desired compound as a white solid (130 mg, 74%).

$^1$H NMR (400.13 MHz, CDCl$_3$) δ0.76-0.81 (3H, t), 1.09-1.21 (3H, m), 1.36 (5H, m), 1.45-1.55 (2H, m), 1.61 (1H, m), 1.67-1.72 (2H, m), 1.96-1.98 (2H, m), 2.89-2.93 (2H, m), 3.85-3.92 (1H, m), 4.35 (2H, q), 5.62 (1H, d), 7.41-7.44 (2H, m), 7.71 (1H, s), 8.10-8.13 (2H, m)

MS m/z 384 M+H

Intermediate #22: 1-(4-chlorophenyl)-N-cyclohexyl-5-propyl-pyrazole-4-carboxamide

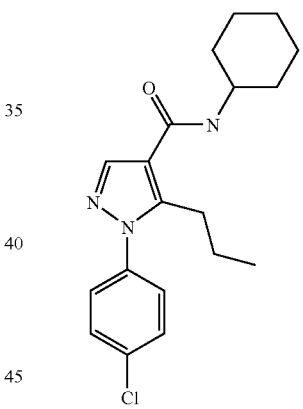

To a suspension of 1-(4-chlorophenyl)-5-propyl-pyrazole-4-carbonyl chloride (commercially available, 302 mg, 1.07 mmol) in DCM (5 ml) was added 1 drop of DMF followed by cyclohexylamine (306 μL, 2.68 mmol). The reaction mixture was stirred at room temperature for two hours then stopped.

It was extracted in DCM (10 mL), washed with 2N NaOH (5 mL), 2N HCl (5 mL), water (mL) and brine (5 mL). The organic phase was dried over MgSO$_4$ and evaporated under reduced pressure to give a white solid (200 mg, 54%), which was used without further purification.

$^1$H NMR (400.13 MHz, DMSO-d$_6$) δ0.73 (3H, t), 1.13 (1H, d), 1.22-1.31 (4H, m), 1.35-1.44 (2H, m), 1.60-1.63 (1H, m), 1.69-1.75 (2H, m), 1.80-1.82 (2H, m), 2.91 (2H, t), 3.72-3.75 (1H, m), 7.48-7.52 (2H, m), 7.61-7.64 (2H, m), 7.84 (1H, d), 8.13 (1H, s)

MS m/z 346 M+H

Intermediate #23: Ethyl 4-[4-(cyclohexyl-methyl-carbamoyl)-5-propyl-pyrazol-1-yl]benzoate

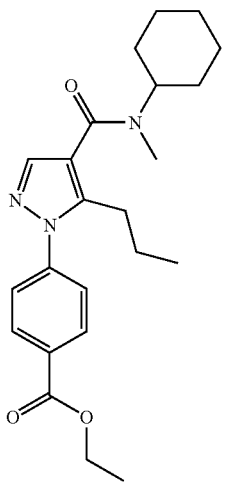

1-(4-chlorophenyl)-N-cyclohexyl-N-methyl-5-propyl-pyrazole-4-carboxamide (Intermediate #24), 101 mg, 0.28 mmol), Molybdenum hexacarbonyl (37 mg, 0.14 mmol), Herrmann's catalyst (Trans-Di-Mu-Acetatobis[2-(Di-O-Tolylphosphino)Benzyl]dipalladium(II), 14 mg, 0.01 mmol), DMAP (69 mg, 0.56 mmol), DIPEA (98 µL, 0.56 mmol), Fu's salt (Tri-(T-Butyl)Phosphonium Hydrogen tetrafluoroborate Salt, 17 mg, 0.06 mmol), Dioxane (2 mL), Ethanol (2 mL) were mixed into a microwave tube. The reaction mixture was then heated at 150° C. for 1 hour by microwave.

LC-MS showed complete conversion to the product. The same reaction was repeated in another microwave tube and the two reaction mixtures were combined for work up and purification. The solvent was evaporated under reduced pressure and the reaction mixture extracted with EtOAc (2×25 mL), washed with water (10 mL), 2N HCl (10 mL) and brine (10 mL). The organic phase was dried over MgSO$_4$ and evaporated under reduced pressure to give a black gum. The residue was purified by column chromatography (12 g silicycle column, gradient: 1:0 to 1:1 hexane/EtOAc) and appropriate fractions combined and concentrated in vacuo to yield the desired compound as a white solid (105 mg, 61%).

$^1$H NMR (400.13 MHz, CDCl$_3$) δ0.71-0.79 (3H, t), 1.02-1.10 (1H, m), 1.19 (2H, t), 1.31-1.40 (5H, m), 1.55-1.72 (4H, m), 1.75-1.78 (2H, m), 2.73-2.79 (2H, m), 2.89 (3H, m), 4.05 (1H, q), 4.35 (2H, q), 6.99-7.11 (1H, m), 7.46 (2H, d), 7.55 (1H, s), 8.10-8.13 (2H, d)
MS m/z 398 M+H

Intermediate #24: 1-(4-chlorophenyl)-N-cyclohexyl-N-methyl-5-propyl-pyrazole-4-carboxamide

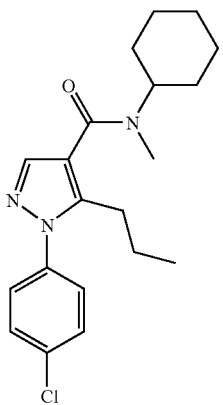

To a suspension of 1-(4-chlorophenyl)-5-propyl-pyrazole-4-carbonyl chloride (commercially available, 302 mg, 1.07 mmol) in DCM (5 ml) was added 1 drop of DMF followed by N-methylcyclohexylamine (349 µL, 2.68 mmol). The reaction mixture was stiffed at room temperature for two hours then stopped.

It was extracted in DCM (10 mL), washed with 2N NaOH (5 mL), 2N HCl (5 mL), water (5 mL) and brine (5 mL). The organic phase was dried over MgSO$_4$ and evaporated under reduced pressure to give a colourless gum (263 mg, 73%), which was used without further purification.

$^1$H NMR (400.13 MHz, DMSO-d$_6$) δ0.70 (3H, t), 1.20-1.46 (5H, m), 1.58-1.63 (5H, m), 1.76-1.79 (2H, m), 2.73-2.74 (3H, m), 2.89 (4H, m), 7.54-7.57 (2H, m), 7.61-7.64 (2H, m)
MS m/z 360 M+H

Intermediate #25: 1-(4-bromophenyl)-N-cyclohexyl-5-cyclopropyl-pyrazole-4-carboxamide

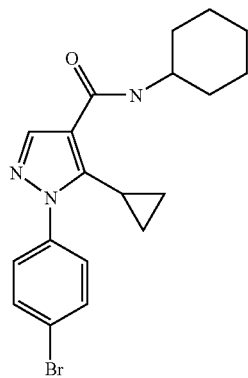

1-(4-bromophenyl)-5-cyclopropyl-pyrazole-4-carboxylic acid (Intermediate#30) (237 mg, 0.77 mmol) was suspended in DCM (5 mL). One drop of DMF was added and then oxalyl chloride (200 µL, 2.32 mmol) was added slowly. The reaction mixture was stiffed at ambient temperature for 4 h and then evaporated under reduced pressure. The residue was dissolved in DCM (5 mL) and added to a solution of cyclohexylamine (97 µL, 0.85 mmol) and DIPEA (403 µL, 2.32 mmol) in DCM (5 mL). The mixture was stirred at ambient for 24 h and then water, (10 mL) was added and the mixture passed through a phase separating filter. The product was recovered from the filtrate by flash column chromatography (SiO2, elution gradient 0-100% EtOAc in isohexane). Pure fractions were combined and evaporated to give 1-(4-bromophenyl)-N-cyclohexyl-5-cyclopropyl-pyrazole-4-carboxamide as white solid. (277 mg, 92%)

$^1$H NMR (400.13 MHz, DMSO-d$_6$) δ0.39-0.43 (2H, m), 0.84-0.89 (2H, m), 1.12-1.20 (1H, m), 1.24-1.36 (4H, m), 1.61 (1H, d), 1.69-1.75 (2H, m), 1.87 (2H, d), 2.14-2.21 (1H, m), 3.72-3.77 (1H, m), 7.73-7.79 (3H, m), 7.92-7.98 (1H, m), 8.07-8.10 (2H, m), 13.17 (1H, s)
MS m/z (ESI+) (M+H)+390

The following intermediates were prepared from 1-(4-bromophenyl)-5-cyclopropyl-pyrazole-4-carboxylic acid (Intermediate#30) in a similar manner to Intermediate #25, using the appropriate amine starting material:

| Structure | Int. # | Name | ¹H NMR δ | MS m/e MH⁺ |
|---|---|---|---|---|
| 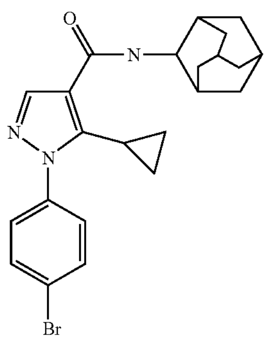 | 26 | N-(2-adamantyl)-1-(4-bromophenyl)-5-cyclopropyl-pyrazole-4-carboxamide | ¹H NMR (300.073 MHz, DMSO-$d_6$) δ 0.41-0.46 (2 H, m), 0.79-0.88 (2 H, m), 1.54 (2 H, d), 1.72 (2 H, s), 1.83 (6 H, d), 1.94 (2 H, s), 2.05 (2 H, d), 2.13-2.22 (1 H, m), 4.04 (1 H, d), 7.52 (1 H, d), 7.56 (2 H, d), 7.73 (2 H, d), 7.89 (1 H, s) | 440 |
| 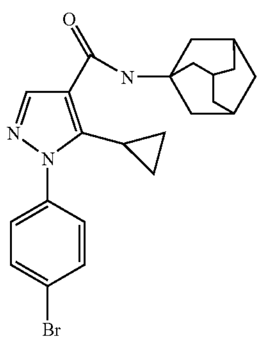 | 27 | N-(1-adamantyl)-1-(4-bromophenyl)-5-cyclopropyl-pyrazole-4-carboxamide | ¹H NMR (300.073 MHz, DMSO-$d_6$) δ 0.41-0.46 (2 H, m), 0.83-0.89 (2 H, m), 1.65 (6 H, s), 2.05 (9 H, s), 2.08-2.14 (1 H, m), 7.13 (1 H, s), 7.51-7.56 (2 H, m), 7.69-7.74 (2 H, m), 7.81 (1 H, s) | 440 |
| 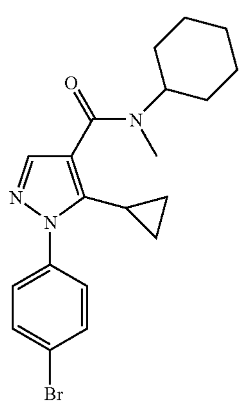 | 28 | 1-(4-bromophenyl)-N-cyclohexyl-5-cyclopropyl-N-methyl-pyrazole-4-carboxamide | ¹H NMR (300.073 MHz, DMSO-$d_6$) δ 0.35-0.55 (2 H, m), 0.79-0.81 (2 H, m), 1.11-1.23 (2 H, m), 1.33 (1 H, s), 1.55 (2 H, s), 1.61-1.65 (3 H, m), 1.76 (2 H, s), 1.98 (1 H, s), 2.85 (3 H, s), 3.43-3.70 (0.4 H, s), 4.31 (0.6 H, s), 7.63 (3 H, d), 7.72 (2 H, d) | 402 |
| 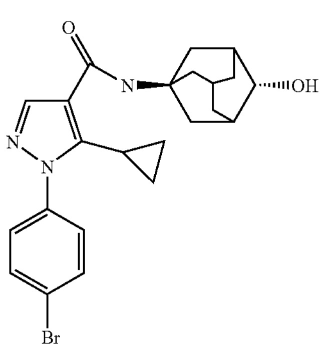 | 29 | 1-(4-bromophenyl)-5-cyclopropyl-N-(4-hydroxy-1-adamantyl)pyrazole-4-carboxamide | 1H NMR (400.13 MHz, DMSO-$d_6$) δ 0.43-0.47 (2 H, m), 0.83-0.88 (2 H, m), 1.38 (2 H, d), 1.65 (4 H, d), 1.75 (2 H, d), 1.95 (2 H, d), 2.03-2.08 (3 H, m), 3.97 (1 H, t), 4.39 (1 H, s), 7.47-7.49 (1 H, m), 7.56-7.59 (2 H, m), 7.72-7.76 (2 H, m), 7.91 (1 H, s) | 458 |

Intermediate#30 1-(4-bromophenyl)-5-cyclopropyl-pyrazole-4-carboxylic acid

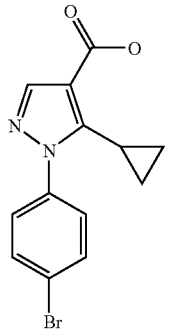

Ethyl 1-(4-bromophenyl)-5-cyclopropyl-pyrazole-4-carboxylate (Intermediate# 31) (423 mg, 1.29 mmol) was dissolved in methanol (20 mL) and treated with 2M aqueous sodium hydroxide solution (3.23 mL, 6.46 mmol). The mixture was stirred at ambient temperature for 24 h and then the methanol was removed by evaporation under reduced pressure. The residue was dissolved in water (50 mL), acidified to pH4 with 2M HCl and extracted with EtOAc (3×25 mL). The combined extracts were washed with water and brine, dried (MgSO4) and evaporated to leave 1-(4-bromophenyl)-5-cyclopropyl-pyrazole-4-carboxylic acid a white solid. (343 mg, 87%).

$^{1}$H NMR (300.073 MHz, DMSO-$d_6$) δ0.46-0.57 (2H, m), 0.82-0.87 (2H, m), 1.98-2.11 (1H, m), 7.55-7.62 (2H, m), 7.71-7.75 (2H, m), 7.94 (1H, s), 12.32 (1H, s)

MS m/z (ESI+) (M+H)+309

Intermediate#31 Ethyl 1-(4-bromophenyl)-5-cyclopropyl-pyrazole-4-carboxylate

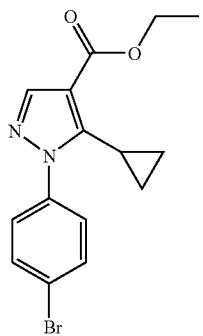

Ethyl-2-(cyclopropanecarbonyl)-3-dimethylamino-prop-2-enoate (Intermediate#32) (316 mg, 1.5 mmol) was dissolved in ethanol (5 mL). 4-bromophenylhydrazine hydrochloride (335 mg, 1.5 mmol) and DIPEA (264 µL, 1.5 mmol) were added and the mixture was heated to reflux for 2 h. The reaction mixture was cooled to ambient and evaporated under reduced pressure. The residue was dissolved in DCM (10 mL) washed with water and poured through a phase separating tube. The product was recovered from the filtrate by flash column chromatography (SiO2, elution gradient 0-25% EtOAc in isohexane). Pure fractions were combined and evaporated to give ethyl 1-(4-bromophenyl)-5-cyclopropyl-pyrazole-4-carboxylate as an oil that crystallised on standing. (343 mg, 87%)

$^{1}$H NMR (300.073 MHz, DMSO-$d_6$) δ0.43-0.49 (2H, m), 0.84-0.90 (2H, m), 1.29 (3H, t), 2.05-2.14 (1H, m), 4.24 (2H, q), 7.55-7.60 (2H, m), 7.71-7.76 (2H, m), 7.98 (1H, d) MS m/z (ESI+) (M+) 335

Intermediate#32 Ethyl-2-(cyclopropanecarbonyl)-3-dimethylamino-prop-2-enoate

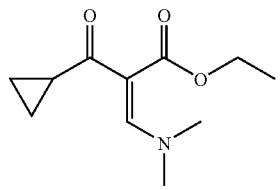

Ethyl 3-cyclopropane-3-oxopropionionate (312 mg, 2 mmol) and N,N-dimethylformamide dimethylacetal (402 µL, 3 mmol) were dissolved in dioxan (5 mL) and heated to reflux for 2 h. The reaction mixture was cooled to ambient and evaporated under to reduced pressure to leave a yellow oil, which was purified by flash column chromatography (SiO2, elution gradient 0-100% EtOAc in isohexane). Pure fractions were combined and evaporated to give ethyl-2-(cyclopropanecarbonyl)-3-dimethylamino-prop-2-enoate as an oil. (316 mg, 74%)

$^{1}$H NMR (300.073 MHz, DMSO-$d_6$) δ0.69-0.80 (4H, m), 1.15-1.24 (3H, m), 2.26-2.34 (1H, m), 2.94 (6H, s), 4.11 (2H, q), 7.57 (1H, s)

MS m/z (ESI+) (M+H)+212

Intermediate #33: Methyl 2-[4-[4-(cyclohexylcarbamoyl)-5-propylsulfanyl-pyrazol-1-yl]phenyl]acetate

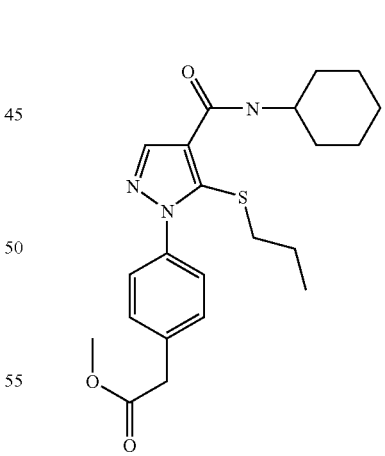

1-[4-(methoxycarbonylmethyl)phenyl]-5-propylsulfanyl-pyrazole-4-carboxylic acid (Intermediate#35) (220 mg, 0.66 mmol) was dissolved in DCM (5 mL) and 1 drop of DMF added. Oxalyl chloride (176 µL, 1.96 mmol) was added and the mixture stiffed at ambient temperature for 3 h. Volatiles were removed by evaporation under reduced pressure and the resulting gum re-dissolved in DCM (2 mL) and added at ambient temperature to a solution of cyclohexylamine (66 mg, 0.66 mmol) and DIPEA (230 μL, 1.32 mmol) in DCM (5 mL). The reaction mixture was stirred at ambient temperature for 2 h, diluted with EtOAc (50 mL) and washed with water (2×10 mL) and brine (10 mL), dried (MgSO4) and evaporated under reduced pressure. The residue was purified by flash chromatography on silica gel (elution gradient 0-100% EtOAc in isohexane) to afford methyl 2-[4-[4-(cyclohexyl-carbamoyl)-5-propylsulfanyl-pyrazol-1-yl]phenyl]acetate as a white solid. (220 mg, 88%)

1H NMR (300.073 MHz, DMSO-d$_6$) δ 0.69 (3H, t), 1.20-1.32 (7H, m), 1.58 (1H, d), 1.69-1.74 (2H, m), 1.83 (2H, d), 2.68 (2H, t), 3.64 (3H, s), 3.74-3.82 (1H, m), 3.80 (2H, s), 7.44 (4H, s), 7.84-7.89 (1H, m), 8.08 (1H, s)

MS m/z (ESI+) (M+H)+416

Intermediate #34: Methyl 2-[4-[4-(2-adamantylcarbamoyl)-5-propylsulfanyl-pyrazol-1-yl]phenyl]acetate

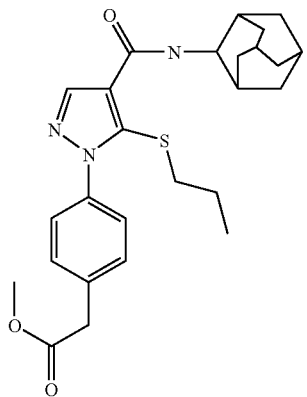

Prepared from 1-[4-(methoxycarbonylmethyl)phenyl]-5-propylsulfanyl-pyrazole-4-carboxylic acid (Intermediate#35) and 2-adamantylamine hydrochloride by the same procedure as used for Intermediate #6.

1H NMR (300.073 MHz, DMSO-d$_6$) δ 0.67 (3H, t), 1.15-1.31 (2H, m), 1.61 (2H, d), 1.73 (2H, s), 1.83 (6H, s), 1.96 (4H, d), 2.61 (2H, t), 3.64 (3H, s), 3.80 (2H, s), 4.09 (1H, d), 7.40-7.52 (4H, m), 8.02 (1H, d), 8.11 (1H, s)

MS m/z (ESI+) (M+H)+468

Intermediate #35: 1-[4-(methoxycarbonylmethyl)phenyl]-5-propylsulfanyl-pyrazole-4-carboxylic acid

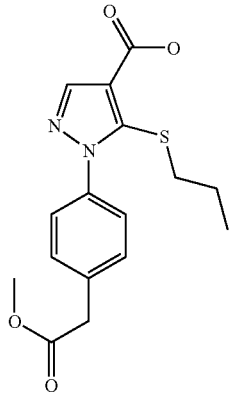

tert-butyl 1-[4-(methoxycarbonylmethyl)phenyl]-5-propylsulfanyl-pyrazole-4-carboxylate (Intermediate#36) was dissolved in DCM (10 mL). TFA (2 mL) was added and the mixture was stirred at ambient temperature for 5 h. Volatiles were then evaporated under reduced pressure and the residue dried under vacuum to afford 1-[4-(methoxycarbonylmethyl)phenyl]-5-propylsulfanyl-pyrazole-4-carboxylic acid as a light brown oil. (440 mg, 98%)

1H NMR (300.073 MHz, DMSO-d$_6$) δ 0.70 (3H, t), 1.21-1.33 (2H, m), 2.79 (2H, t), 3.64 (3H, s), 3.80 (2H, s), 7.44 (4H, s), 8.10 (1H, s)

Intermediate #36: tert-butyl 1-[4-(methoxycarbonylmethyl)phenyl]-5-propylsulfanyl-pyrazole-4-carboxylate

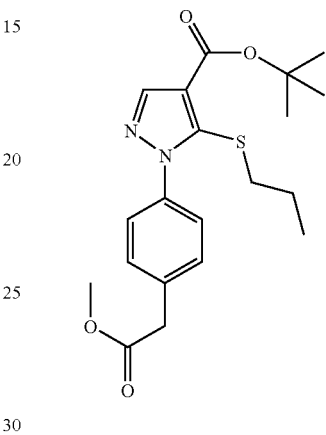

tert-butyl 5-chloro-1-[4-(methoxycarbonylmethyl)phenyl]pyrazole-4-carboxylate (Intermediate#37) (767 mg, 2.19 mmol) was dissolved in butyronitrile (10 mL). Potassium carbonate (906 mg, 6.57 mmol) and propanethiol (284 μL, 2.74 mmol) were added and the mixture heated at 90° C. for 18 h. The reaction mixture was cooled to ambient and ethyl acetate (50 mL) was added. The mixture was washed with water (4×25 mL), dried (MgSO4) and evaporated under reduced pressure. The residue was purified by flash chromatography on silica gel (elution gradient 0-25% EtOAc in isohexane) to afford tert-butyl 1-[4-(methoxycarbonylmethyl)phenyl]-5-propylsulfanyl-pyrazole-4-carboxylate as a yellow oil. (527 mg, 62%).

1H NMR (300.073 MHz, DMSO-d$_6$) δ 0.70 (3H, t), 1.27 (2H, q), 1.53-1.54 (9 s, 2.75 (2H, t), 3.64 (3H, s), 3.80 (2H, s), 7.44 (4H, s), 8.07-8.12 (1H, m)

MS m/z (ESI+) (M+H)+391

Intermediate #37: tert-butyl 5-chloro-1-[4-(methoxycarbonylmethyl)phenyl]pyrazole-4-carboxylate

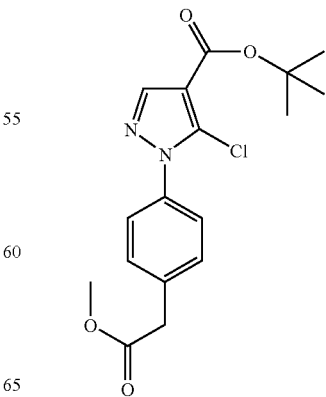

t-Butylnitrite (419 µL, 3.49 mmol) and copper (2) chloride (585 mg, 4.37 mmol) were added to acetonitrile (10 mL) and heated to 65° C. Tert-butyl 5-amino-1-[4-(methoxycarbonyl-methyl)phenyl]pyrazole-4-carboxylate (Intermediate#38) (965 mg, 2.91 mmol) was added as a solution in acetonitrile (5 mL) giving a vigorous gas evolution. After the addition was complete heating was continued for a further 15 min. The reaction mixture was cooled to ambient, diluted with water (50 mL) and extracted with ethyl acetate (3×50 mL). The combined extracts were washed with water (2×50 mL) and brine (10 mL), dried (MgSO4) and evaporated to give a brown oil which was purified by flash chromatography on silica gel (elution gradient 0-50% EtOAc in isohexane) to give the title compound as a yellow oil. (785 mg, 77%)

1H NMR (300.073 MHz, DMSO-d$_6$) δ 1.52 (9H, s), 3.62-3.64 (3H, m), 3.81 (2H, s), 7.48-7.54 (4H, m), 8.12 (1H, s)

MS m/z (ESI+) (M+H)+351

Intermediate#38: tert-butyl 5-amino-1-[4-(methoxy-carbonylmethyl)phenyl)pyrazole-4-carboxylate

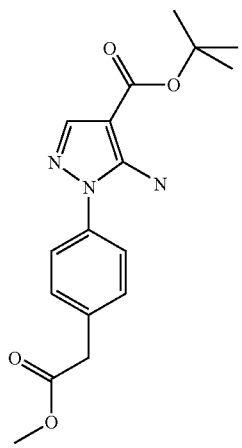

t-Butyl cyanoacetate (3.525 g, 25 mmol) was dissolved in triethyl orthoformate (6.2 mL, 37.5 mmol). Acetic anhydride (2.41 mL, 25 mmol) was added and the mixture heated to 125° C. for 3 h. Volatiles were then removed by evaporation under reduced pressure to leave an orange oil. The crude oil was dissolved in methanol and methyl 2-(4-hydrazinylphe-nyl)acetate hydrochloride (Intermediate#39) (1.62 g, 7.5 mmol) and DIPEA (1.3 mL, 7.5 mmol) were added. The mixture was heated to reflux for 2 h and then evaporated to dryness. The residue was dissolved in ethyl acetate (100 mL), washed with water (2×50 mL) and brine (50 mL), dried (MgSO4) and evaporated to leave a crude product which was purified by flash chromatography on silica gel (elution gradient 0-50% EtOAc in isohexane) to give the title compound as a yellow solid. (974 mg, 39%)

1H NMR (300.073 MHz, DMSO-d$_6$) δ 1.51 (9H, d), 3.63 (3H, s), 3.76 (2H, s), 6.20 (2H, s), 7.41 (2H, d), 7.48 (2H, d), 7.60 (1H, s)

MS m/z (ESI+) (M+H)+331

Intermediate#39: methyl 2-(4-hydrazinylphenyl)acetate hydrochloride

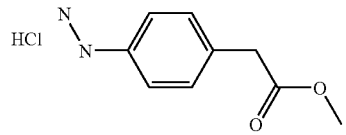

A solution of methyl 4-iodophenylacetate (4.25 g, 15.39 mmol) was dissolved in DMF (25 mL). BOC-carbazate (2.44 g, 18.47 mmol), 1,10-phenanthroline (278 mg, 1.54 mmol), copper iodide (147 mg, 0.77 mmol) and cesium carbonate (7.0 g, 21.55 mmol) were added and the mixture heated at 120° C. for 60 min. The reaction mixture was diluted with ethyl acetate (25 mL), washed with water (3×10 mL) and brine (10 mL), dried (MgSO4) and evaporated to leave a brown oil which was purified by flash chromatography on silica gel (elution gradient 0-50% EtOAc in isohexane) to give a colourless oil. The oil was dissolved in 4M HCl Dioxan (20 mL) and stirred at ambient temperature for 3 h giving a thick precipitate. Diethyl ether (100 mL) was added and the precipitate recovered by filtration, washed with ether (2×20 mL) and dried under vacuum to leave methyl 2-(4-hydrazi-nylphenyl)acetate hydrochloride as a light brown solid. (1.63 g, 49%)

1H NMR (300.073 MHz, DMSO-d$_6$) δ 3.59 (5H, s), 6.93 (2H, d), 7.16 (2H, d), 8.21 (1H, s), 10.20 (3H, s)

Intermediate#40: 3-(4-Cyclohexylcarbamoyl-5-pro-pylsulfanyl-pyrazol-1-ylmethyl)-benzoic acid methyl ester

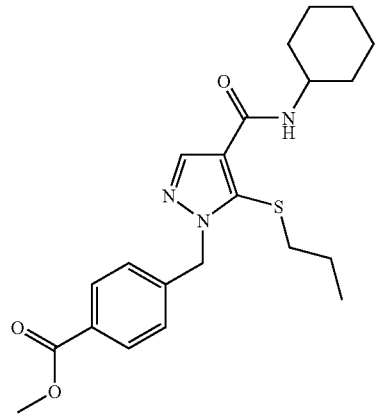

is A solution of 1-(4-Methoxycarbonyl-benzyl)-5-propyl-sulfanyl-1H-pyrazole-4-carboxylic acid (Intermediate#44) (118 mg, 0.35 mmol), cyclohexylamine (49 µl, 0.42 mmol), EDAC (75 mg, 0.39 mmol) and DMAP (9 mg, 0.07 mmol) in DCM (5 ml) was stirred overnight at ambient temperature. The solvent was evaporated in vacuo and the resulting residue was partitioned between EtOAc (~30 ml) and citric acid (~20 ml). The layers were separated and the aqueous layer was re-extracted with EtOAc (~10 ml). The combined organic layers were washed with brine (~10 ml) then dried (MgSO$_4$), filtered and evaporated to yield an oil. The oil was purified by column chromatography (4 g Si, eluting with 20 to 60% EtOAc in 1H) to yield the title compound as a pale yellow oil (116 mg, 79%).

¹H NMR (300.072 MHz, CDCl₃) δ0.81 (3H, t), 1.13-1.25 (3H, m), 1.30-1.48 (4H, m), 1.52-1.69 (3H, m), 1.89-1.94 (2H, m), 2.47 (2H, t), 3.83 (3H, s), 3.88-3.98 (1H, m), 5.49 (2H, s), 7.18 (2H, d), 7.24 (1H, d), 7.92 (2H, d), 8.07 (1H, s) MS m/e MH⁺ 416.

The following intermediates were made by the above procedure using the corresponding starting materials

| Structure | Intermediate # | Name | NMR | [M + H]+ |
|---|---|---|---|---|
| 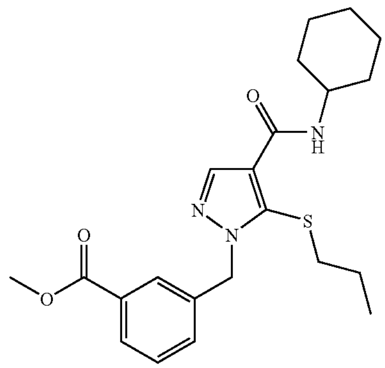 | 41 | 3-(4-Cyclohexylcarbamoyl-5-propylsulfanyl-pyrazol-1-ylmethyl)-benzoic acid methyl ester | ¹H NMR (300.072 MHz, CDCl₃) δ 0.82 (3 H, t), 1.13-1.26 (3 H, m), 1.30-1.50 (4 H, m), 1.50-1.70 (3 H, m), 1.85-1.95 (2 H, m), 2.48 (2 H, t), 3.84 (3 H, s), 3.88-3.96 (1 H, m), 5.48 (2 H, s), 7.31-7.34 (3 H, m), 7.86-7.91 (2 H, m), 8.06 (1 H, s) | 416 |
| 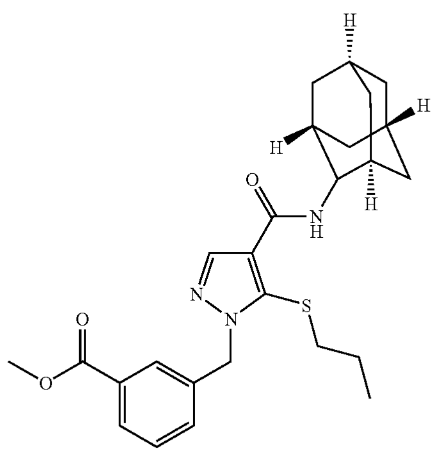 | 42 | 3-[4-(Adamantan-2-ylcarbamoyl)-5-propylsulfanyl-pyrazol-1-ylmethyl]-benzoic acid methyl ester | 1H NMR (300.072 MHz, CDCl₃) δ 0.81 (3 H, t), 1.37-1.50 (2 H, m), 1.58-1.75 (4 H, m), 1.82 (8 H, s), 1.95 (2 H, s), 2.50 (2 H, t), 3.84 (3 H, s), 4.20-4.23 (1 H, m), 5.49 (2 H, s), 7.33-7.35 (2 H, m), 7.83-7.92 (3 H, m), 8.09 (1 H, s) | 468 |
| 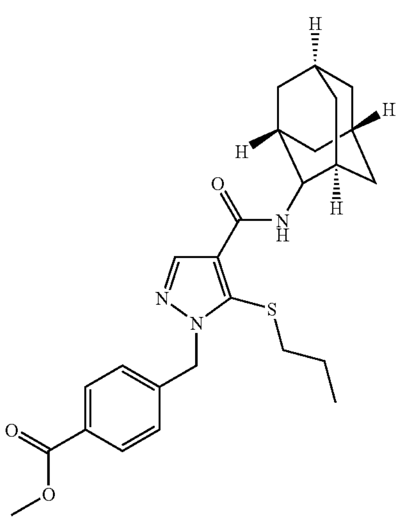 | 43 | 4-[4-(Adamantan-2-ylcarbamoyl)-5-propylsulfanyl-pyrazol-1-ylmethyl]-benzoic acid methyl ester | 1H NMR (300.072 MHz, CDCl₃) δ 0.80 (3 H, t), 1.36-1.49 (2 H, m), 1.58-1.77 (4 H, m), 1.82 (8 H, s), 1.95 (2 H, s), 2.49 (2 H, t), 3.83 (3 H, s), 4.20-4.23 (1 H, m), 5.50 (2 H, s), 7.19 (2 H, d), 7.84 (1 H, d), 7.92 (2 H, d), 8.10 (1 H, s) | 468 |

Intermediate#44: 1-(4-Methoxycarbonyl-benzyl)-5-propylsulfanyl-1H-pyrazole-4-carboxylic acid

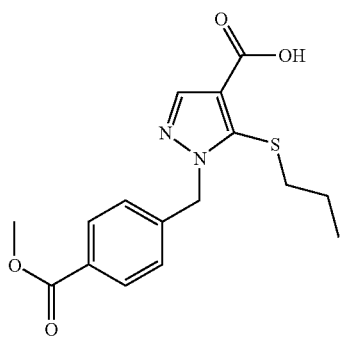

TFA (1.5 ml) was added to a stirred solution of 1-(4-Methoxycarbonyl-benzyl)-5-propylsulfanyl-1H-pyrazole-4-carboxylic acid tert-butyl ester (Intermediate#46) (274 mg, 0.70 mmol) in DCM (6 ml). The reaction was stirred at ambient temperature for 3 hours then evaporated in vacuo. The resulting gum was sonicated with isohexane to yield a solid. The solvent was removed then the white solid was dissolved in EtOAc and evaporated in vacuo to yield the title compound as an off white solid (236 mg, 100%).

$^1$H NMR (300.072 MHz, CDCl$_3$) δ 0.84 (3H, t), 1.35-1.50 (2H, m), 2.81 (2H, t), 3.83 (3H, s), 5.53 (2H, s), 7.18-7.21 (2H, d), 7.91-7.94 (2H, d), 8.05 (1H, s)

MS m/e MH$^+$ 335.

Intermediate#45: 1-(3-Methoxycarbonyl-benzyl)-5-propylsulfanyl-1H-pyrazole-4-carboxylic acid

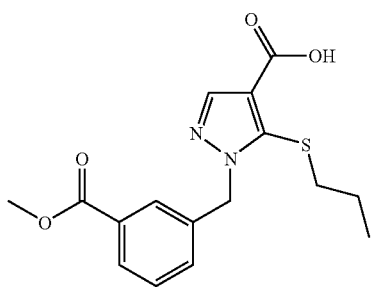

Compound prepared in an analogous manner to Intermediate 44, replacing 1-(4-Methoxycarbonyl-benzyl)-5-propylsulfanyl-1H-pyrazole-4-carboxylic acid tert-butyl ester with 1-(3-Methoxycarbonyl-benzyl)-5-propylsulfanyl-1H-pyrazole-4-carboxylic acid tert-butyl ester (Intermediate#47)

$^1$H NMR (300.072 MHz, CDCl$_3$) δ 0.85 (3H, t), 1.37-1.49 (2H, m), 2.82 (2H, t), 3.83 (3H, s), 5.52 (2H, s), 7.33-7.34 (2H, m), 7.88-7.91 (2H, m), 8.05 (1H, s)

MS m/e [M−H]$^-$ 333.

Intermediate#46: 1-(4-Methoxycarbonyl-benzyl)-5-propylsulfanyl-1H-pyrazole-4-carboxylic acid tert-butyl ester

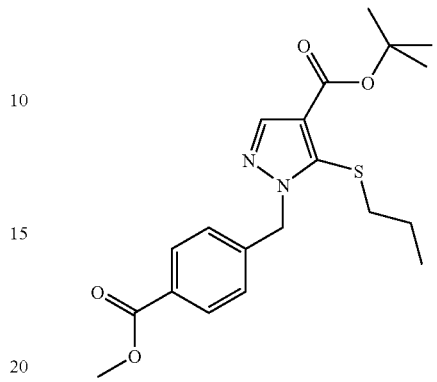

5-Chloro-1-(4-methoxycarbonyl-benzyl)-1H-pyrazole-4-carboxylic acid tert-butyl ester (Intermediate#48) (397 mg, 1.13 mmol) was dissolved in butyronitrile (8 mL), potassium carbonate (470 mg, 3.40 mmol) and propanethiol (128 ul, 1.41 mmol) were added and the mixture heated to reflux and stirred at this temperature over night. The reaction mixture was transferred to a microwave vial (using ~5 ml extra Butyronitrile to ensure complete transfer), a further 3 eq of propane thiol was added and the reaction was heated at 180° C. for 4 hours. EtOAc (~50 mL) was added and the mixture washed with water (3×~20 mL) and brine (~20 ml) then dried (MgSO$_4$), filtered and evaporated to give a yellow oil. Oil purified by column chromatography (12 g Si, eluting with 10 to 50% EtOAc in IH) to yield the title compound as a yellow oil (274 mg, 62%).

$^1$H NMR (300.072 MHz, CDCl$_3$) δ 0.90 (3H, t), 1.40-1.52 (2H, m), 1.55 (9H, s), 2.84 (2H, t), 3.90 (3H, s), 5.57 (2H, s), 7.25 (2H, d), 7.96-8.00 (3H, m)

MS m/e MH$^+$ 391.

Intermediate#47: 1-(3-Methoxycarbonyl-benzyl)-5-propylsulfanyl-1H-pyrazole-4-carboxylic acid tert-butyl ester

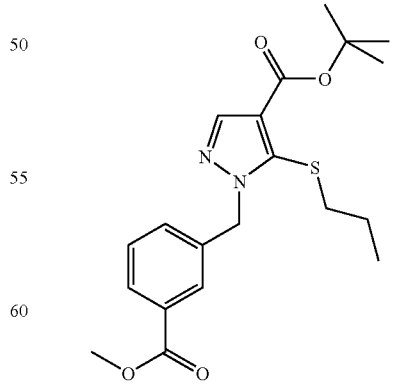

Compound prepared in an analogous manner to Intermediate#46, replacing 5-Chloro-1-(4-methoxycarbonyl-benzyl)-1H-pyrazole-4-carboxylic acid tert-butyl ester with 5-Chloro-1-(3-methoxycarbonyl-benzyl)-1H-pyrazole-4-carboxylic acid tert-butyl ester ¹H NMR (300.072 MHz, CDCl₃) δ0.91 (3H, t), 1.42-1.54 (2H, m), 1.56 (9H, s), 2.84 (2H, t), 3.90 (3H, s), 5.56 (2H, s), 7.37-7.41 (2H, m), 7.93-7.97 (3H, m)

MS m/e MH⁺ 391.

Intermediate#48: 5-Chloro-1-(4-methoxycarbonyl-benzyl)-1H-pyrazole-4-carboxylic acid tert-butyl ester

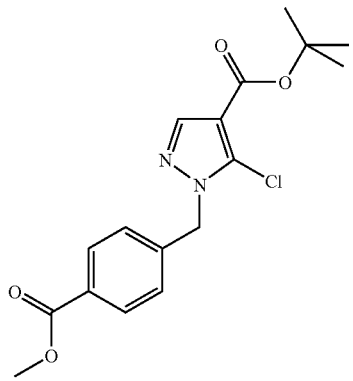

t-Butylnitrite (417 µl, 3.48 mmol) and copper chloride (583 mg, 4.35 mmol) were added to acetonitrile (20 mL) and heated to 65° C. A solution of 5-Amino-1-(4-methoxycarbonyl-benzyl)-1H-pyrazole-4-carboxylic acid tert-butyl ester (Intermediate#50) in acetonitrile (~4 ml) was added dropwise. After the addition was complete heating was continued for a further 15 min. Cooled to ambient, diluted with water (~100 mL) and extracted with ethyl acetate (3×~40 mL). The combined extracts were washed with water (2×~20 mL) and brine (~20 mL), dried (MgSO4), filtered and evaporated to an oil. Chromatographed (40 g silica column, EtOAc/Hexane 10-50%) to yield the title compound as an off white solid (397 mg, 39%).

¹H NMR (300.072 MHz, CDCl₃) δ1.49 (9H, s), 3.83 (3H, s), 5.33 (2H, s), 7.19 (2H, d), 7.84 (1H, s), 7.93 (2H, d)

MS m/e [M+Na]⁺ 373.

Interemdiate#49: 5-Chloro-1-(3-methoxycarbonyl-benzyl)-1H-pyrazole-4-carboxylic acid tert-butyl ester

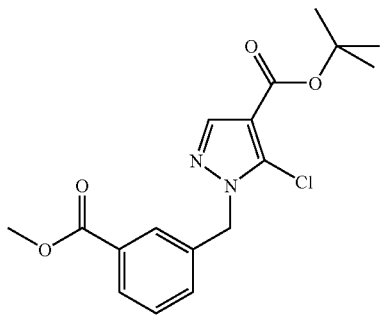

Compound prepared in an analogous manner to Intermediate#48, replacing 5-Amino-1-(4-methoxycarbonyl-benzyl)-1H-pyrazole-4-carboxylic acid tert-butyl ester with 5-Amino-1-(3-methoxycarbonyl-benzyl)-1H-pyrazole-4-carboxylic acid tert-butyl ester (Intermediate#51)

¹H NMR (300.072 MHz, CDCl₃) δ1.49 (9H, s), 3.84 (3H, s), 5.32 (2H, s), 7.33-7.35 (2H, m), 7.84 (1H, s), 7.88-7.93 (2H, m)

MS m/e [M-ᵗBu+H]⁺ 295.

Intermediate#50: 5-Amino-1-(4-methoxycarbonyl-benzyl)-1H-pyrazole-4-carboxylic acid tert-butyl ester

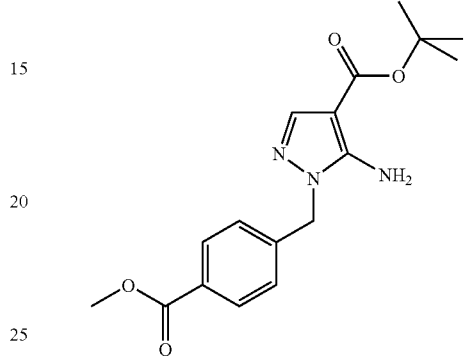

t-Butyl cyanoacetate (600 mg, 4.25 mmol) was dissolved in triethyl orthoformate (1.06 ml, 6.38 mmol), acetic anhydride (0.40 ml, 4.25 mmol) was added and the mixture heated to 125° C. for 2 hours. The solution was evaporated to leave a yellow oil. This oil was redissolved in ethanol (5 ml) and treated with 4-Hydrazinomethyl-benzoic acid methyl ester hydrochloride (Intermediate#52) (230 mg, 1.06 mmol) and DIPEA (184 µl, 1.06 mmol). The resulting mixture was heated to reflux for 2 h and then cooled to ambient temperature and evaporated to leave a brown oil. This oil was dissolved in ethyl acetate (50 mL), washed with water (2×20 mL) and brine (20 mL) then dried (MgSO4), filtered and evaporated. The residue was chromatographed (40 g silica EtOAc/Hexane 0-50%) to yield the title compound as a yellow solid (214 mg, 43%).

¹H NMR (300.072 MHz, CDCl₃) δ1.55 (9H, s), 3.90 (3H, s), 4.86 (2H, s), 5.18 (2H, s), 7.21 (2H, d), 7.62 (1H, s), 8.00 (2H, d)

MS m/e [M−H]⁻ 330.

Intermediate#51: 5-Amino-1-(3-methoxycarbonyl-benzyl)-1H-pyrazole-4-carboxylic acid tert-butyl ester

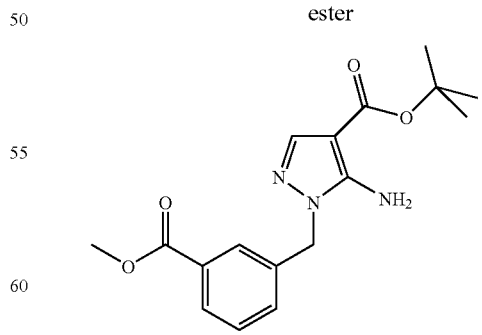

Compound prepared in an analogous manner to Intermediate#50, replacing 4-Hydrazinomethyl-benzoic acid methyl ester hydrochloride with 3-Hydrazinomethyl-benzoic acid methyl ester hydrochloride (Intermediate#53)

¹H NMR (300.072 MHz, CDCl₃) δ1.47 (9H, s), 3.84 (3H, s), 4.75 (2H, s), 5.11 (2H, s), 7.26 (1H, d), 7.36 (1H, t), 7.55 (1H, s), 7.83 (1H, s), 7.90 (1H, d)

MS m/e MH⁺ 332.

Intermediate#52: 4-Hydrazinomethyl-benzoic acid methyl ester hydrochloride

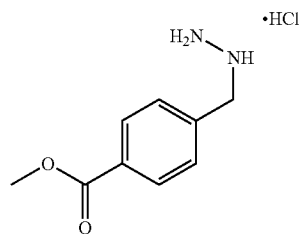

A solution of methyl 4-[[(2-methylpropan-2-yl)oxycarbonyl-[(2-methylpropan-2-yl)oxycarbonylamino]amino]methyl]benzoate (Intermediate#54) (3.3 g, 8.67 mmol) in 4M HCl in Dioxane (100 mL) was stirred overnight at ambient temperature. The solvent was removed under reduced pressure and the resulting solid was dissolved in hot MeOH. The hot suspension was filtered then evaporated in vacuo to give a solid. This solid was triturated with ether, filtered then dried under high vac to yield the title compound as a yellow solid (1.5 g, 80%).

¹H NMR (300.073 MHz, DMSO-d₆) δ3.85 (3H, s), 4.13 (2H, s), 7.55 (2H, d), 7.93 (2H, d)

Intermediate#53: 3-Hydrazinomethyl-benzoic acid methyl ester hydrochloride

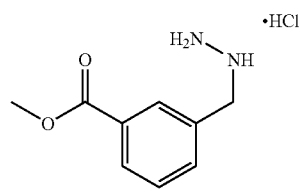

Compound prepared in an analogous manner to intermediate#52, replacing 4-[[(2-methylpropan-2-yl)oxycarbonyl-[(2-methylpropan-2-yl)oxycarbonylamino]amino]methyl]benzoate with 3-[[(2-methylpropan-2-yl)oxycarbonyl-[(2-methylpropan-2-yl)oxycarbonylamino]amino]methyl]benzoate (Intermediate#55)

¹H NMR (300.073 MHz, DMSO-d₆) δ3.86 (3H, s), 4.13 (2H, s), 7.52 (1H, t), 7.70 (1H, d), 7.91 (1H, s), 8.02 (1H, s), 8.77 (4H, br s)

MS m/e MH⁺ 181.

Intermediate#54: methyl 4-[[(2-methylpropan-2-yl)oxycarbonyl-[(2-methylpropan-2-yl)oxycarbonylamino]amino]methyl]benzoate

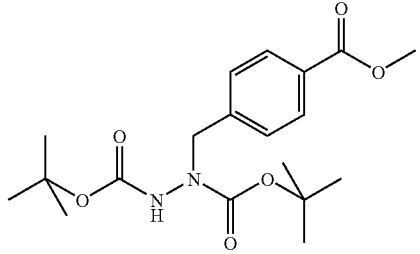

NaH (362 mg, 9.04 mmol) was added to a stirred solution of Di-Tert-Butyl Hydrazodicarboxylate (2 g, 8.61 mmol) in anhydrous THF (50 ml). The reaction was stirred at ambient temperature for 10 minutes then treated with a solution of Methy 4-(Bromomethyl)Benzoate (1.98 g, 8.61 mmol) in anhydrous THF (20 ml). The reaction was stirred at ambient temperature for 4 hours. The reaction was partitioned between ether (~100 ml) and water (~100 ml). The layers were separated and the aqueous layer was re-extracted with ether (~50 ml). The ether layers were combined, washed with brine (~50 ml), dried (MgSO₄), filtered and evaporated to yield the title compound (3.3 g, 100%).

¹H NMR (300.073 MHz, DMSO-d₆) δ1.38 (18H, s), 3.84 (3H, s), 4.52 (2H, br s), 7.42 (2H, d), 7.90 (2H, d), 9.19 (1H, s)

MS m/e [M+Na]⁺ 403.

Intermediate#55: methyl 3-[[(2-methylpropan-2-yl)oxycarbonyl-[(2-methylpropan-2-yl)oxycarbonylamino]amino]methyl]benzoate

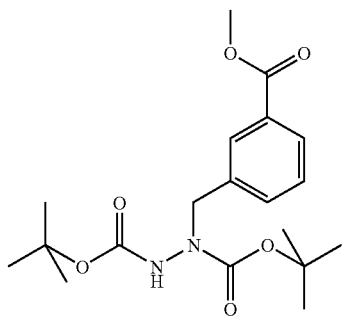

Compound prepared in an analogous manner to Intermediate #54, replacing Methyl 4-(Bromomethyl)Benzoate with Methyl 3-(Bromomethyl)Benzoate ¹H NMR (400.13 MHz, DMSO-d₆) δ1.39 (18H, s), 3.86 (3H, s), 4.50-4.58 (2H, m), 7.45-7.52 (1H, m), 7.57 (1H, d), 7.85-7.90 (2H, m), 9.25 (1H, s)

MS m/e [M+Na]⁺ 403.

Intermediate#56: methyl 4-[4-(2-adamantylcarbamoyl)-5-tert-butyl-pyrazol-1-yl]benzoate

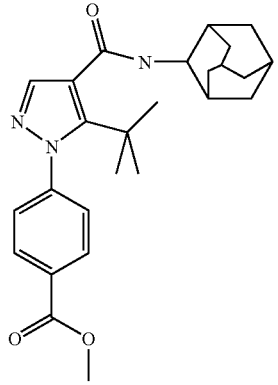

Methyl 4-hydrazinylbenzoate hydrochloride (Intermediate#123) (3.04 g, 15.00 mmol) was added in one portion to (2)—N-(2-adamantyl)-2-(dimethylaminomethylidene)-4,4-dimethyl-3-oxo-pentanamide (Intermediate#58) (4.99 g, 15 mmol) in ethanol (100 mL). 5 drops of acetic acid were added and the resulting solution was stirred at 80° C. for 2 hours. The reaction mixture was concentrated and diluted with EtOAc (500 mL), and washed sequentially with water (200 mL), and saturated brine (200 mL). The organic layer was dried over MgSO4, filtered and evaporated to afford crude product.

The crude product was purified by flash silica chromatography, elution gradient 0 to 50% EtOAc in isohexane. Pure fractions were evaporated to dryness to afford methyl 4-[4-(2-adamantylcarbamoyl)-5-tert-butyl-pyrazol-1-yl]benzoate (4.66 g, 71.3%) as a yellow solid.

1H NMR (400.13 MHz, DMSO-$d_6$) δ 1.19 (9H, s), 1.50 (2H, d), 1.69-1.95 (10H, m), 2.09 (2H, d), 3.91 (3H, s), 3.99 (1H, d), 7.53-7.56 (2H, m), 7.62 (1H, s), 8.09-8.12 (2H, m), 8.20 (1H, d)

m/z (ESI+) (M+H)+=436

Intermediate#56 may also be prepared as follows:

2-(4-(Methoxycarbonyl)phenyl)hydrazinium chloride (Intermediate#123) (1 equiv.) and then acetic acid (0.023 equivs.) were added to a solution of (2Z)—N-(2-adamantyl)-2-(dimethylamino-methylidene)-4,4-dimethyl-3-oxo-pentanamide (Intermediate#58) (1 equiv.) in methanol (200 vols.), under nitrogen. The mixture stirred under reflux for 1.5 hours, cooled, concentrated to below 3.5 vols. and the resulting suspension diluted with ethyl acetate (96 vols.). The suspension was washed with water (34.4 vols.) giving a solution which was washed with brine (34.4 vols.), dried (MgSO$_4$) and concentrated to dryness. The crude product was slurried in MTBE (9 vols.) and stirred for 15 minutes. The pale yellow solid was filtered, washed with MTBE (11.4 vols.) and dried under vacuum at 60° C.

TLC DCM:MeOH, 9:1, Product $R_f$ 0.86 (trace impurity $R_f$ 0.68)

mp 193.6-194.5° C.

Intermediate#57: methyl 4-[4-(2-adamantylcarbamoyl)-5-(1-methylcyclopropyl)pyrazol-1-yl]benzoate

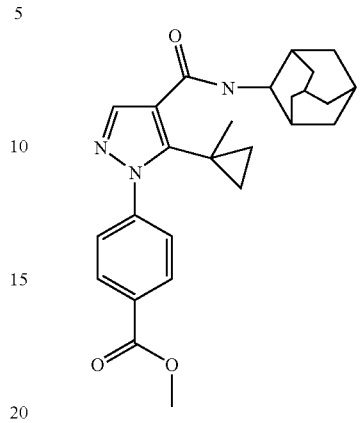

Methyl 4-hydrazinylbenzoate hydrochloride (Intermediate#123) (0.809 g, 3.99 mmol) was added in one portion to (Z)—N-(2-adamantyl)-3-dimethylamino-2-(1-methylcyclopropanecarbonyl)prop-2-enamide (Intermediate#59), 1.320 g, 3.99 mmol) in ethanol (30 mL). 5 drops of acetic acid were added and the resulting solution was stirred at 80° C. for 2 hours. The reaction mixture was concentrated and diluted with EtOAc (100 mL), and washed sequentially with water (50 mL), and saturated brine (50 mL). The organic layer was dried over MgSO4, filtered and evaporated to afford crude product.

The crude product was purified by flash silica chromatography, elution gradient 0 to 50% EtOAc in isohexane. Pure fractions were evaporated to dryness to afford methyl 4-[4-(2-adamantylcarbamoyl)-5-(1-methylcyclopropyl)pyrazol-1-yl]benzoate (1.221 g, 70.5%) as a cream solid.

m/z (ESI+) (M+H)+=434; HPLC $t_R$=2.98 min.

1H NMR (400.13 MHz, DMSO-$d_6$) δ 0.48-0.51 (2H, m), 0.67-0.69 (2H, m), 1.54-1.57 (5H, m), 1.73 (2H, s), 1.83-1.86 (6H, m), 1.97 (2H, s), 2.04-2.07 (2H, m), 3.90 (3H, s), 4.05-4.10 (1H, m), 7.50 (1H, d), 7.71 (2H, d), 8.09 (1H, s), 8.13 (2H, d)

Intermediate#58: (2)—N-(2-adamantyl)-2-(dimethylaminomethylidene)-4,4-dimethyl-3-oxo-pentanamide

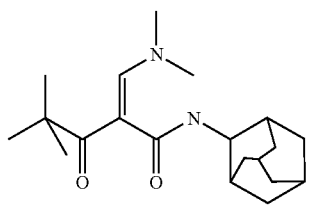

N,N-Dimethylformamide dimethyl acetal (3.02 mL, 22.71 mmol) was added to a stirred suspension of N-(2-adamantyl)-4,4-dimethyl-3-oxo-pentanamide (Intermediate#60) (5.25 g, 18.93 mmol) in 1,4-dioxane (50 mL) under nitrogen. The resulting mixture was stirred at 100° C. for 2 hours. The reaction mixture was evaporated to dryness and the resulting pale cream solid was dried under vacuum to afford (2) —N-(2-adamantyl)-2-(dimethylaminomethylidene)-4,4-dimethyl-3-oxo-pentanamide (5.83 g, 93%).

1H NMR (400.13 MHz, DMSO-$d_6$) δ 1.13 (9H, s), 1.47 (2H, d), 1.69-1.83 (10H, m), 2.03 (2H, d), 2.92 (6H, s), 3.90 (1H, d), 7.24 (1H, s), 7.94 (1H, d)

m/z (ESI+) (M+H)+=333

Intermediate#58 may also be prepared as follows:

N,N-Dimethylformamide dimethyl acetal (1.2 equivs.) was added to a solution of N-(2-adamantyl)-4,4-dimethyl-3-oxo-pentanamide (Intermediate#60) (1 equiv.) in 1,4-dioxane (9.6 vols.) under nitrogen. The mixture was heated under reflux for five hours and then cooled to room temperature. The solvent was removed in vacuo and the pale yellow solid used directly in the next stage.

TLC Hexane:EtOAc, 1:1, Product $R_f$ 0.94 (impurities: $R_f$ 0.06+0.66)

mp 143.6-147.6° C.

Intermediate#59: (Z)—N-(2-adamantyl-1)-3-dimethylamino-2-(1-methylcyclopropanecarbonyl)prop-2-enamide

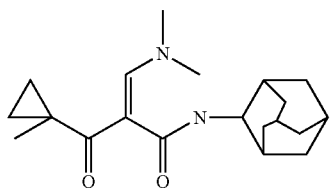

Prepared from N-(2-adamantyl)-3-(1-methylcyclopropyl)-3-oxo-propanamide (Intermediate#61) by the same process as used for Intermediate #58

1H NMR (400.13 MHz, DMSO-$d_6$) δ 0.54-0.55 (2H, m), 0.91-0.94 (2H, m), 1.26 (3H, s), 1.51 (2H, d), 1.69 (2H, s), 1.72-1.85 (8H, m), 1.92 (2H, d), 3.00 (6H, s), 3.90-3.92 (1H, m), 7.57 (1H, s), 8.08 (1H, s)

(Intermediate#60): N-(2-adamantyl)-4,4-dimethyl-3-oxo-pentanamide

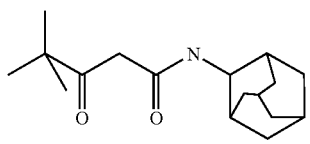

A 1M solution of solution of lithium bis(trimethylsilyl) amide in THF (22.84 ml, 22.84 mmol) was added to THF (25 mL) and cooled under nitrogen to −78° C. A solution of 3,3-dimethyl-2-butanone (2.287 g, 22.84 mmol) in THF (25 mL) was added drop wise over a period of 5 minutes. The resulting solution was stirred at −78° C. under nitrogen for 15 minutes. A solution of 2-isocyanatoadamantane (prepared from 2-adamantylamine hydrochloride by the method of R. Reck & C. Jochims Chem. Ber. 115 (1982) p 864) (3.68 g, 20.76 mmol) in THF (20 mL) was added over a period of 5 minutes. The resulting solution was stirred at −78° C. for 1 hour and then allowed to warm to 20° C. over 1 h. The reaction mixture was poured into saturated NH$_4$Cl (150 mL) and extracted with EtOAc (2×100 mL), the organic layer was washed with water (50 mL) and brine (50 mL) dried over MgSO4, filtered and evaporated to afford a yellow oil. The crude product was purified by flash silica chromatography, elution gradient 0 to 50% EtOAc in isohexane. Pure fractions were evaporated to dryness to afford N-(2-adamantyl)-4,4-dimethyl-3-oxo-pentanamide (4.64 g, 81%) as a white solid.

$^1$H NMR (400.13 MHz, DMSO-$d_6$) δ 1.08-1.09 (9H, m), 1.50 (2H, d), 1.66-1.89 (10H, m), 1.95-2.00 (2H, m), 3.53 (1.4H, s), 3.80-3.94 (1H, m), 5.30 (0.3H, s), 7.77-7.87 (1H, m), 14.43 (0.3H, s) (2:1 mixture of keto and enol forms)

m/z (ESI+) (M+H)+=278

Intermediate #60 may also be prepared as follows:

Aqueous sodium hydroxide solution (3M) (5 vols.) was added to a stirred suspension of 2-adamantylamine hydrochloride (1 equiv.) in water (5 vols.). DCM (5 vols.) was added to the resulting thick suspension and the phases separated. The aqueous was extracted with DCM (4×5 vols.) and the combined organics concentrated to give the free amine as a white solid.

Ethyl pivaloylacetate (1 equiv.) was added to a suspension of the free amine in xylenes (6.5 vols.), under nitrogen, and the mixture stirred under reflux for 6.5 hours. The batch was cooled to room temperature and concentrated to dryness. The residue was purged with toluene (3×1 vol.) followed by hexane (3×1 vol.). The resulting solid was digested in hexane at 50° C. for five minutes and then cooled to room temperature. The white solid was filtered, washed with hexane (2 vols.) and dried in air.

TLC Hexane:EtOAc, 1:1, Product $R_f$ 0.66 mp 124.5-125.1° C.

Intermediate#61: N-(2-adamantyl)-3-(1-methylcyclopropyl)-3-oxo-propanamide

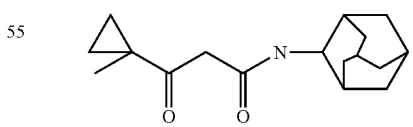

Prepared from 1-(1-methylcyclopropyl)ethanone by the same process as used for Intermediate#60 m/z (ESI+) (M+H)+=276; HPLC $t_R$=2.26 min.

1H NMR (400.13 MHz, DMSO-$d_6$) δ 0.76-0.78 (2H, m), 1.18-1.20 (2H, m), 1.25 (3H, s), 1.50 (2H, d), 1.70-1.80 (11H, m), 1.95 (2H, d), 3.82 (1H, d), 7.83 (1H, d)

Intermediate#62: methyl 4-[4-(2-adamantylcarbamoyl)-5-cyclopentyl-pyrazol-1-yl]benzoate

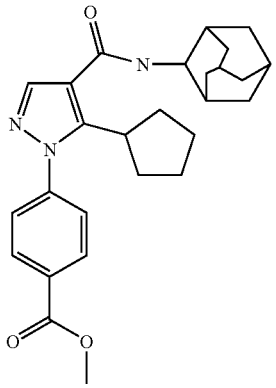

Methyl 4-hydrazinylbenzoate hydrochloride (Intermediate#123) (0.712 g, 3.51 mmol) was added in one portion to (Z)—N-(2-adamantyl)-2-(cyclopentanecarbonyl)-3-dimethylamino-prop-2-enamide (Intermediate#67), 1.21 g, 3.51 mmol) in ethanol (30 mL). 5 drops of acetic acid were added and the resulting solution was stirred at 80° C. for 2 hours and then cooled to ambient giving a precipitate. The reaction mixture was filtered and the product recovered, washed with ethanol (10 mL) and water (10 mL) before being dried under vacuum to give methyl 4-[4-(2-adamantylcarbamoyl)-5-cyclopentyl-pyrazol-1-yl]benzoate (0.620 g, 39.4%) as a white solid.

1H NMR (400.13 MHz, DMSO-$d_6$) δ 1.48-1.53 (4H, m), 1.71-1.85 (12H, m), 1.94 (2H, s), 2.02-2.12 (4H, m), 2.98-3.09 (1H, m), 3.90 (3H, s), 3.98-4.03 (1H, m), 7.57-7.60 (2H, m), 7.74-7.76 (1H, m), 8.10-8.15 (3H, m)

m/z (ESI+) (M+H)+=448; HPLC $t_R$=3.26 min.

The same process as used for Intermediate#62 prepared the following intermediates from the appropriate starting material.

| Structure | Int # | Name | $^1$H NMR δ | MS m/e MH+ |
|---|---|---|---|---|
| 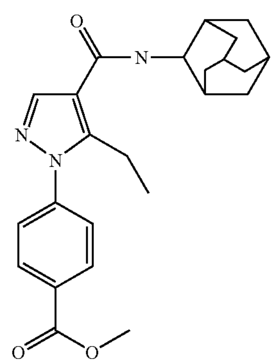 | 63 | methyl 4-[4-(2-adamantylcarbamoyl)-5-ethylpyrazol-1-yl]benzoate | 1H NMR (400.13 MHz, DMSO-$d_6$) δ 1.03 (3 H, t), 1.53 (2 H, d), 1.72 (2 H, s), 1.84 (6 H, d), 1.95 (2 H, s), 2.11 (2 H, d), 2.98 (2 H, q), 3.90 (3 H, s), 4.04 (1 H, t), 7.59-7.61 (1 H, m), 7.65-7.68 (2 H, m), 8.12-8.15 (2 H, m), 8.30 (1 H, s) | 408 |
| 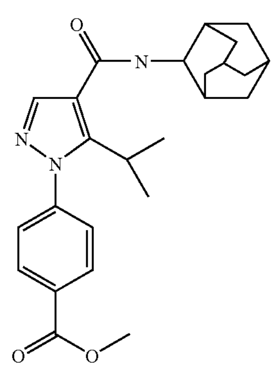 | 64 | methyl 4-[4-(2-adamantylcarbamoyl)-5-propan-2-ylpyrazol-1-yl]benzoate | H NMR (400.13 MHz, DMSO-$d_6$) δ 1.30 (6 H, d), 1.52 (2 H, d), 1.73 (2 H, s), 1.82-1.86 (6 H, m), 1.97 (2 H, s), 2.11 (2 H, d), 3.11-3.18 (1 H, m), 3.91 (3 H, s), 4.00-4.05 (1 H, m), 7.57 (2 H, d), 7.67 (1 H, d), 8.08 (1 H, s), 8.13 (2 H, d) | 422 |

| Structure | Int # | Name | ¹H NMR δ | MS m/e MH⁺ |
|---|---|---|---|---|
| 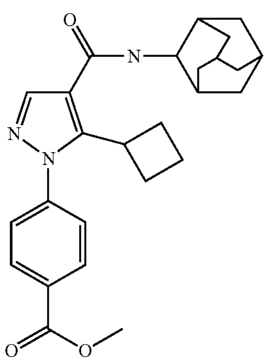 | 65 | methyl 4-[4-(2-adamantylcarbamoyl)-5-cyclobutylpyrazol-1-yl]benzoate | 1H NMR (400.13 MHz, DMSO-d₆) δ 1.51-1.54 (2 H, m), 1.65 (1 H, q), 1.72 (2 H, s), 1.76-1.85 (7 H, m), 1.96 (2 H, s), 2.04-2.15 (4 H, m), 2.18-2.26 (2 H, m), 3.82 (1 H, q), 3.90 (3 H, s), 4.00-4.06 (1 H, m), 7.59 (2 H, d), 7.81 (1 H, d), 7.95 (1 H, s), 8.11 (2 H, d) | 434 |

Intermediate#66: N-(2-adamantyl)-1-(4-cyanophenyl)-5-methyl-pyrazole-4-carboxamide

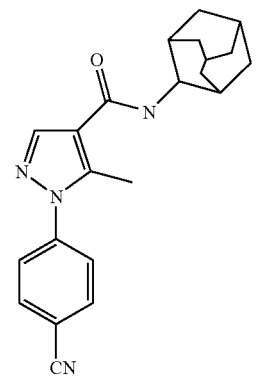

Acetic acid (0.031 mL, 0.50 mmol) was added in one portion to (2E)-N-(2-adamantyl)-2-(dimethylaminomethylidene)-3-oxo-butanamide (Intermdiate#71) (1.45 g, 4.99 mmol) and 4-cyanophenylhydrazine hydrochloride (0.847 g, 4.99 mmol) in ethanol (40 mL). The resulting suspension was stirred at 80° C. for 3 hours. The reaction mixture was concentrated and diluted with EtOAc (75 mL), and washed sequentially with water (50 mL) and saturated brine (50 mL). The organic layer was dried over MgSO4, filtered and evaporated to afford crude product.

The crude product was purified by flash silica chromatography, elution gradient 20 to 50% EtOAc in isohexane. Pure fractions were evaporated to dryness to afford N-(2-adamantyl)-1-(4-cyanophenyl)-5-methyl-pyrazole-4-carboxamide (1.3 g, 72%) as an orange solid.

1H NMR (400.13 MHz, DMSO-d₆) δ 1.45-1.58 (2H, m), 1.70-1.9 (8H, m), 1.92-1.99 (2H, m), 2.05-2.15 (2H, m), 2.57 (3H, s), 4.00-4.06 (1H, m), 7.59 (1H, d), 7.79 (2H, d), 8.05 (2H, d), 8.32 (1H, s)

m/z (ESI+) (M+H)+=361;

Intermediate#67: (Z)—N-(2-adamantyl)-2-(cyclopentanecarbonyl)-3-dimethylamino-prop-2-enamide

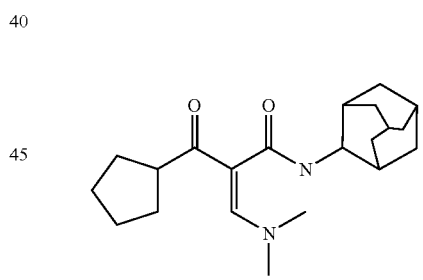

N,N-Dimethylformamide dimethyl acetal (0.587 mL, 4.42 mmol) was added to N-(2-adamantyl)-3-cyclopentyl-3-oxo-propanamide (Intermediate#72), (1.023 g, 3.53 mmol) in 1,4-dioxane (25 mL). The resulting solution was stirred at 100° C. for 2 hours. The resulting mixture was evaporated to dryness to afford (Z)—N-(2-adamantyl)-2-(cyclopentanecarbonyl)-3-dimethylamino-prop-2-enamide (1.210 g, 99%).

1H NMR (400.13 MHz, DMSO-d₆) δ 1.45-1.50 (4H, m), 1.54-1.68 (8H, m), 1.72-1.85 (8H, m), 2.00 (2H, d), 2.97 (6H, s), 3.05-3.15 (1H, m), 3.95 (1H, d), 7.42 (1H, s), 8.30 (1H, d)

The same process as used for Intermediate#67 prepared the following intermediates from the appropriate starting material.

| Structure | Int # | Name | ¹H NMR δ | MS m/e MH⁺ |
|---|---|---|---|---|
| 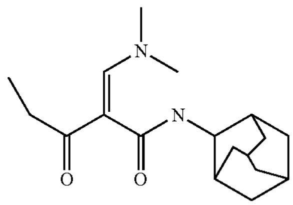 | 68 | (2Z)-N-(2-adamantyl)-2-(dimethylamino-methylidene)-3-oxopentanamide | 1H NMR (300.073 MHz, (3 H, t), 1.48 (2 H, d), 1.68 (2 H, s), 1.77-1.81 (8 H, m), 1.95-2.00 (2 H, m), 2.38 (2 H, q), 2.97 (6 H, s), 3.92 (1 H, d), 7.40 (1 H, s), 8.25 (1 H, d) | 305 |
| 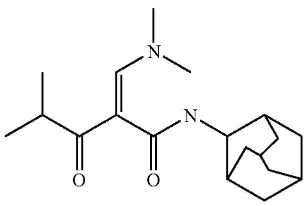 | 69 | (2Z)-N-(2-adamantyl)-2-(dimethylamino-methylidene)-4-methyl-3-oxopentanamide | 1H NMR (400.13 MHz, DMSO-d₆) δ 0.95-1.00 (6 H, m), 1.50 (2 H, d), 1.70 (2 H, s), 1.76-1.78 (4 H, m), 1.79 (2 H, s), 1.82 (3 H, s), 2.01 (2 H, d), 2.93-2.99 (6 H, m), 3.58 (3 H, s), 3.95 (1 H, d), 7.40 (1 H, s), 8.24 (1 H, d) | |
| 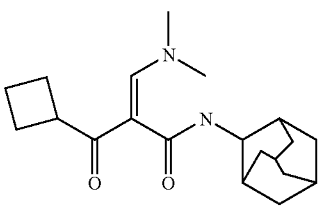 | 70 | (Z)-N-(2-adamantyl)-2-(cyclobutanecarbonyl)-3-dimethylaminoprop-2-enamide | 1H NMR (400.13 MHz, DMSO-d₆) δ 1.51 (2 H, d), 1.67-1.71 (2 H, m), 1.78-1.87 (8 H, m), 1.94-2.00 (4 H, m), 2.11-2.21 (2 H, m), 2.98 (5 H, s), 3.29 (3 H, s), 3.53 (1 H, t), 3.93 (1 H, d), 7.37 (1 H, s), 8.29 (1 H, d) | |
| 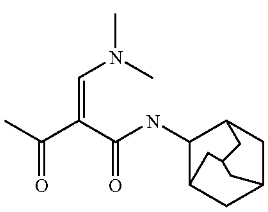 | 71 | (2Z)-N-(2-adamantyl)-2-(dimethylamino-methylidene)-3-oxo-butanamide | 1H NMR (400.13 MHz, DMSO-d₆) δ 1.46-1.52 (2 H, m), 1.65-1.70 (2 H, m), 1.72-1.85 (8 H, m), 1.92-2.00 (2 H, m), 2.04 (3 H, s), 2.99 (6 H, s), 3.91-3.96 (1 H, m), 7.44 (1 H, s), 8.35 (1 H, d) | |

Intermediate#72:
N-(2-adamantyl)-3-cyclopentyl-3-oxo-propanamide

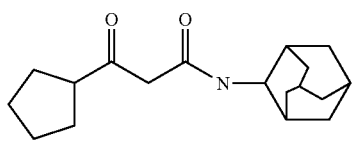

2-Adamantanamine hydrochloride (1.641 g, 8.74 mmol) was added to 5-(cyclopentanecarbonyl)-2,2-dimethyl-1,3-dioxane-4,6-dione (Intermediate#77), (2.1 g, 8.74 mmol) and N-Ethyldiisopropylamine (1.512 mL, 8.74 mmol) in toluene (30 mL). The resulting suspension was stirred at 110° C. for 2 hours. The reaction mixture was diluted with EtOAc (100 mL), and washed sequentially with 2M HCl (20 mL), and water (2×50 mL). The organic layer was dried over MgSO4, filtered and evaporated to afford crude product. The crude product was purified by flash silica chromatography, elution gradient 0 to 100% EtOAc in isohexane. Pure fractions were evaporated to dryness to afford N-(2-adamantyl)-3-cyclopentyl-3-oxo-propanamide (1.030 g, 40.7%) as a brown oil which crystallised on standing.

1H NMR (400.13 MHz, DMSO-d₆) δ 1.46-1.59 (7H, m), 1.60-1.78 (16H, m), 1.90-2.00 (2H, m), 2.95-3.03 (1H, m), 3.84 (0.9H, d), 3.90 (0.1H, d), 7.78 (0.1H, d), 7.93 (0.9H, d), 14.21 (0.1H, s) 9:1 ketone:enol form The same process as used for Intermediate#72 prepared the following intermediates from the appropriate starting material.

| Structure | Int # | Name | ¹H NMR δ |
|---|---|---|---|
| 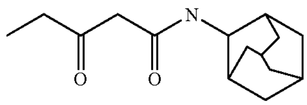 | 73 | N-(2-adamantyl)-3-oxopentanamide | 1H NMR (400.13 MHz, CDCl₃) δ 1.11 (3 H, t), 1.67 (2 H, d), 1.77 (2 H, s), 1.80-1.98 (10 H, d), 2.59 (2 H, q), 3.46 (2 H, s), 4.08-4.10 (1 H, m), 7.70 (1 H, s) |
| 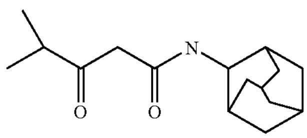 | 74 | N-(2-adamantyl)-4-methyl-3-oxopentanamide | 1H NMR (400.13 MHz, DMSO-d₆) δ 0.98-1.06 (6 H, m), 1.48-1.54 (2 H, m), 1.70-1.73 (3 H, m), 1.75-1.81 (4 H, m), 1.79 (4 H, d), 1.95-2.00 (2 H, m), 2.68-2.75 (1 H, m), 3.46 (1 H, s), 3.84 (1 H, d), 7.87 (1 H, d) |
| 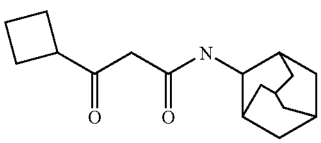 | 75 | N-(2-adamantyl)-3-cyclobutyl-3-oxopropanamide | 1H NMR (400.13 MHz, DMSO-d₆) δ 1.50-1.53 (3 H, m), 1.65-1.73 (3 H, m), 1.74-1.81 (8 H, m), 1.86-1.98 (4 H, m), 2.02-2.10 (4 H, m), 3.29 (1 H, s), 3.84 (1 H, d), 7.88 (1 H, d) |
| 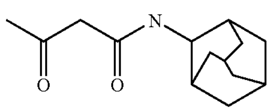 | 76 | N-(2-adamantyl)-3-oxo-butanamide | 1H NMR (400.13 MHz, DMSO-d₆) δ 1.48-1.54 (2 H, m), 1.69-1.85 (10 H, m), 1.92-2.00 (2 H, s), 2.13 (3 H, s), 3.38 (2 H, s), 3.84 (1 H, d), 7.95 (1 H, d) |

Intermediate#77: 5-(cyclopentanecarbonyl)-2,2-dimethyl-1,3-dioxane-4,6-dione

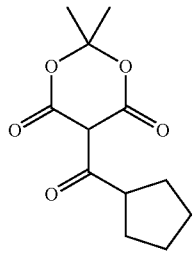

A solution of cyclopentanecarbonyl chloride (1.100 mL, 9.05 mmol) in DCM (5 mL) was added dropwise to a stirred solution of isopropylidene malonate (1.304 g, 9.05 mmol), and pyridine (1.464 mL, 18.10 mmol) in DCM (20 mL) at 5° C., over a period of 10 minutes under nitrogen. The resulting solution was stiffed at 5° C. for 1 hour and then allowed to warm to 20° C. and stirred for another hour. The reaction mixture was diluted with DCM (100 mL), and washed sequentially with 2M HCl (2×50 mL), water (50 mL), and saturated brine (50 mL). The organic layer was dried over MgSO4, filtered and evaporated to afford crude product, 5-(cyclopentanecarbonyl)-2,2-dimethyl-1,3-dioxane-4,6-dione (2.100 g, 97%) as a brown oil.

1H NMR (400.13 MHz, DMSO-d₆) δ 1.51-1.60 (5H, m), 1.61-1.68 (3H, s), 1.70-1.79 (4H, m), 1.84-1.98 (2H, m), 2.89-3.00 (1H, m), 4.04 (1H, s

The same process as used for Intermediate#77 prepared the following intermediates from the appropriate starting materials.

| Structure | Int # | Name | ¹H NMR δ |
|---|---|---|---|
| 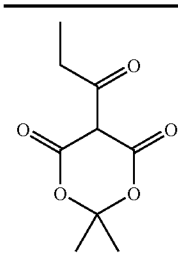 | 78 | 2,2-dimethyl-5-propanoyl-1,3-dioxane-4,6-dione | Used crude |
| 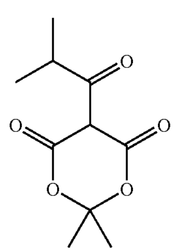 | 79 | 2,2-dimethyl-5-(2-methylpropanoyl)-1,3-dioxane-4,6-dione | 1H NMR (400.13 MHz, DMSO-d₆) δ 1.02-1.08 (1 H, m), 1.15-1.18 (6 H, m), 1.70-1.72 (6 H, m), 3.92-3.99 (1 H, m) |
| 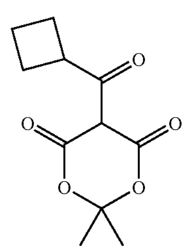 | 80 | 5-(cyclobutanecarbonyl)-2,2-dimethyl-1,3-dioxane-4,6-dione | 1H NMR (400.13 MHz, DMSO-d₆) δ 1.68 (6 H, s), 1.82-1.89 (2 H, m), 2.09 (2 H, s), 2.05-2.13 (2 H, m), 2.18-2.32 (5 H, m), 4.30-4.35 (1 H, m) |

| Structure | Int # | Name | ¹H NMR δ |
|---|---|---|---|
| 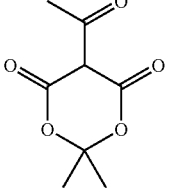 | 81 | 5-acetyl-2,2-dimethyl-1,3-dioxane-4,6-dione | Used crude |

Intermediate#82: 1-(4-bromophenyl)-5-tert-butyl-N-cyclohexyl-1H-pyrazole-4-carboxamide

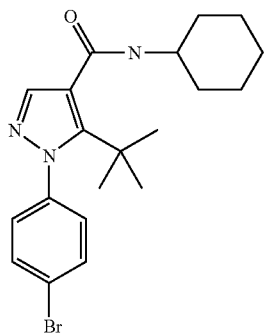

Ethyl (2)-2-(dimethylaminomethylidene)-4,4-dimethyl-3-oxo-pentanoate (Intermediate #83) (1.24 g, 5.88 mmol) was dissolved in ethanol (20 mL). 4-bromophenylhydrazine HCl (1.32 g, 5.88 mmol) and DIPEA (1.02 mL, 5.88 mmol) were added. The mixture was heated to reflux for 2 h cooled to ambient and evaporated under reduced pressure. The residue was dissolved in DCM (50 mL), washed with water (2×10 mL), dried (MgSO4) and evaporated to afford crude product. The crude product was purified by flash silica chromatography, elution gradient 0 to 25% EtOAc in isohexane. Pure fractions were evaporated to dryness to afford 1-(4-bromophenyl)-5-tert-butyl-N-cyclohexyl-1H-pyrazole-4-carboxamide (627 mg, 32%)

1H NMR (300.073 MHz, DMSO-d₆) δ 1.23 (9H, s), 1.29 (3H, t), 4.24 (2H, q), 7.39-7.41 (2H, m), 7.69-7.72 (2H, m), 7.92 (1H, s)

m/z (ESI+) (M+H)+=353

Intermediate #83: Ethyl (2)-2-(dimethylaminomethylidene)-4,4-dimethyl-3-oxo-pentanoate

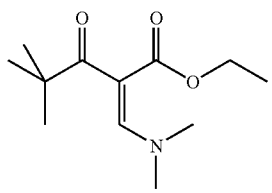

Ethyl pivaloylacetate (1.72 g, 10 mmol) and N,N-dimethylformamide dimethylacetal (1.68 mL, 12.5 mmol) were dissolved in dioxan (20 mL) and heated to reflux for 3 h. The reaction mixture was cooled to ambient and evaporated under reduced pressure to leave crude product. The crude product was purified by flash chromatography on silica gel (elution gradient 0 to 100% EtOAc in hexane) to afford Ethyl (2)-2-(dimethylaminomethylidene)-4,4-dimethyl-3-oxo-pentanoate as a colourless oil that crystallised on standing. (1.24 g, 54%)

1H NMR (300.073 MHz, DMSO-d₆) δ 1.11 (9H, d), 1.18 (3H, t), 2.82 (6H, s), 4.04 (2H, q), 7.31 (1H, s)

m/z (ESI+) (M+H)+=228

Intermediate#84: methyl 4-[4-(2-adamantylcarbamoyl)-5-cyclohexylsulfanyl-pyrazol-1-yl]benzoate

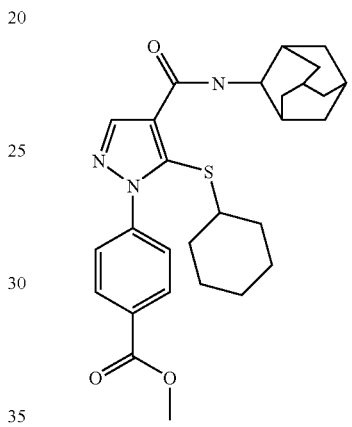

1-(3-Dimethylaminopropyl)-3-ethylcarbodiimide hydrochloride (191 mg, 1.00 mmol) was added in one portion to 5-(cyclohexylthio)-1-(4-(methoxycarbonyl)phenyl)-1H-pyrazole-4-carboxylic acid (Intermediate#88) (300 mg, 0.83 mmol), 2-Adamantanamine hydrochloride (172 mg, 0.92 mmol) and N-Ethyldiisopropylamine (0.432 mL, 2.50 mmol) in DMF (7 mL) at 20° C. under nitrogen. The resulting mixture was stirred at 20° C. for 18 hours.

The reaction mixture was diluted with EtOAc (75 mL), and washed sequentially with water (4×25 mL) and saturated brine (25 mL). The organic layer was dried over MgSO4, filtered and evaporated to afford crude product. The crude product was purified by flash silica chromatography, elution gradient 0 to 50% EtOAc in isohexane. Pure fractions were evaporated to dryness to afford methyl 4-[4-(2-adamantylcarbamoyl)-5-cyclohexylsulfanyl-pyrazol-1-yl]benzoate (349 mg, 85%) as a white crystalline solid.

1H NMR (300.073 MHz, DMSO-d6) δ 1.05 (5H, d), 1.39-1.54 (5H, m), 1.62 (2H, d), 1.73 (2H, s), 1.83 (6H, s), 1.94-2.01 (4H, m), 2.92 (1H, s), 3.89 (3H, s), 4.09 (1H, d), 7.76 (2H, d), 8.04 (1H, d), 8.12 (2H, d), 8.17 (1H, s)

m/z (ESI+) (M+H)+=494

The following Intermediates were prepared in a similar manner to Intermediate #84 from 5-(cyclohexylthio)-1-(4-(methoxycarbonyl)phenyl)-1H-pyrazole-4-carboxylic acid (Intermediate#88) and an appropriate amine.

| Structure | Int. # | Name | ¹H NMR δ | MS m/e MH⁺ |
|---|---|---|---|---|
| 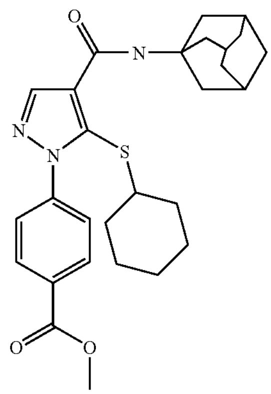 | 85 | methyl 4-[4-(1-adamantylcarbamoyl)-5-cyclohexylsulfanyl-pyrazol-1-yl]benzoate | 1H NMR (400.13 MHz, DMSO-d6) δ 1.05-1.17 (5 H, m), 1.42 (1 H, s), 1.51-1.63 (4 H, m), 1.68 (6 H, s), 2.02-2.12 (9 H, m), 2.98 (1 H, s), 3.91 (3 H, s), 7.53 (1 H, s), 7.72-7.74 (2 H, m), 8.13 (3 H, d) | (ESI+) 494 |
| 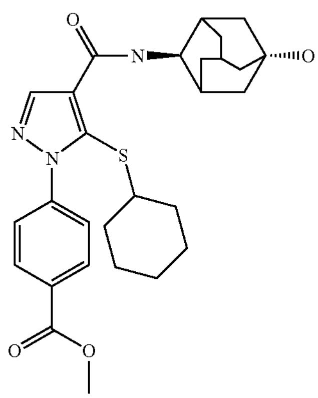 | 86 | methyl 4-[5-cyclohexylsulfanyl-4-[[(1S,3R)-5-hydroxy-2-adamantyl]carbamoyl]pyrazol-1-yl]benzoate | 1H NMR (400.13 MHz, DMSO-d6) δ 1.02-1.10 (5 H, m), 1.41-1.56 (7 H, m), 1.67 (4 H, d), 1.76 (2 H, d), 1.89 (2 H, d), 2.08 (3 H, s), 2.93 (1 H, s), 3.91 (3 H, s), 4.03 (1 H, d), 4.43 (1 H, s), 7.76-7.79 (2 H, m), 7.97 (1 H, d), 8.13-8.15 (2 H, m), 8.18 (1 H, s) | (ESI+) 510 |
| 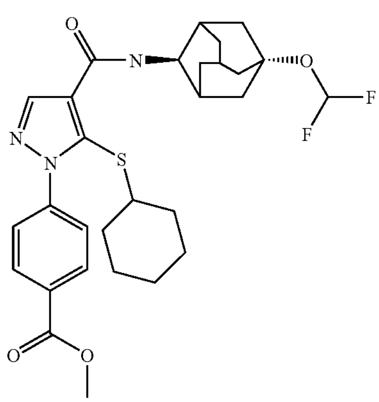 | 87 | methyl 4-[5-cyclohexylsulfanyl-4-[[5-(difluoromethoxy)-2-adamantyl]carbamoyl]pyrazol-1-yl]benzoate | 1H NMR (400.13 MHz, DMSO-d6) δ 1.00-1.10 (5 H, m), 1.41 (1 H, s), 1.45-1.58 (6 H, m), 1.91-1.99 (6 H, m), 2.05 (2 H, d), 2.18 (3 H, d), 2.95 (1 h, d), 3.91 (3 H, s), 4.10 (1 H, t), 6.88 (1 H, t), 7.75-7.79 (2 H, m), 7.99 (1 H, d), 8.12-8.16 (2 H, m), 8.19 (1 H, s) | (ESI+) 560 |

Intermediate #88: 5-cyclohexylsulfanyl-1-(4-methoxycarbonylphenyl)pyrazole-4-carboxylic acid

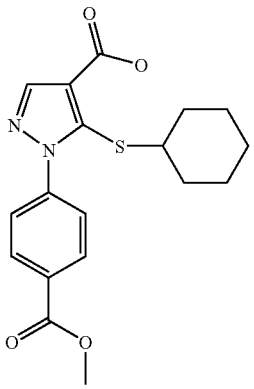

Trifluoroacetic acid (4.72 mL, 61.46 mmol) was added to tert-butyl 5-(cyclohexylthio)-1-(4-(methoxycarbonyl)phenyl)-1H-pyrazole-4-carboxylate (Intermediate#89) (2.56 g, 6.15 mmol) in CH$_2$Cl$_2$ (40 mL) The resulting solution was stirred at 20° C. for 24 hours. The reaction mixture was evaporated to dryness, re-dissolved in dioxan (20 mL) and re-evaporated to dryness to afford 5-(cyclohexylthio)-1-(4-(methoxycarbonyl)phenyl)-1H-pyrazole-4-carboxylic acid (2.25 g, 100%) as a white crystalline solid.

1H NMR (400.13 MHz, DMSO-d6) δ 1.04-1.11 (5H, m), 1.42 (1H, s), 1.51 (2H, s), 1.59 to (2H, d), 3.31-3.22 (1H, m), 3.91 (3H, s), 7.70-7.73 (2H, m), 8.11-8.15 (2H, m), 8.19 (1H, s), 12.66 (1H, s)

MS m/z (ESI+) (M+H)+=361.

Intermediate #89: tert-butyl 5-cyclohexylsulfanyl-1-(4-methoxycarbonylphenyl)pyrazole-4-carboxylate

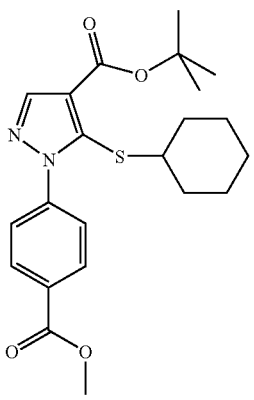

Sodium bis(trimethylsilyl)amide (10.69 mL, 10.69 mmol) was added dropwise to Cyclohexanethiol (1.307 mL, 10.69 mmol) in DMF (35 mL) under nitrogen. The resulting solution was stiffed at 20° C. for 30 minutes. A solution of tert-butyl 5-chloro-1-(4-(methoxycarbonyl)phenyl)-1H-pyrazole-4-carboxylate (Intermediate #9) (3 g, 8.91 mmol) in DMF (10 mL) was then added dropwise and the resulting mixture was stirred at 20° C. for 2 hours.

The reaction mixture was diluted with EtOAc (200 mL), and washed sequentially with water (4×50 mL) and saturated brine (50 mL). The organic layer was dried over MgSO4, filtered and evaporated to afford crude product.

The crude product was purified by flash silica chromatography, elution gradient 0 to 25% EtOAc in isohexane. Pure fractions were evaporated to dryness to afford tert-butyl 5-(cyclohexylthio)-1-(4-(methoxycarbonyl)phenyl)-1H-pyrazole-4-carboxylate (2.56 g, 69.0%) as a colourless oil which crystallised on standing.

1H NMR (400.13 MHz, DMSO-d6) δ 0.95-1.05 (5H, m), 1.35 (1H, s), 1.42-1.55 (13H, d), 3.12 (1H, d), 3.81 (3H, s), 7.69-7.72 (2H, m), 8.11-8.14 (2H, m), 8.16 (1H, s)

m/z (ESI+) (M+H)+=417

Intermediate #90: methyl 4-[4-(2-adamantylcarbamoyl)-5-cyclopentylsulfanyl-pyrazol-1-yl]benzoate

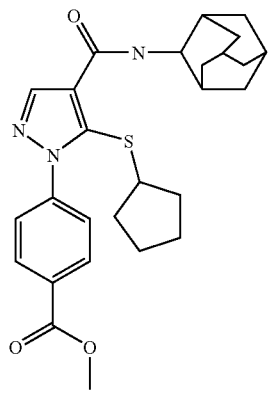

1-(3-Dimethylaminopropyl)-3-ethylcarbodiimide hydrochloride (199 mg, 1.04 mmol) was added in one portion to 5-(cyclopentylthio)-1-(4-(methoxycarbonyl)phenyl)-1H-pyrazole-4-carboxylic acid (Intermediate#93) (300 mg, 0.87 mmol), 2-Adamantanamine hydrochloride (179 mg, 0.95 mmol), 1-Hydroxybenzotriazole (140 mg, 1.04 mmol) and N-Ethyldiisopropylamine (0.450 mL, 2.60 mmol) in DMF (7 mL) at 20° C. under nitrogen. The resulting mixture was stirred at 20° C. for 18 hours.

The reaction mixture was diluted with EtOAc (75 mL), and washed sequentially with water (4×25 mL) and saturated brine (25 mL). The organic layer was dried over MgSO4, filtered and evaporated to afford crude product.

The crude product was purified by flash silica chromatography, elution gradient 0 to 50% EtOAc in isohexane. Pure fractions were evaporated to dryness to afford methyl 4-[4-(2-adamantylcarbamoyl)-5-cyclopentylsulfanyl-pyrazol-1-yl]benzoate (336 mg, 81%) as a white crystalline solid.

1H NMR (400.13 MHz, DMSO-d6) δ 1.17-1.25 (2H, m), 1.35-1.42 (4H, m), 1.65 (4H, d), 1.74 (2H, s), 1.87 (6H, d), 1.96-2.02 (4H, m), 3.25-3.35 (1H, m), 3.91 (3H, s), 4.12 (1H, t), 7.78-7.82 (2H, m), 8.08 (1H, d), 8.13-8.16 (2H, m), 8.19 (1H, s)

m/z (ESI+) (M+H)+=480 m/z (ESI+) (M+H)+=480

The following Intermediates were prepared in a similar manner to Intermediate #90 from 5-(cyclopentylthio)-1-(4-(methoxycarbonyl)phenyl)-1H-pyrazole-4-carboxylic acid (Intermediate#93) and an appropriate amine.

| Structure | Int # | Name | ¹H NMR δ | MS m/e (M + H)+ |
|---|---|---|---|---|
| 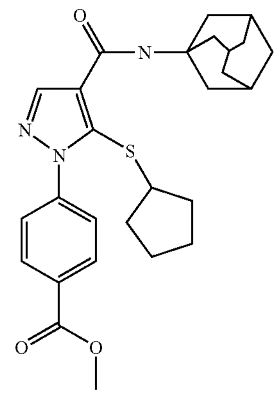 | 91 | methyl 4-[4-(1-adamantylcarbamoyl)-5-cyclopentylsulfanyl-pyrazol-1-yl]benzoate | 1H NMR (400.13 MHz, DMSO-d6) δ 1.19-1.27 (2 H, m), 1.40-1.48 (4 H, m), 1.63-1.71 (8 H, m), 2.07 (9 H, s), 3.31-3.37 (1 H, m), 3.91 (3 H, s), 7.54 (1 H, s), 7.74-7.77 (2 H, m), 8.12-8.15 (3 H, m) | 480 |
| 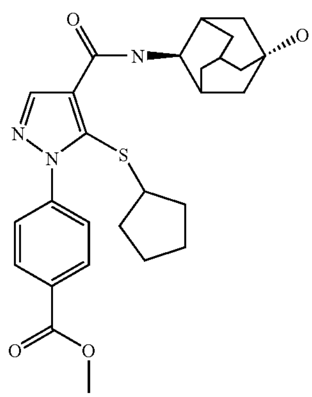 | 92 | methyl 4-[5-cyclopentylsulfanyl-4-[[(1S,3R)-5-hydroxy-2-adamantyl]carbamoyl]pyrazol-1-yl]benzoate | 1H NMR (400.13 MHz, DMSO-d6) δ 1.17-1.24 (2 H, m), 1.32-1.48 (6 H, m), 1.64 (6 H, d), 1.76 (2 H, d), 1.76 (2 H, d), 1.89 (2 H, d), 2.08 (3 H, s), 3.25-3.35 (1 H, m), 3.91 (3 H, s), 4.03 (1 H, t), 4.41 (1 H, s), 7.77-7.81 (2 H, m), 7.98 (1 H, d), 8.13-8.17 (2 H, m), 8.19 (1 H, s) | 496 |

Intermediate #93: 5-cyclopentylsulfanyl-1-(4-methoxycarbonylphenyl)pyrazole-4-carboxylic acid

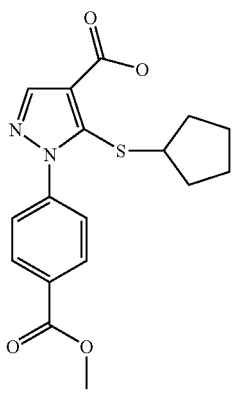

Trifluoroacetic acid (2.63 mL, 34.29 mmol) was added to tert-butyl 5-(cyclopentylthio)-1-(4-(methoxycarbonyl)phenyl)-1H-pyrazole-4-carboxylate (Intermediate#94) (1.38 g, 3.43 mmol) in CH₂Cl₂ (25 mL) The resulting solution was stirred at 20° C. for 24 hours. The reaction mixture was evaporated to dryness, re-dissolved in dioxan (20 mL) and re-evaporated to dryness to afford 5-(cyclopentylthio)-1-(4-(methoxycarbonyl)phenyl)-1H-pyrazole-4-carboxylic acid (1.180 g, 99%) as a white crystalline solid.

1H NMR (400.13 MHz, DMSO-d6) δ 1.20-1.26 (2H, m), 1.37-1.47 (4H, m), 1.65-1.73 (2H, m), 3.65-3.71 (1H, m), 3.86-3.96 (3H, m), 7.68-7.76 (2H, m), 8.11-8.15 (2H, m), 8.19 (1H, s), 12.84 (1H, s)

MS m/z (ESI−) (M−H)−=345

Intermediate#94: tert-butyl 5-cyclopentylsulfanyl-1-(4-methoxycarbonylphenyl)pyrazole-4-carboxylate

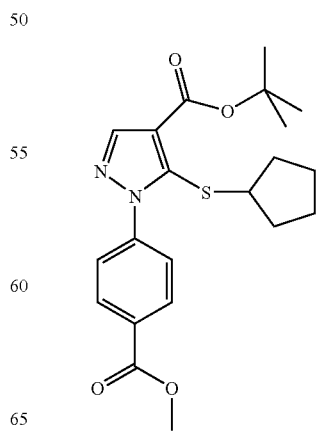

Sodium bis(trimethylsilyl)amide (7.13 mL, 7.13 mmol) was added dropwise to cyclopentanethiol (0.761 mL, 7.13 mmol) in DMF (25 mL) under nitrogen. The resulting solution was stiffed at 20° C. for 30 minutes. A solution of tert-butyl 5-chloro-1-(4-(methoxycarbonyl)phenyl)-1H-pyrazole-4-carboxylate (Intermediate#9) (2 g, 5.94 mmol) in DMF (10 mL) was then added dropwise and the resulting mixture was stirred at 20° C. for 2 hours. The reaction mixture was diluted with EtOAc (200 mL), and washed sequentially with water (4×50 mL) and saturated brine (50 mL). The organic layer was dried over MgSO4, filtered and evaporated to afford crude product. The crude product was purified by flash silica chromatography, elution gradient 0 to 25% EtOAc in isohexane. Pure fractions were evaporated to dryness to afford tert-butyl 5-(cyclopentylthio)-1-(4-(methoxycarbonyl)phenyl)-1H-pyrazole-4-carboxylate (1.380 g, 57.7%) as a colourless oil which crystallised on standing.

1H NMR (300.073 MHz, DMSO-d6) δ 1.14-1.24 (2H, m), 1.35-1.47 (4H, m), 1.54 (9H, s), 1.60-1.77 (2H, m), 3.54-3.58 (1H, m), 3.90 (3H, s), 7.71 (2H, d), 8.11 (2H, d), 8.14 (1H, d) MS m/z (ESI+) (M+H)+=403.

Intermediate#95: Methyl 4-[4-[[5-(difluoromethoxy)-2-adamantyl]carbamoyl]-5-propylsulfanylpyrazol-1-yl]benzoate

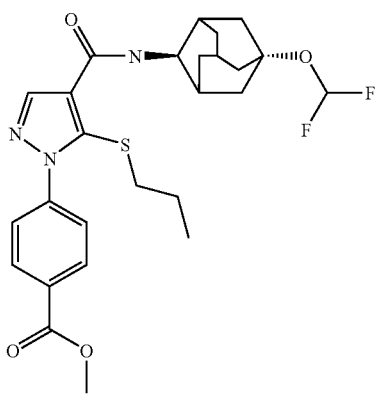

1-(3-Dimethylaminopropyl)-3-ethylcarbodiimide hydrochloride (250 mg, 1.31 mmol) was added in one portion to 1-(4-methoxycarbonylphenyl)-5-propylsulfanylpyrazole-4-carboxylic acid (Intermediate #7) (349 mg, 1.09 mmol), 5-(difluoromethoxy)adamantan-2-amine (Intermediate#121) (260 mg, 1.20 mmol), 1-Hydroxybenzotriazole (176 mg, 1.31 mmol) and N-Ethyldiisopropylamine (0.376 mL, 2.18 mmol) in DMF (10 mL). The resulting mixture was stirred at 20° C. for 5 hours.

The reaction mixture was diluted with EtOAc (100 mL), and washed sequentially with water (4×25 mL) and saturated brine (25 mL). The organic layer was dried over MgSO4, filtered and evaporated to afford crude product.

The crude product was purified by flash silica chromatography, elution gradient 0 to 50% EtOAc in isohexane. Pure fractions were evaporated to dryness to afford methyl 4-[4-[[5-(difluoromethoxy)-2-adamantyl]carbamoyl]-5-propylsulfanyl-pyrazol-1-yl]benzoate (338 mg, 59.8%) as a white crystalline solid.

1H NMR (400.13 MHz, DMSO-d6) δ 0.68 (3H, t), 1.21-1.30 (2H, m), 1.51 (2H, d), 1.90-1.97 (6H, m), 2.05 (2H, d), 2.15-2.20 (3H, m), 2.65 (2H, t), 3.91 (3H, s), 4.09 (1H, d), 6.88 (1H, t), 7.76-7.79 (2H, m), 7.98 (1H, d), 8.13-8.16 (2H, m), 8.19 (1H, s)
m/z (ESI+) (M+H)+=520

Intermediate#96: methyl 4-[4-(cyclohexylcarbamoyl)-5-cyclopentylsulfanyl-pyrazol-1-yl]benzoate

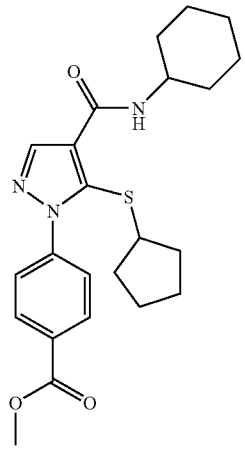

To a solution of cyclopentyl mercaptan (0.071 ml, 0.66 mmol) in DMF (2 ml) was added a 1N solution of NaHMDS in THF (0.66 ml, 0.66 mmol). The reaction was stirred at ambient temperature for 2 minutes then added to a solution of methyl 4-[5-chloro-4-(cyclohexylcarbamoyl)pyrazol-1-yl]benzoate (Intermediate#15) (200 mg, 0.55 mmol) in DMF (3 ml).

The reaction mixture was stirred at room temperature for two hours. The reaction mixture was evaporated to dryness and redissolved in DCM (50 mL) and washed with saturated NH4Cl (10 mL), water (10 mL) and brine (10 mL). It was dried over MgSO4 and the solvent was evaporated under reduced pressure to give a solid. The crude product was purified by flash silica chromatography, elution gradient 0 to 50% EtOAc in isohexane. Pure fractions were evaporated to dryness to afford methyl 4-[4-(cyclohexylcarbamoyl)-5-cyclopentylsulfanyl-pyrazol-1-yl]benzoate (233 mg, 98%) as a solid.

m/z (ESI+) (M+H)+=428

Intermediate#97: methyl 4-[4-(cyclohexylcarbamoyl)-5-cyclohexylsulfanylpyrazol-1-yl]benzoate

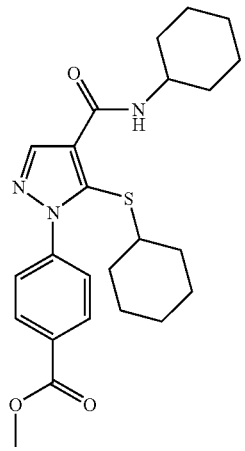

Methyl 4-[4-(cyclohexylcarbamoyl)-5-cyclohexylsulfanylpyrazol-1-yl]benzoate was prepared from cyclohexylthiol and methyl 4-[5-chloro-4-(cyclohexylcarbamoyl)pyrazol-1-yl]benzoate (Intermediate#15) by the same process used for Intermdiate#96.

m/z (ESI+) (M+H)+=442

Intermediate#98: methyl 4-[5-cycloheptylsulfanyl-4-(cyclohexylcarbamoyl)pyrazol-1-yl]benzoate

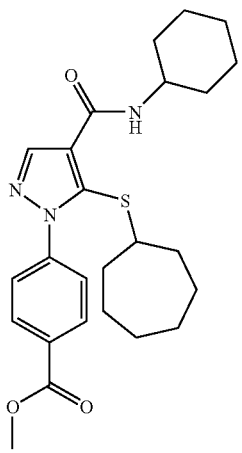

Methyl 4-[5-cycloheptylsulfanyl-4-(cyclohexylcarbamoyl)pyrazol-1-yl]benzoate was prepared from cycloheptylthiol and methyl 4-[5-chloro-4-(cyclohexylcarbamoyl)pyrazol-1-yl]benzoate (Intermediate#15) by the same process used for Intermdiate#96.

m/z (ESI+) (M+H)+=456; HPLC tR=3.27 min.

1H NMR (300.072 MHz, CDCl$_3$) δ 1.08-1.48 (15H, m), 1.56-1.72 (5H, m), 1.91-1.97 (2H, m), 2.84-2.93 (1H, m), 3.90 (3H, s), 3.93-4.02 (1H, m), 7.57-7.65 (3H, m), 8.08-8.12 (2H, d), 8.22 (1H, s)

Intermediate#99: methyl 4-[4-(2-adamantylcarbamoyl)-5-ethylsulfanyl-pyrazol-1-yl]benzoate

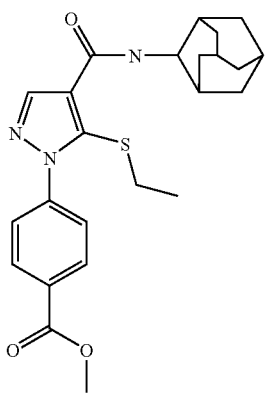

N-(3-Dimethylaminopropyl)-N'-ethylcarbodiimide hydrochloride (396 mg, 2.07 mmol) was added in one portion to 2-Adamantanamine hydrochloride (324 mg, 1.72 mmol), 5-(ethylthio)-1-(4-(methoxycarbonyl)phenyl)-1H-pyrazole-4-carboxylic acid (528 mg, 1.72 mmol) (Intermediate#101), 1-Hydroxybenzotriazole (279 mg, 2.07 mmol) and N-Ethyldiisopropylamine (0.885 mL, 5.17 mmol) in DMF (10 mL). The resulting mixture was stirred at 20° C. for 18 hours.

The reaction mixture was diluted with EtOAc (100 mL), and washed sequentially with water (4×25 mL) and saturated brine (25 mL). The organic layer was dried over MgSO4, filtered and evaporated to afford crude product.

The crude product was purified by flash silica chromatography, elution gradient 0 to 50% EtOAc in isohexane. Pure fractions were evaporated to dryness to afford methyl 4-[4-(2-adamantylcarbamoyl)-5-ethylsulfanyl-pyrazol-1-yl]benzoate (430 mg, 56.8%) as a white solid.

1H NMR (400.13 MHz, DMSO-d$_6$) δ 0.94 (3H, t), 1.62 (2H, d), 1.74 (2H, s), 1.86 (6H, d), 1.96-2.02 (4H, m), 2.68 (2H, q), 3.91 (3H, s), 4.11 (1H, t), 7.76-7.80 (2H, m), 8.04 (1H, d), 8.13-8.16 (2H, m), 8.20 (1H, s)

m/z (ESI+) (M+H)+=440

Intermediate#100: methyl 4-[4-(2-adamantylcarbamoyl)-5-methylsulfanyl-pyrazol-1-yl]benzoate

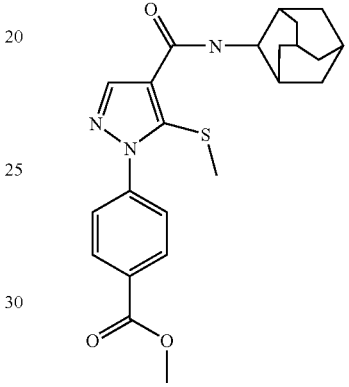

Prepared from methyl 4-[4-(2-adamantylcarbamoyl)-5-methylsulfanyl-pyrazol-1-yl]benzoate (Intermediate#102) by the same process as Intermediate#101.

1H NMR (400.13 MHz, DMSO-d$_6$) δ 1.61 (2H, d), 1.74 (2H, s), 1.86 (6H, s), 1.95-2.04 (4H, m), 2.29 (3H, s), 3.91 (3H, s), 4.11 (1H, t), 7.76-7.79 (2H, m), 8.02 (1H, d), 8.13-8.16 (2H, m), 8.19 (1H, s)

m/z (ESI+) (M+H)+=426

Intermediate #101: 5-(ethylthio)-1-(4-(methoxycarbonyl)phenyl)-1H-pyrazole-4-carboxylic acid

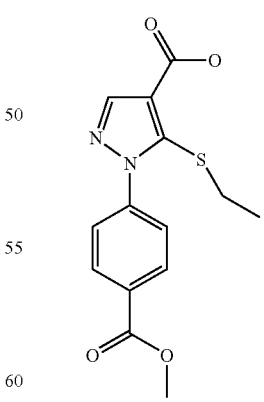

Trifluoroacetic acid (1.324 mL, 17.24 mmol) was added to tert-butyl 5-(ethylthio)-1-(4-(methoxycarbonyl)phenyl)-1H-pyrazole-4-carboxylate (Intermediate#103) (625 mg, 1.72 mmol) in CH2Cl2 (25 mL) The resulting solution was stirred at 20° C. for 24 hours.

The reaction mixture was evaporated to dryness and redissolved in dioxan (20 mL), and re-evaporated to dryness to afford 5-(ethylthio)-1-(4-(methoxycarbonyl)phenyl)-1H-pyrazole-4-carboxylic acid (528 mg, 100%) as a white solid.

1H NMR (400.13 MHz, DMSO-d$_6$) δ 0.96 (3H, t), 2.88 (2H, q), 3.91 (3H, s), 7.70-7.74 (2H, m), 8.12-8.15 (2H, m), 8.19 (1H, s), 12.72 (1H, s)

m/z (ESI+) (M+H)+=307

Intermediate #102: 5-(methylthio)-1-(4-(methoxycarbonyl)phenyl)-1H-pyrazole-4-carboxylic acid

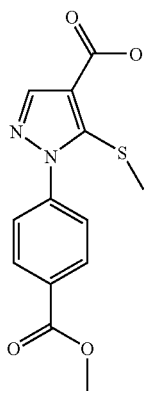

Prepared from tert-butyl 1-(4-(methoxycarbonyl)phenyl)-5-(methylthio)-1H-pyrazole-4-carboxylate (Intermediate#104) by the same process as Intermediate#101.

1H NMR (400.13 MHz, DMSO-d$_6$) δ 2.40 (3H, s), 3.90 (3H, d), 7.72-7.75 (2H, m), 8.10-8.14 (2H, m), 8.17 (1H, s), 12.77 (1H, s)

m/z (ESI+) (M+H)+=293

Intermediate#103: tert-butyl 5-(ethylthio)-1-(4-(methoxycarbonyl)phenyl)-1H-pyrazole-4-carboxylate

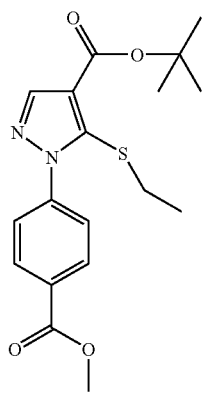

Sodium bis(trimethylsilyl)amide (3.56 mL, 3.56 mmol) was added dropwise to ethanethiol (0.264 mL, 3.56 mmol) in DMF (10 mL) under nitrogen. The resulting solution was stirred at 20° C. for 30 minutes. tert-butyl 5-chloro-1-(4-(methoxycarbonyl)phenyl)-1H-pyrazole-4-carboxylate (Intermediate#9) (1 g, 2.97 mmol) was added in one portion and the resulting suspension was stirred at 20° C. for 5 hours. The reaction mixture was diluted with EtOAc (100 mL), and washed sequentially with water (4×25 mL), and saturated brine (25 mL). The organic layer was dried over MgSO4, filtered and evaporated to afford crude product.

The crude product was purified by flash silica chromatography, elution gradient 0 to 30% EtOAc in isohexane. Product containing fractions were evaporated to dryness to afford tert-butyl 5-(ethylthio)-1-(4-(methoxycarbonyl)phenyl)-1H-pyrazole-4-carboxylate (0.625 g, 58.1%) as a white crystalline solid.

1H NMR (400.13 MHz, DMSO-d$_6$) δ 0.96 (3H, t), 1.55-1.56 (9H, m), 2.84 (2H, q), 3.91 (3H, s), 7.70-7.73 (2H, m), 8.10-8.15 (3H, m)

m/z (ESI+) (M+H)+=363

Intermediate#104: tert-butyl 1-(4-(methoxycarbonyl)phenyl)-5-(methylthio)-1H-pyrazole-4-carboxylate

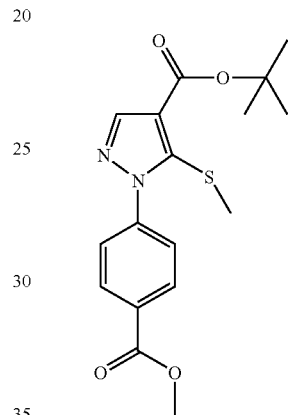

Prepared from (Intermediate#9) and sodium methanethiolate by a similar process to that used for (Intermediate#103).

1H NMR (400.13 MHz, DMSO-d$_6$) δ 1.56 (9H, s), 2.38 (3H, s), 3.91 (3H, s), 7.72-7.74 (2H, m), 8.10-8.17 (3H, m)

m/z (ESI+) (M+H)+=349

Intermediate#105: 4-[4-(5-Methanesulfonyl-adamantan-2-ylcarbamoyl)-5-propylsulfanyl-pyrazol-1-yl]-benzoic acid methyl ester

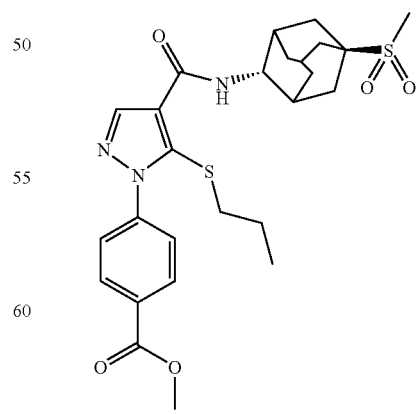

1-(3-Dimethylaminopropyl)-3-ethylcarbodiimide hydrochloride (127 mg, 0.66 mmol) was added to 1-(4-(methoxycarbonyl)phenyl)-5-(propylthio)-1H-pyrazole-4-carboxylic acid (Intermediate#7) (152 mg, 0.47 mmol) 5-Methanesulfonyl-adamantan-2-ylamine (Prepared by the method described in *Bioorganic & Medicinal Chemistry Letters* 17 (2007) 527-532) (109 mg, 0.47 mmol), 4-Dimethylaminopyridine (11.59 mg, 0.09 mmol) and Triethylamine (0.132 mL, 0.95 mmol) in DCM (7 mL) at ambient temperature under nitrogen. The resulting solution was stirred at ambient temperature for 20 hours.

The reaction mixture was evaporated to dryness and redissolved in EtOAc (50 mL), and washed sequentially with 1N citric acid (25 mL), water (20 mL), and saturated brine (20 mL). The organic layer was dried over MgSO4, filtered and evaporated to afford crude product. The crude product was purified by flash silica chromatography, elution gradient 20 to 100% EtOAc in isohexane. Pure fractions were evaporated to dryness to afford 4-[4-(5-Methanesulfonyl-adamantan-2-yl-carbamoyl)-5-propylsulfanyl-pyrazol-1-yl]-benzoic acid methyl ester (116 mg, 46.0%) as a white solid.

1H NMR (400.13 MHz, CDCl$_3$) δ 0.76 (3H, t), 1.31-1.40 (2H, m), 1.71 (2H, d), 1.96 (2H, d), 2.11 (2H, s), 2.15-2.30 (5H, m), 2.33 (2H, s), 2.54 (2H, t), 2.78 (3H, s), 3.97 (3H, s), 4.30-4.40 (1H, m), 7.71 (2H, d), 8.07 (1H, d), 8.20 (2H, d), 8.30 (1H, s)

MS m/e MH$^+$ 532.

Intermediate#106: methyl 4-[4-(2-adamantylcarbamoyl)-5-propylsulfanyl-pyrazol-1-yl]-2-methoxy-benzoate

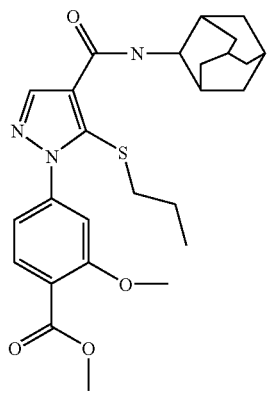

N-(3-Dimethylaminopropyl)-N'-ethylcarbodiimide hydrochloride (197 mg, 1.03 mmol) was added in one portion to 2-adamantanamine hydrochloride (161 mg, 0.86 mmol), 1-(3-methoxy-4-(methoxycarbonyl)phenyl)-5-(propylthio)-1H-pyrazole-4-carboxylic acid (Intermediate#107) (300 mg, 0.86 mmol) 1-Hydroxybenzotriazole (139 mg, 1.03 mmol) and N-Ethyldiisopropylamine (0.440 mL, 2.57 mmol) in DMF (10 mL). The resulting mixture was stirred at 20° C. for 18 hours.

The reaction mixture was diluted with EtOAc (100 mL), and washed sequentially with water (4×25 mL) and saturated brine (25 mL). The organic layer was dried over MgSO4, filtered and evaporated to afford crude product.

The crude product was purified by flash silica chromatography, elution gradient 0 to 50% EtOAc in isohexane. Pure fractions were evaporated to dryness to afford methyl 4-[4-(2-adamantylcarbamoyl)-5-propylsulfanyl-pyrazol-1-yl]-2-methoxy-benzoate (243 mg, 58.7%) as colourless oil.

1H NMR (400.13 MHz, DMSO-d$_6$) δ 0.69 (3H, t), 1.24-1.32 (2H, m), 1.62 (2H, d), 1.74 (2H, s), 1.86 (6H, d), 1.95-2.02 (4H, m), 2.65 (2H, t), 3.83 (3H, s), 3.88 (3H, s), 4.11 (1H, d), 7.26-7.29 (1H, m), 7.44 (1H, d), 7.83 (1H, d), 8.09 (1H, d), 8.18 (1H, s)

m/z (ESI+) (M+H)+=484

Intermediate#107: 1-(3-methoxy-4-(methoxycarbonyl)phenyl)-5-(propylthio)-1H-pyrazole-4-carboxylic acid

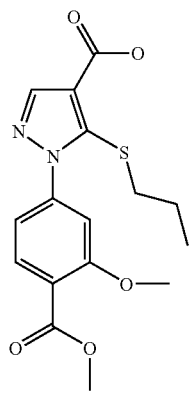

Trifluoroacetic acid (1.194 mL, 15.55 mmol) was added to tert-butyl 1-(3-methoxy-4-(methoxycarbonyl)phenyl)-5-(propylthio)-1H-pyrazole-4-carboxylate (Intermediate#108) (632 mg, 1.55 mmol) in CH2Cl2 (15 mL) The resulting solution was stirred at 20° C. for 24 hours.

The reaction mixture was evaporated to dryness and re-dissolved in dioxan (20 mL), and re-evaporated to dryness to afford 1-(3-methoxy-4-(methoxycarbonyl)phenyl)-5-(propylthio)-1H-pyrazole-4-carboxylic acid (540 mg, 99%) as a colourless oil which solidified on standing.

1H NMR (400.13 MHz, DMSO-d$_6$) δ 0.72 (3H, t), 1.25-1.34 (2H, m), 2.85 (2H, t), 3.57 (1H, s), 3.83 (3H, s), 3.87 (3H, s), 7.19-7.22 (1H, m), 7.36-7.36 (1H, m), 7.82 (1H, d), 8.18 (1H, s), 12.6 (1H, s)

m/z (ESI+) (M+H)+=351

Intermediate#108: tert-butyl 1-(3-methoxy-4-(methoxycarbonyl)phenyl)-5-(propylthio)-1H-pyrazole-4-carboxylate

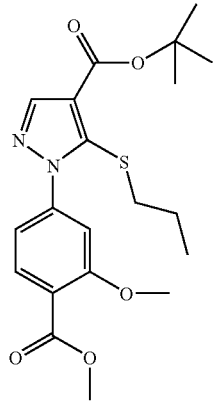

Sodium bis(trimethylsilyl)amide 1M solution in THF (3.60 mL, 3.60 mmol) was added dropwise to 1-propanethiol (0.326 mL, 3.60 mmol) in DMF (10 mL) under nitrogen. The resulting solution was stirred at 20° C. for 30 minutes. tert-butyl 5-chloro-1-(3-methoxy-4-(methoxycarbonyl)phenyl)-1H-pyrazole-4-carboxylate (Intermediate#109) (1.1 g, 3.00 mmol) was added as a solution in DMF (5 mL) and the resulting mixture was stirred at 20° C. for 5 hours. The reaction mixture was diluted with EtOAc (100 mL), and washed sequentially with water (4×25 mL), and saturated brine (25 mL). The organic layer was dried over MgSO4, filtered and evaporated to afford crude product.

The crude product was purified by flash silica chromatography, elution gradient 0 to 50% EtOAc in isohexane. Product containing fractions were evaporated to dryness to afford tert-butyl 1-(3-methoxy-4-(methoxycarbonyl)phenyl)-5-(propylthio)-1H-pyrazole-4-carboxylate (0.642 g, 52.7%) as a colourless oil.

1H NMR (400.13 MHz, DMSO-$d_6$) δ 0.72 (3H, t), 1.29 (2H, q), 1.55 (9H, s), 2.79 (2H, t), 3.83 (3H, s), 3.87 (3H, s), 7.19-7.22 (1H, m), 7.36 (1H, d), 7.82 (1H, d), 8.14 (1H, s)

m/z (ESI+) (M+H)+=407

Intermediate#109: tert-butyl 5-chloro-1-(3-methoxy-4-(methoxycarbonyl)phenyl)-1H-pyrazole-4-carboxylate

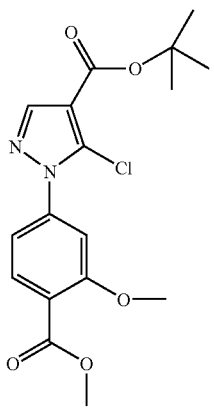

Copper(II) chloride (0.917 g, 6.82 mmol) was added in one portion to tert-Butyl nitrite (0.649 mL, 5.46 mmol) in acetonitrile (25 mL) at and warmed to 50° C. The resulting mixture was stirred at 50° C. while tert-butyl 5-amino-1-(3-methoxy-4-(methoxycarbonyl)phenyl)-1H-pyrazole-4-carboxylate (Intermediate#110) (1.58 g, 4.55 mmol) was added in portions as a solid. After the addition was complete the reaction mixture was stirred at 50° C. for 15 minutes and then cooled to 20° C. The reaction mixture was diluted with EtOAc (100 mL), and washed sequentially with water (2×50 mL), and saturated brine (25 mL). The organic layer was dried over MgSO4, filtered and evaporated to afford crude product. The crude product was purified by flash silica chromatography, elution gradient 0 to 50% EtOAc in isohexane. Fractions were evaporated to dryness to afford tert-butyl 5-chloro-1-(3-methoxy-4-(methoxycarbonyl)phenyl)-1H-pyrazole-4-carboxylate (1.120 g, 67.1%) as a yellow oil.

1H NMR (400.13 MHz, DMSO-$d_6$) δ1.55 (9H, s), 3.83 (3H, s), 3.88 (3H, s), 7.26-7.29 (1H, m), 7.42 (1H, d), 7.84 (1H, d), 8.20 (1H, s)

m/z (ESI+) (M+H)+=367

Intermediate#110: tert-butyl 5-amino-1-(3-methoxy-4-(methoxycarbonyl)phenyl)-1H-pyrazole-4-carboxylate

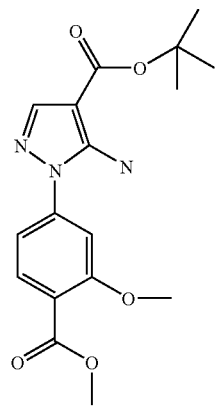

Acetic anhydride (2.83 mL, 30.00 mmol) was added in one portion to tert-Butyl cyanoacetate (4.29 mL, 30 mmol), and triethyl orthoformate (7.48 mL, 45.00 mmol). The resulting mixture was stirred at 125° C. for 3 hours and then volatiles were removed by evaporation under reduced pressure. The resulting oil was dissolved in a ethanol (50 mL), treated with methyl 4-hydrazinyl-2-methoxybenzoate hydrochloride (Intermediate#111) (2.094 g, 9.00 mmol) and N-Ethyldiisopropylamine (1.572 mL, 9.00 mmol) and stirred at 80° C. for 4 h.

The reaction mixture was concentrated and diluted with EtOAc (200 mL), and washed sequentially with water (2×100 mL), and saturated brine (50 mL). The organic layer was dried over MgSO4, filtered and evaporated to afford crude product.

The crude product was purified by flash silica chromatography, elution gradient 0 to 50% EtOAc in isohexane. Pure fractions were evaporated to dryness to afford tert-butyl 5-amino-1-(3-methoxy-4-(methoxycarbonyl)phenyl)-1H-pyrazole-4-carboxylate (1.640 g, 52%) as an orange solid.

1H NMR (400.13 MHz, DMSO-$d_6$) δ 1.52 (9H, s), 3.81 (3H, s), 3.89 (3H, s), 6.47 (2H, s), 7.21-7.23 (1H, m), 7.30 (1H, d), 7.68 (1H, s), 7.81 (1H, d)

m/z (ESI+) (M+H)+=348

Intermediate#111: methyl 4-hydrazinyl-2-methoxybenzoate hydrochloride

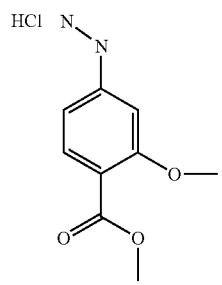

tert-butyl 1-(3-methoxy-4-(methoxycarbonyl)phenyl)hydrazinecarboxylate (Intermediate#112) (4.86 g, 16.40 mmol) was added to a 4M solution of hydrogen chloride (61.5 mL, 246 mmol) in dioxane. The resulting solution was stirred at 20° C. for 5 hours. The reaction mixture was evaporated to dryness and the crude residue was triturated with Et2O to give a solid which was collected by filtration and dried under vacuum to give methyl 4-hydrazinyl-2-methoxybenzoate hydrochloride (3.50 g, 92%) as a pale green solid.

1H NMR (400.13 MHz, DMSO-$d_6$) δ 3.73 (3H, s), 3.81 (3H, s), 6.53-6.56 (1H, m), 6.79 (1H, d), 7.66 (1H, d), 8.79 (1H, s), 10.44 (3H, s)

m/z (ESI+) (M+H)+=197

Intermediate#112: tert-butyl 1-(3-methoxy-4-(methoxycarbonyl)phenyl)hydrazinecarboxylate

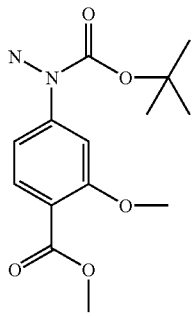

is Copper(I) iodide (0.213 g, 1.12 mmol) was added to 1,10-Phenanthroline (0.403 g, 2.24 mmol), tert-Butyl carbazate (3.55 g, 26.83 mmol), cesium carbonate (10.20 g, 31.30 mmol) and methyl 4-iodo-2-methoxybenzoate (6.53 g, 22.36 mmol) in DMF (75 mL) under nitrogen. The resulting mixture was stirred at 100° C. for 1 hour. The reaction mixture was diluted with EtOAc (400 mL), and washed sequentially with water (4×100 mL), and saturated brine (50 mL). The organic layer was dried over MgSO4, filtered and evaporated to afford crude product.

The crude product was purified by flash silica chromatography, elution gradient 0 to 50% EtOAc in isohexane. Pure fractions were evaporated to dryness to afford tert-butyl 1-(3-methoxy-4-(methoxycarbonyl)phenyl)hydrazinecarboxylate (4.86 g, 73.4%) as a solid.

1H NMR (400.13 MHz, DMSO-$d_6$) δ 1.50 (9H, s), 3.76 (3H, s), 3.80 (3H, s), 5.11 (2H, s), 7.25-7.28 (1H, m), 7.39 (1H, d), 7.64 (1H, d)

m/z (ESI+) (M+H)+=297

Intermediate#113: Ethyl 4-[4-(2-adamantylcarbamoyl)-5-tert-butyl-pyrazol-1-yl]-3-methyl-benzoate

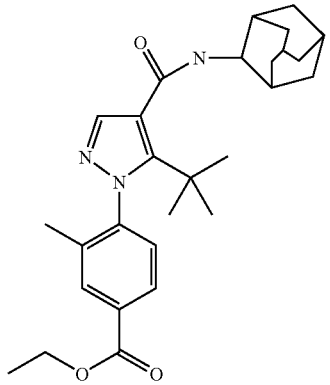

N-(2-adamantyl)-1-(4-chloro-2-methyl-phenyl)-5-tert-butyl-pyrazole-4-carboxamide (Intermediate#114) (647 mg, 1.52 mmol), Molybdenum hexacarbonyl (0.102 mL, 0.76 mmol), 4-Dimethylaminopyridine (371 mg, 3.04 mmol), N-Ethyldiisopropylamine (0.529 mL, 3.04 mmol), trans-Di-mu-acetatobis[2-(di-o-tolylphosphino)benzyl]dipalladium (II) (71.4 mg, 0.08 mmol) and Tri-tert-butylphosphine tetrafluoroborate (88 mg, 0.30 mmol) were suspended in ethanol (6 mL) and dioxane (6.00 mL) and sealed into a microwave tube. The reaction was heated to 150° C. for 1 hour in the microwave reactor and cooled to RT. The reaction mixture was evaporated to dryness and redissolved in EtOAc (100), and washed with water (10 mL), filtered, then washed with 2M HCl (10 mL), and saturated brine (10 mL). The organic layer was dried over MgSO4, filtered and evaporated to afford crude product. The crude product was purified by flash silica chromatography, elution gradient 0 to 25% EtOAc in isohexane. Pure fractions were evaporated to dryness to afford ethyl 4-[4-(2-adamantylcarbamoyl)-5-tert-butyl-pyrazol-1-yl]-3-methyl-benzoate (352 mg, 50.0%) as a colourless oil.

m/z (ESI+) (M+H)+=3.22; HPLC $t_R$=464 min.

1H NMR (300.072 MHz, cdcl3) δ 1.25 (s, 9H), 1.42 (t, 3H), 1.66-1.95 (m, 12H), 2.01-2.10 (m, 2H), 2.13 (s, 3H), 4.22 (d, 1H), 4.41 (q, 2H), 6.14 (d, 1H), 7.31 (d, 1H), 7.68 (s, 1H), 7.94 (d, 1H), 8.01 (s, 1H)

Intermediate#114: N-(2-adamantyl)-1-(4-chloro-2-methyl-phenyl)-5-tert-butyl-pyrazole-4-carboxamide

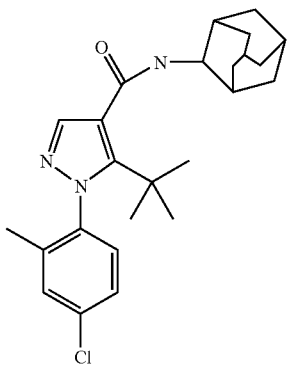

N-(3-Dimethylaminopropyl)-N'-ethylcarbodiimide hydrochloride (Intermediate#115) (515 mg, 2.68 mmol) was added in one portion to 2-Adamantanamine hydrochloride (420 mg, 2.24 mmol), 5-tert-butyl-1-(4-chloro-2-methylphenyl)-1H-pyrazole-4-carboxylic acid (655 mg, 2.24 mmol), 1-Hydroxybenzotriazole (363 mg, 2.68 mmol) and N-Ethyldiisopropylamine (1.149 mL, 6.71 mmol) in DMF (10 mL). The resulting mixture was stirred at 20° C. for 18 hours. The reaction mixture was diluted with Et2O (100 mL), and washed sequentially with water (3×25 mL), and saturated brine (25 mL). The organic layer was dried over MgSO4, filtered and evaporated to afford desired product N-(2-adamantyl)-1-(4-chloro-2-methyl-phenyl)-5-tert-butyl-pyrazole-4-carboxamide (860 mg, 90%).

1H NMR (300.072 MHz, cdcl3) δ 1.26 (s, 9H), 1.51-2.18 (m, 17H), 4.22 (d, 1H), 6.12 (d, 1H), 7.17 (d, 1H), 7.25 (d, 1H), 7.31 (s, 1H), 7.65 (s, 1H)

Intermediate#115: 5-tert-butyl-1-(4-chloro-2-methylphenyl)-1H-pyrazole-4-carboxylic acid

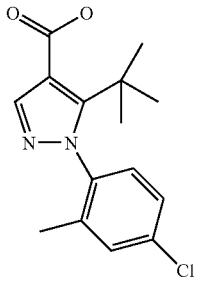

5-tert-butyl-1-(4-chloro-2-methylphenyl)-1H-pyrazole-4-carboxylic acid was prepared from ethyl 5-tert-butyl-1-(4-chloro-2-methylphenyl)-1H-pyrazole-4-carboxylate (Intermediate#116) by the same process used for Intermediate#119.

$^1$H NMR (300.072 MHz, cdcl3) δ 1.30 (s, 9H), 2.04 (s, 3H), 7.15 (d, 1H), 7.26 (d, 1H), 7.31 (s, 1H), 8.16 (s, 1H)

m/z (ESI+) (M+H)+=293

Intermediate#116: Ethyl 5-tert-butyl-1-(4-chloro-2-methylphenyl)-1H-pyrazole-4-carboxylate

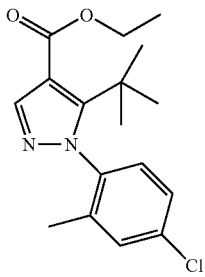

N-Ethyldiisopropylamine (1.553 mL, 8.97 mmol) was added to (4-chloro-2-methylphenyl)hydrazine hydrochloride (1.733 g, 8.97 mmol) and (Z)-ethyl 2-((dimethylamino)methylene)-4,4-dimethyl-3-oxopentanoate (Intermediate#83) (2.04 g, 8.97 mmol) in ethanol (30 mL). The resulting solution was stirred at 90° C. for 2 hours. The reaction mixture was evaporated to dryness and redissolved in DCM (50 mL), and washed sequentially with water (2×10 mL). The organic layer was dried over MgSO4, filtered and evaporated to afford crude product. The crude product was purified by flash silica chromatography, elution gradient 0 to 10% EtOAc in isohexane. Pure fractions were evaporated to dryness to afford ethyl 5-tert-butyl-1-(4-chloro-2-methylphenyl)-1H-pyrazole-4-carboxylate (0.891 g, 30.9%) as a orange oil.

$^1$H NMR (300.072 MHz, cdcl3) δ 1.29 (s, 9H), 1.38 (t, 3H), 2.03 (s, 3H), 4.31 (q, 2H), 7.14 (d, 1H), 7.23 (d, 1H), 7.29 (d, 1H), 8.04 (s, 1H)

m/z (ESI+) (M+H)+=321

Intermediate#117: Ethyl 4-[4-(2-adamantylcarbamoyl)-5-tert-butyl-pyrazol-1-yl]-2-(trifluoromethyl)benzoate

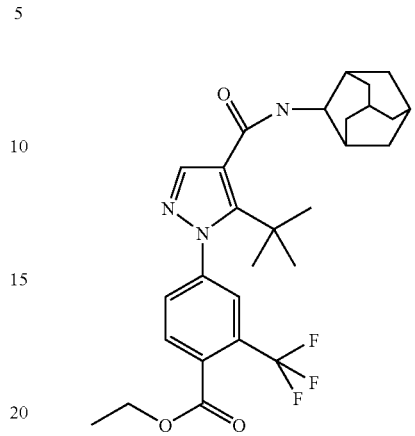

Ethyl 4-[4-(2-adamantylcarbamoyl)-5-tert-butyl-pyrazol-1-yl]-2-(trifluoromethyl)benzoate was prepared from N-(2-adamantyl)-1-[4-chloro-3-(trifluoromethyl)phenyl]-5-tert-butyl-pyrazole-4-carboxamide (Intermediate#118) by the same process used for Intermediate#113.

$^1$H NMR (300.072 MHz, CDCl$_3$) δ 1.27-1.33 (9H, m), 1.42 (3H, t), 1.74-1.79 (5H, m), 1.85-1.91 (7H, m), 2.06 (2H, s), 4.23 (1H, d), 4.44 (2H, q), 6.13 (1H, d), 7.62 (1H, d), 7.62 (1H, t), 7.75-7.76 (1H, m), 7.92 (1H, d)

m/z (ESI+) (M+H)+=518

Intermediate#118: N-(2-adamantyl)-1-[4-chloro-3-(trifluoromethyl)phenyl-]-5-tert-butyl-pyrazole-4-carboxamide

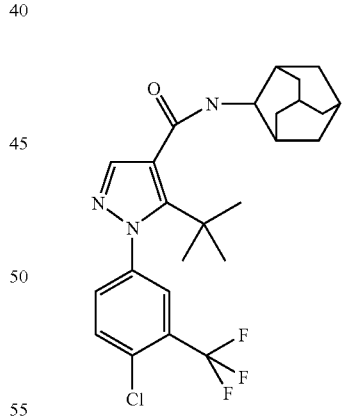

N-(2-adamantyl)-1-[4-chloro-3-(trifluoromethyl)phenyl]-5-tert-butyl-pyrazole-4-carboxamide was prepared from 5-tert-butyl-1-(4-chloro-3-(trifluoromethyl)phenyl)-1H-pyrazole-4-carboxylic acid (Intermediate#119) by the same process used for Intermediate#114.

$^1$H NMR (300.072 MHz, cdcl3) δ 1.29 (s, 9H), 1.55-1.97 (m, 12H), 2.06 (s, 2H), 4.22 (d, 1H), 6.12 (d, 1H), 7.48 (d, 1H), 7.62 (d, 1H), 7.63 (s, 1H), 7.71 (s, 1H)

m/z (ESI+) (M+H)+=480

Intermediate#119: 5-tert-butyl-1-(4-chloro-3-(trifluoromethyl)phenyl)-1H-pyrazole-4-carboxylic acid

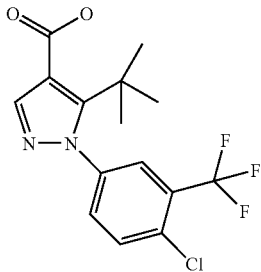

A solution of Sodium hydroxide (6.67 mL, 13.34 mmol) was added in one portion to a stirred solution of ethyl 5-tert-butyl-1-(4-chloro-3-(trifluoromethyl)phenyl)-1H-pyrazole-4-carboxylate (Intermediate#120) (1 g, 2.67 mmol) in methanol (20 mL). The resulting suspension was stirred at 80° C. for 6 hours. The resulting mixture was evaporated to remove the methanol, washed with ether (20 mL). The reaction mixture was acidified with 2M HCl, extracted with ethyl acetate(2×30 mL) The organic layers were combined and washed with water (10 mL) and brine (10 mL), dried over MgSO4, filtered and evaporated to afford pure 5-tert-butyl-1-(4-chloro-3-(trifluoromethyl)phenyl)-1H-pyrazole-4-carboxylic acid (0.766 g, 83%).

$^1$H NMR (300.072 MHz, cdcl3) δ 1.36 (s, 9H), 7.47 (d, 1H), 7.63 (d, 1H), 7.70 (s, 1H), 8.12 (s, 1H)

m/z (ESI+) (M+H)+=345

Intermediate #120: Ethyl 5-tert-butyl-1-(4-chloro-3-(trifluoromethyl)phenyl)-1H-pyrazole-4-carboxylate

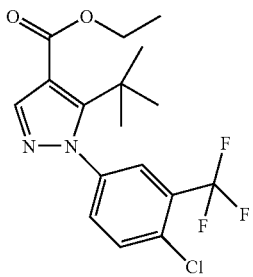

Ethyl 5-tert-butyl-1-(4-chloro-3-(trifluoromethyl)phenyl)-1H-pyrazole-4-carboxylate was prepared from (Z)-ethyl 2-((dimethylamino)methylene)-4,4-dimethyl-3-oxopentanoate (Intermediate#83) and (4-chloro-3-(trifluoromethyl)phenyl)hydrazine hydrochloride by the same process used for Intermediate#116.

$^1$H NMR (300.072 MHz, cdcl3) δ 1.32 (s, 9H), 1.38 (t, 3H), 4.32 (q, 2H), 7.46 (d, 1H), 7.61 (d, 1H), 7.68 (s, 1H), 7.98 (s, 1H)

m/z (ESI+) (M+H)+=375

Intermediate#121: (1R,2S,3S,5S)-5-Difluoromethoxy-adamantan-2-ylamine

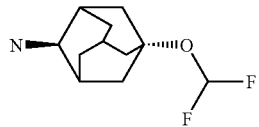

((1R,2S,3S,5S)-5-Difluoromethoxy-adamantan-2-yl)-carbamic acid benzyl ester (Intermediate#122) (255 mg, 0.73 mmol) and Palladium (10% on carbon) (25 mg, 0.23 mmol) in MeOH (5 mL) were stiffed under an atmosphere of hydrogen at 1 atm and ambient temperature for 22 hours. The reaction mixture was filtered through celite and the solvent was evaporated in vacuo to yield (1R,2S,3S,5S)-5-Difluoromethoxy-adamantan-2-ylamine (130 mg, 82%) as a clear oil.

1H NMR (400.13 MHz, CDCl$_3$) δ 1.38-1.44 (5H, m), 1.91-2.00 (9H, m), 2.14 (1H, s), 3.05 (1H, s), 6.15-6.54 (1H, t)

m/z (ESI+) (M+H)+=218

Intermediate#122: ((1R,2S,3S,5S)-5-Difluoromethoxy-adamantan-2-yl)-carbamic acid benzyl ester

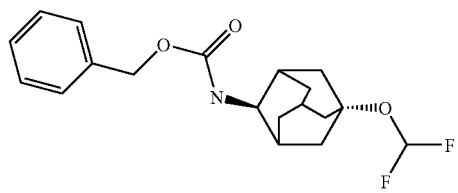

Solution of 2,2-Difluoro-2-(fluorosulfonyl)acetic acid (0.237 mL, 2.30 mmol) in acetonitrile (2 mL was added dropwise to a stirred solution of ((1R,2S,3S,5S)-5-Hydroxy-adamantan-2-yl)-carbamic acid benzyl ester (346 mg, 1.15 mmol) and Copper(I) iodide (7.78 µL, 0.23 mmol) in acetonitrile (10 mL) at 45° C., over a period of 1 hour under nitrogen. The resulting solution was stirred at 45° C. for 15 minutes. The reaction mixture was evaporated to dryness and redissolved in EtOAc (50 mL), and washed sequentially with water (50 mL) and saturated brine (25 mL). The organic layer was dried over MgSO4, filtered and evaporated to afford crude product. The crude product was purified by flash silica chromatography, elution gradient 0 to 30% EtOAc in isohexane. Pure fractions were evaporated to dryness to afford (1R,2S,3S,5S)-5-Difluoromethoxy-adamantan-2-yl)-carbamic acid benzyl ester (269 mg, 66.7%) as a colourless oil.

1H NMR (400.13 MHz, DMSO-d6) δ 1.35 (2H, d), 1.86 (4H, d), 1.94 (4H, t), 2.06 (3H, s), 3.65 (1H, m), 5.04 (2H, s), 6.65-7.03 (1H, t), 7.29-7.42 (6H, m)

Intermediate#123: methyl 4-hydrazinylbenzoate hydrochloride

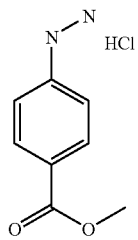

Hydrogen chloride 4M in Dioxan (100 mL, 399.60 mmol) was added to 4-Hydrazinobenzoic acid (15.2 g, 99.90 mmol) in MeOH (200 mL). The resulting suspension was stirred at 90° C. for 5 hours. After cooling to 20° C. the precipitate was collected by filtration, washed with Et2O (100 mL) and dried under vacuum to afford 2-(4-(methoxycarbonyl)phenyl)hydrazinium chloride (16.50 g, 82%) as a cream crystalline solid.

m/z (ESI−) (M−H)−=165; HPLC $t_R$=1.12 min.

1H NMR (400.13 MHz, DMSO-d6) δ 3.81 (3H, s), 6.99-7.02 (2H, m), 7.86-7.90 (2H, m), 8.98 (1H, s), 10.47 (3H, s)

Intermediate#123 may also be prepared as follows:

Methanolic hydrochloric acid solution (4M) (4 equiv., freshly prepared) was added to a suspension of 4-hydrazinobenzoic acid (1 equiv.) in methanol (12.6 vols.), under nitrogen.

The mixture was stirred under reflux for three hours and then cooled to below 15° C. The solid was collected by filtration, washed with MTBE (6.5 vols.) and dried in air to give the product as a solid.

TLC DCM:MeOH, 9:1, Product $R_f$ 0.87 mp 233.8-234.6° C.

Intermediate #124: N-adamantan-2-yl-1-(4-cyanophenyl)-5-(trifluoromethyl)-1H-pyrazole-4-carboxamide

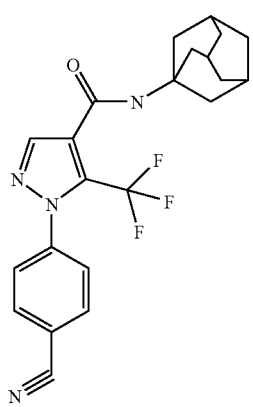

2-Adamantanamine hydrochloride (0.375 g, 2.00 mmol) was added in one portion to 1-(4-cyanophenyl)-5-(trifluoromethyl)-1H-pyrazole-4-carboxylic acid (Intermediate#125) (0.562 g, 2 mmol), 1-Hydroxybenzotriazole (0.297 g, 2.20 mmol), N-Ethyldiisopropylamine (1.384 mL, 8.00 mmol) and 1-(3-Dimethylaminopropyl)-3-ethylcarbodiimide hydrochloride (0.460 g, 2.40 mmol) in DMF (10 mL) under nitrogen.

The resulting solution was stirred at room-temperature for 16 hours. The reaction mixture was poured onto water (75 mL), extracted with EtOAc (2×50 mL), the organic layer was dried over MgSO4, filtered and evaporated to afford beige solid. The crude product was purified by flash silica chromatography, elution gradient 20 to 60% EtOAc in isohexane. Pure fractions were evaporated to dryness to afford N-adamantan-2-yl-1-(4-cyanophenyl)-5-(trifluoromethyl)-1H-pyrazole-4-carboxamide (0.480 g, 57.9%) as a white solid.

m/z (ESI+) (M+H)+=415; HPLC $t_R$=2.82 min.

1H NMR (400.13 MHz, DMSO-$d_6$) δ 1.51 (2H, d), 1.70 (2H, s), 1.81 (5H, s), 1.84 (1H, s), 1.92 (2H, s), 2.04 (2H, d), 4.01 (1H, t), 7.73 (2H, d), 8.08-8.11 (2H, m), 8.18 (1H, s), 8.34 (1H, d).

Intermediate #125: 1-(4-cyanophenyl)-5-(trifluoromethyl)-1H-pyrazole-4-carboxylic acid

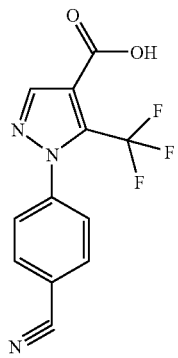

Potassium trimethylsilanolate (3.32 g, 23.28 mmol) was added in one portion to ethyl 1-(4-cyanophenyl)-5-(trifluoromethyl)-1H-pyrazole-4-carboxylate (Intermediate#126) (2.4 g, 7.76 mmol), in THF (50 mL), under nitrogen. The resulting suspension was stirred at room temperature for 3 hours. The reaction mixture was evaporated to dryness and redissolved in EtOAc (100 mL), and washed sequentially with 0.1M HCl (50 mL), water (50 mL), and saturated brine (50 mL). The organic layer was dried over MgSO4, filtered and evaporated to afford crude product. The crude solid was triturated with isohexane to give a solid which was collected by filtration and dried under vacuum to give 1-(4-cyanophenyl)-5-(trifluoromethyl)-1H-pyrazole-4-carboxylic acid (1.600 g, 73.3%) as a orange solid. Used directly in next stage.

m/z (ESI+) (M−H)−=280; HPLC $t_R$=1.86 min.

1H NMR (400.13 MHz, DMSO-$d_6$) δ 7.78-7.80 (2H, m), 8.07-8.10 (2H, m), 8.26 (1H, s), 13.39 (1H, s)

Intermediate#126: Ethyl 1-(4-cyanophenyl)-5-(trifluoromethyl)-1H-pyrazole-4-carboxylate

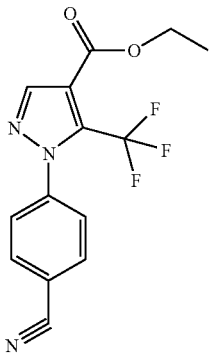

A solution of (Z)-ethyl 2-(ethoxymethylene)-4,4,4-trifluoro-3-oxobutanoate (2.41 g, 10.03 mmol) in ethanol (10 mL) was added dropwise to a stirred solution of 4-hydrazinylbenzonitrile hydrochloride (1.702 g, 10.03 mmol), in ethanol (50 mL) cooled to −10° C. The resulting solution was allowed to stir at room temperature for 16 hours. The reaction mixture was evaporated to dryness and the residue redissolved in EtOAc (100 mL), and washed sequentially with water (50 mL) and saturated brine (50 mL). The organic layer was dried over MgSO4, filtered and evaporated to afford crude product. The crude product was purified by flash silica (120 g) chromatography, elution gradient 10 to 60% EtOAc in isohexane. Pure fractions were evaporated to dryness to afford ethyl 1-(4-cyanophenyl)-5-(trifluoromethyl)-1H-pyrazole-4-carboxylate (2.400 g, 77%) as a white solid.

m/z (ESI+) (M+H)+=310; HPLC $t_R$=2.51 min.

1H NMR (400.13 MHz, DMSO-$d_6$) δ 1.31 (3H, t), 4.33 (2H, q), 7.81-7.84 (2H, m), 8.10-8.13 (2H, m), 8.38-8.38 (1H, m)

The invention claimed is:

1. The compound 4-[4-(2-adamantylcarbamoyl)-5-tert-butyl-pyrazol-1-yl]benzoic acid or a pharmaceutically-acceptable salt thereof.

2. A pharmaceutical composition comprising a compound according to claim 1 or a pharmaceutically-acceptable salt thereof, together with a pharmaceutically acceptable diluent or carrier.

3. A process for the preparation of the 4-[4-(2-adamantylcarbamoyl)-5-tert-butyl-pyrazol-1-yl]benzoic acid or a pharmaceutically-acceptable salt thereof comprising hydrolyzing methyl 4-[4-(2-adamantylcarbamoyl)-5-tert-butyl-pyrazol-1-yl]benzoate and thereafter optionally forming a pharmaceutically-acceptable salt thereof.

* * * * *